United States Patent
Taylor et al.

(10) Patent No.: US 9,073,053 B2
(45) Date of Patent: *Jul. 7, 2015

(54) APPARATUS AND METHOD FOR CELL DISRUPTION

(75) Inventors: Michael T. Taylor, Newark, CA (US); Phillip Belgrader, Manteca, CA (US); Farzad Pourahmadi, Fremont, CA (US); William A. McMillan, Cupertino, CA (US); Ronald Chang, Redwood City, CA (US); Stanley H. Sakai, Cupertino, CA (US); Jesus Ching, Santa Clara, CA (US)

(73) Assignee: Cepheid, Sunnyvale, CA (US)

( * ) Notice: Subject to any disclaimer, the term of this patent is extended or adjusted under 35 U.S.C. 154(b) by 1944 days.

This patent is subject to a terminal disclaimer.

(21) Appl. No.: 11/233,629

(22) Filed: Sep. 22, 2005

(65) Prior Publication Data

US 2006/0027686 A1 Feb. 9, 2006

Related U.S. Application Data

(63) Continuation of application No. 10/759,741, filed on Jan. 15, 2004, now abandoned, which is a continuation of application No. 09/584,327, filed on May 30, 2000, now abandoned.

(60) Provisional application No. 60/136,703, filed on May 28, 1999.

(51) Int. Cl.
*C12N 1/06* (2006.01)
*B01L 3/00* (2006.01)
*C12M 1/00* (2006.01)

(52) U.S. Cl.
CPC ............ *B01L 3/502* (2013.01); *B01L 2200/10* (2013.01); *B01L 2300/0681* (2013.01); *B01L 2400/0487* (2013.01); *B01L 2400/0644* (2013.01); *B01L 2400/0655* (2013.01); *C12M 47/06* (2013.01)

(58) Field of Classification Search
CPC .... C12M 47/06; B01L 3/502; B01L 2200/10; B01L 2300/0681; B01L 2400/0487; B01L 2400/0655; B01L 2400/0644
USPC .......................................... 241/2; 435/306.1
See application file for complete search history.

(56) References Cited

U.S. PATENT DOCUMENTS 3,448,890 A 6/1969 McGrath
3,799,742 A 3/1974 Coleman
(Continued)

FOREIGN PATENT DOCUMENTS

DE 19519015 9/1996
EP 0 271 448 6/1988
(Continued)

OTHER PUBLICATIONS

Anderson et al., "Microfluidic Biochemical Analysis System," *Transducers '97, Int'l Conf. on Solid-State Sensors and Actuators*, held in Chicago, Jun. 16-19, 1997, pp. 477-480.
(Continued)

*Primary Examiner* — Michael Hobbs
(74) *Attorney, Agent, or Firm* — Kilpatrick Townsend & Stockton LLP

(57) ABSTRACT

An apparatus for disrupting cells or viruses comprises a container having a chamber for holding the cells or viruses. The container includes at least one flexible wall defining the chamber. The apparatus also includes a transducer for impacting an external surface of the flexible wall to generate pressure waves in the chamber. The apparatus also includes a pressure source for increasing the pressure in the chamber. The pressurization of the chamber ensures effective coupling between the transducer and the flexible wall. The apparatus may also include beads in the chamber for rupturing the cells or viruses.

5 Claims, 49 Drawing Sheets

(56) References Cited

U.S. PATENT DOCUMENTS

| | | | |
|---|---|---|---|
| 4,180,383 A * | 12/1979 | Johnson | 422/69 |
| 4,336,719 A | 6/1982 | Lynnworth | |
| 4,426,451 A | 1/1984 | Columbus | |
| 4,615,984 A * | 10/1986 | Stoker | 436/518 |
| 4,642,220 A | 2/1987 | Bjorkman | |
| 4,789,628 A | 12/1988 | Nayak | |
| 4,855,240 A | 8/1989 | Rosenstein et al. | |
| 4,874,137 A | 10/1989 | Chiba | |
| 4,891,120 A | 1/1990 | Sethi et al. | |
| 4,895,500 A | 1/1990 | Hok et al. | |
| 4,908,112 A | 3/1990 | Pace | |
| 4,908,318 A | 3/1990 | Lerner | |
| 4,915,812 A | 4/1990 | Parce et al. | |
| 4,918,025 A | 4/1990 | Greener | |
| 4,921,952 A | 5/1990 | Longmire et al. | |
| 4,923,978 A | 5/1990 | McCormick | |
| 4,963,498 A | 10/1990 | Hillman et al. | |
| 4,983,523 A | 1/1991 | Li et al. | |
| 5,061,446 A | 10/1991 | Guigan | |
| 5,074,474 A | 12/1991 | Golz et al. | |
| 5,114,858 A | 5/1992 | Williams et al. | |
| 5,122,993 A | 6/1992 | Hikita et al. | |
| 5,124,444 A | 6/1992 | Van Ness et al. | |
| 5,143,084 A | 9/1992 | Macemon et al. | |
| 5,155,018 A | 10/1992 | Gillespie et al. | |
| 5,207,988 A | 5/1993 | Lucas | |
| 5,223,219 A | 6/1993 | Subramanian et al. | |
| 5,229,297 A | 7/1993 | Schnipelsky et al. | |
| 5,234,809 A | 8/1993 | Boom et al. | |
| 5,296,375 A | 3/1994 | Kricka et al. | |
| 5,304,487 A | 4/1994 | Wilding et al. | |
| 5,330,916 A | 7/1994 | Williams et al. | |
| 5,342,931 A | 8/1994 | Woodard et al. | |
| 5,352,777 A | 10/1994 | Jhingan | |
| 5,374,522 A | 12/1994 | Murphy et al. | |
| 5,374,533 A | 12/1994 | Matsuzawa et al. | |
| 5,399,486 A | 3/1995 | Cathey et al. | |
| 5,422,241 A | 6/1995 | Goldrick et al. | |
| 5,422,271 A | 6/1995 | Chen et al. | |
| 5,427,663 A | 6/1995 | Austin et al. | |
| 5,427,946 A | 6/1995 | Kricka et al. | |
| 5,438,129 A | 8/1995 | Woodard et al. | |
| 5,443,890 A | 8/1995 | Ohman | |
| 5,458,761 A | 10/1995 | Kamahori et al. | |
| 5,486,335 A | 1/1996 | Wilding et al. | |
| 5,500,071 A | 3/1996 | Kaltenbach et al. | |
| 5,534,054 A | 7/1996 | Woodard et al. | |
| 5,543,305 A | 8/1996 | Cummins et al. | |
| 5,580,435 A | 12/1996 | Kovacs | |
| 5,580,794 A | 12/1996 | Allen | |
| 5,582,829 A | 12/1996 | Alliger et al. | |
| 5,585,069 A | 12/1996 | Zanzucchi et al. | |
| 5,587,128 A | 12/1996 | Wilding et al. | |
| 5,605,662 A | 2/1997 | Heller et al. | |
| 5,616,701 A | 4/1997 | Woodard et al. | |
| 5,639,423 A | 6/1997 | Northrup et al. | |
| 5,639,428 A | 6/1997 | Cottingham | |
| 5,641,400 A | 6/1997 | Kaltenbach et al. | |
| 5,643,738 A | 7/1997 | Zanzucchi et al. | |
| 5,652,141 A | 7/1997 | Henco et al. | |
| 5,660,029 A | 8/1997 | King | |
| 5,660,993 A | 8/1997 | Cathey et al. | |
| 5,705,018 A | 1/1998 | Hartley | |
| 5,707,799 A | 1/1998 | Hansmann et al. | |
| 5,714,380 A | 2/1998 | Neri et al. | |
| 5,716,852 A | 2/1998 | Yager et al. | |
| 5,741,639 A | 4/1998 | Ensing et al. | |
| 5,746,978 A | 5/1998 | Bienhaus et al. | |
| 5,770,029 A | 6/1998 | Nelson et al. | |
| 5,798,215 A | 8/1998 | Cathey et al. | |
| 5,834,272 A * | 11/1998 | Righetti | 435/174 |
| 5,842,787 A | 12/1998 | Kopf-Sill et al. | |
| 5,843,767 A | 12/1998 | Beattie | |
| 5,846,727 A | 12/1998 | Soper et al. | |
| 5,856,174 A | 1/1999 | Lipshutz et al. | |
| 5,858,188 A | 1/1999 | Soane et al. | |
| 5,863,502 A | 1/1999 | Southgate et al. | |
| 5,863,801 A | 1/1999 | Southgate et al. | |
| 5,869,004 A | 2/1999 | Parce et al. | |
| 5,874,046 A | 2/1999 | Megerie | |
| 5,880,071 A | 3/1999 | Parce et al. | |
| 5,882,903 A | 3/1999 | Andrevski et al. | |
| 5,921,678 A | 7/1999 | Desai et al. | |
| 5,922,591 A | 7/1999 | Anderson et al. | |
| 5,948,673 A | 9/1999 | Cottingham | |
| 5,955,029 A | 9/1999 | Wilding et al. | |
| 5,955,351 A | 9/1999 | Gerdes et al. | |
| 5,972,710 A | 10/1999 | Weigl et al. | |
| 5,976,824 A | 11/1999 | Gordon | |
| 5,993,872 A | 11/1999 | Rolle et al. | |
| 6,007,690 A | 12/1999 | Nelson et al. | |
| 6,030,581 A | 2/2000 | Virtanen | |
| 6,042,709 A | 3/2000 | Parce et al. | |
| 6,043,080 A | 3/2000 | Lipshutz et al. | |
| 6,068,752 A | 5/2000 | Dubrow et al. | |
| 6,080,295 A | 6/2000 | Parce et al. | |
| 6,090,545 A | 7/2000 | Wohlstadter et al. | |
| 6,100,084 A | 8/2000 | Miles et al. | |
| 6,106,779 A | 8/2000 | Buechler et al. | |
| 6,129,879 A | 10/2000 | Bersted et al. | |
| 6,153,073 A | 11/2000 | Dubrow et al. | |
| 6,156,273 A | 12/2000 | Regnier et al. | |
| 6,168,948 B1 | 1/2001 | Anderson et al. | |
| 6,194,222 B1 | 2/2001 | Buechler et al. | |
| 6,197,595 B1 | 3/2001 | Anderson et al. | |
| 6,261,431 B1 | 7/2001 | Mathies et al. | |
| 6,315,957 B1 | 11/2001 | Feygin et al. | |
| 6,391,541 B1 | 5/2002 | Petersen et al. | |
| 6,431,476 B1 | 8/2002 | Taylor et al. | |
| 6,440,725 B1 * | 8/2002 | Pourahmadi et al. | 435/288.5 |
| 6,664,104 B2 | 12/2003 | Pourahmadi et al. | |
| 6,686,195 B1 | 2/2004 | Colin et al. | |
| 6,739,531 B2 | 5/2004 | Taylor | |
| 6,881,541 B2 | 4/2005 | Petersen et al. | |
| 6,887,693 B2 | 5/2005 | McMillan et al. | |
| 6,942,169 B2 | 9/2005 | Sparks | |
| 8,268,603 B2 * | 9/2012 | Taylor et al. | 435/173.7 |
| 2002/0019060 A1 | 2/2002 | Petersen et al. | |
| 2002/0039783 A1 | 4/2002 | McMillan et al. | |
| 2002/0045246 A1 | 4/2002 | McMillan et al. | |
| 2002/0055167 A1 | 5/2002 | Pourahmadi et al. | |
| 2004/0200909 A1 | 10/2004 | McMillan et al. | |
| 2006/0019379 A1 | 1/2006 | Taylor et al. | |
| 2007/0190641 A1 | 8/2007 | Wilding et al. | |
| 2008/0057572 A1 | 3/2008 | Petersen et al. | |
| 2012/0009667 A1 | 1/2012 | Petersen et al. | |
| 2012/0171758 A1 | 7/2012 | Petersen et al. | |

FOREIGN PATENT DOCUMENTS

| | | |
|---|---|---|
| EP | 0 337 690 | 10/1989 |
| EP | 0 430 248 | 6/1991 |
| EP | 0 576 602 | 11/1995 |
| EP | 0 123 456 | 1/2000 |
| GB | 938163 | 10/1963 |
| JP | 05-068553 | 3/1993 |
| WO | WO 92/05442 | 4/1994 |
| WO | WO 95/12808 | 5/1995 |
| WO | WO 96/07954 | 3/1996 |
| WO | WO 96/12541 | 5/1996 |
| WO | WO 96/15446 A1 | 5/1996 |
| WO | WO 97/02357 | 1/1997 |
| WO | WO 98/08594 | 3/1998 |
| WO | WO 98/10277 | 3/1998 |
| WO | WO 98/38487 | 9/1998 |
| WO | WO 99/33559 A1 | 7/1999 |

OTHER PUBLICATIONS

Brody et al., "Deformation and Flow of Red Blood Cells in a Synthetic Lattice: Evidence for an Active Cytoskeleton," *Biophysical Journal*, 68:2224-2232 (1995).

Brody et al., "Diffusion-Based Extraction in a Microfabricated Device," *Sensors and Actuators A*, 58:13-18 (1997).

(56) References Cited

OTHER PUBLICATIONS

Branebjerg et al., "Fast Mixing by Lamination," *Proceedings of the Conference on MEMS*, held Feb. 11-15, 1996 in San Diego, CA.
Buck et al., "Rapid, Simple Method for Treating Clinical Specimens Containing Mycobacterium Tuberculosis to Remove DNA for Polymerase Chain Reaction," *J. Clinical Microbiology*, pp. 1331-1334 (1992).
Cuypers et al., "The NucliSens™ Extractror for Automated Nucleic Acid Isolation," *Infusionsther Transfusionsmed*, 25:147-151 (1998).
Klaassen et al., "Silicon Fusion Bonding and Deep Reactive Ion Etching: A New Technology for Microstructures," *Sensors and Actuators A*, 52:132-139 (1996).
Maulf, N., "Silicon Fusion Bonding Plus DRIE Delivers Design Flexibility," *Micromachine Devices*, 2:4-5 (1997).
Sanz et al., "Effect of Ultrasonic Waves on the Heat Resistance of *Bacillus stearothermophilus* Spores Fundamental and Applied Aspects of Bacterial Spores," pp. 251-259 (1985).
1st Canadian Office Action for Application No. 2,373,249 mailed Apr. 28, 2008, 3 pgs.
Carlin, Ultrasonics, 1960, McGraw-Hill, p. 60-65 88-91.
European Patent Office Communication for EP Application No. 00 937 895, mailed Nov. 24, 2003, 7 pgs.
Final Office Action for U.S. Appl. No. 09/854,327, 11 pgs, Jul. 15, 2003.
Final Office Action for U.S. Appl. No. 09/970,434, 12 pgs, Feb. 7, 2005.
Final Office Action for U.S. Appl. No. 11/234,634, 13 pgs, Aug. 16, 2010.
Final Office Action for U.S. Appl. No. 11/234,634, 14 pgs, Aug. 20, 2012.
Final Office Action for U.S. Appl. No. 11/234,656, 14 pgs, May 19, 2011.
Miller, W., "Nucleation and Evolution of Ultrasonic Cavitation in a Rotating Exposure Chamber," 1992, Ultrasound Med, vol. 11, pp. 407-412.
Non-Final Office Action for U.S. Appl. No. 09/584,327, 12 pgs, Nov. 25, 2002.
Non-Final Office Action for U.S. Appl. No. 09/970,434, 10 pgs, Oct. 21, 2003.
Non-Final Office Action for U.S. Appl. No. 09/970,434, 12 pgs, May 18, 2004.
Non-Final Office Action for U.S. Appl. No. 10/759,741, 12 pgs, Mar. 22, 2005.
Non-Final Office Action for U.S. Appl. No. 11/234,634, 10 pgs, Mar. 30, 2009.
Non-Final Office Action for U.S. Appl. No. 11/234,634, 11 pgs, Dec. 17, 2009.
Non-Final Office Action for U.S. Appl. No. 11/234,634, 13 pgs, Apr. 21, 2011.
Non-Final Office Action for U.S. Appl. No. 11/234,634, 14 pgs, Dec. 16, 2011.
Non-Final Office Action for U.S. Appl. No. 11/234,634, 6 pgs, May 2, 2013.
Non-Final Office Action for U.S. Appl. No. 11/234,656, 10 pgs, Mar. 10, 2009.
Non-Final Office Action for U.S. Appl. No. 11/234,656, 13 pgs, Sep. 28, 2010.
PCT International Preliminary Examination Report received Aug. 13, 2010, 11 pgs.
PCT International Search Report mailed Nov. 24, 2000, 4 pgs.
Tran-Son-Tay, R. et al., "Effects of Cell Lysis on the Rheological Behavior of Red Blood Cell Suspensions," J. of Biomech Eng., vol. 112, pp. 257-262 (1990).
US 5,693,782, 12/1997, Woodard et al. (withdrawn)

\* cited by examiner

APPARATUS AND METHOD FOR CELL DISRUPTION

RELATED APPLICATION INFORMATION

This application is a continuation of U.S. patent application Ser. No. 10/759,741, filed Jan. 15, 2004, which is a continuation of U.S. patent application Ser. No. 09/584,327, filed May 30, 2000 (abandoned), which claims the benefit of U.S. provisional patent application No. 60/136,703 filed May 28, 1999. These applications are incorporated by reference herein for all purposes.

FIELD OF THE INVENTION

The present invention relates to an apparatus and method for rapidly disrupting cells or viruses.

BACKGROUND OF THE INVENTION

The extraction of nucleic acid from cells or viruses is a necessary task for many applications in the fields of molecular biology and biomedical diagnostics. Once released from the cells, the nucleic acid may be used for genetic analysis, e.g., sequencing, pathogen identification and quantification, nucleic acid mutation analysis, genome analysis, gene expression studies, pharmacological monitoring, storing of DNA libraries for drug discovery, etc. The genetic analysis typically involves nucleic acid amplification and detection using known techniques. For example, known polynucleotide amplification reactions include polymerase chain reaction (PCR), ligase chain reaction (LCR), QB replicase amplification (QBR), self-sustained sequence replication (3SR), strand-displacement amplification (SDA), "branched chain" DNA amplification, ligation activated transcription (LAT), nucleic acid sequence-based amplification (NASBA), repair chain reaction (RCR), and cycling probe reaction (CPR).

The extraction of nucleic acids from cells or viruses is generally performed by physical or chemical methods. Chemical methods typically employ lysing agents (e.g., detergents, enzymes, or strong organics) to disrupt the cells and release the nucleic acid, followed by treatment of the extract with chaotropic salts to denature any contaminating or potentially interfering proteins. Such chemical methods are described in U.S. Pat. No. 5,652,141 to Henco et al. and U.S. Pat. No. 5,856,174 to Lipshutz et al. One disadvantage to the use of harsh chemicals for disrupting cells is that the chemicals are inhibitory to subsequent amplification of the nucleic acid. In using chemical disruption methods, therefore, it is typically necessary to purify the nucleic acid released from the cells before proceeding with further analysis. Such purification steps are time consuming, expensive, and reduce the amount of nucleic acid recovered for analysis.

Physical methods for disrupting cells often do not require harsh chemicals that are inhibitory to nucleic acid amplification (e.g., PCR). These physical methods, however, also have their disadvantages. For example, one physical method for disrupting cells involves placing the cells in a solution and heating the solution to a boil to break open the cell walls. Unfortunately, the heat will often denature proteins and cause the proteins to stick to the released nucleic acid. The proteins then interfere with subsequent attempts to amplify the nucleic acid. Another physical method is freeze thawing in which the cells are repeatedly frozen and thawed until the cells walls are broken. Unfortunately, freeze thawing often fails to break open many structures, most notably certain spores and viruses that have extremely tough outer layers.

Another physical method for disrupting cells is the use of a pressure instrument. With this method, a solution of mycobacterial microorganisms is passed through a very small diameter hole under high pressure. During passage through the hole, the mycobacteria are broken open by the mechanical forces and their internal contents are spilled into solution. Such a system, however, is large, expensive and requires a cooling system to prevent excessive heat from building up and damaging the contents of the lysed cells. Moreover, the instrument needs to be cleaned and decontaminated between runs and a large containment system is required when infectious material is handled. A further disadvantage to this system is that the solution must contain only particles having substantially the same size, so that it may not be used to process many untreated clinical or biological specimens.

It is also known that cells can be lysed by subjecting the cells to ultrasonic agitation. Typically, the cells are disrupted by placing an ultrasonic probe directly into a volume of liquid containing the cells. Since the probe is in direct contact with a sample liquid, cross contamination and cavitation-induced foaming present serious complications.

Another method for cell disruption is disclosed by Murphy et al. in U.S. Pat. No. 5,374,522. According to the method, solutions or suspensions of cells are placed in a container with small beads. The container is then placed in an ultrasound bath until the cells disrupt, releasing their cellular components. This method has several disadvantages. First, the distribution of ultrasonic energy in the bath is not uniform, so that a technician must locate a high energy area within the bath and place the container into that area. The non-uniform distribution of ultrasonic energy also produces inconsistent results. Second, the ultrasound bath does not focus energy into the container so that the disruption of the cells often takes several minutes to complete, a relatively long period of time when compared to the method of the present invention. Third, it is not practical to carry an ultrasound bath into the field for use in biowarfare detection, forensic analysis, or on-site testing of environmental samples.

SUMMARY

The present invention overcomes the disadvantages of the prior art by providing an improved apparatus and method for disrupting cells or viruses. In contrast to the prior art methods described above, the present invention provides for the rapid and effective disruption of cells or viruses, including tough spores, without requiring the use of harsh chemicals. The disruption of the cells or viruses can often be completed in 5 to 10 seconds. In addition, the apparatus and method of the present invention provide for highly consistent and repeatable lysis of cells or viruses, so that consistent results are achieved from one use of the apparatus to the next.

According to a first embodiment, the apparatus comprises a container having a chamber for holding the cells or viruses. The container includes at least one flexible wall defining the chamber. The apparatus also includes a transducer, such as an ultrasonic horn, for impacting an external surface of the flexible wall to generate dynamic pressure pulses or pressure waves in the chamber. The apparatus also includes a pressure source for increasing the pressure in the chamber. The pressurization of the chamber ensures effective coupling between the transducer and the flexible wall. The apparatus may also include beads in the chamber for rupturing the cells or viruses.

In operation, the cells or viruses to be disrupted are placed in the chamber of the container. A liquid is also placed in the chamber. In one embodiment, the cells or viruses are placed in the chamber by capturing the cells or viruses on at least one filter positioned in the chamber. In this embodiment, the liquid placed in the chamber is usually a lysis buffer added to the chamber after the cells or viruses have been captured. In an alternative embodiment, the liquid placed in the chamber contains the cells or viruses to be disrupted (e.g., the liquid is a sample containing the cells or viruses) so that the liquid and cells are placed in the chamber simultaneously. In either embodiment, the transducer is placed against the external surface of the flexible wall, and the static pressure in the chamber is increased. Disruption of the cells is accomplished by impacting the flexible wall with the transducer to generate dynamic pressure pulses or pressure waves in the chamber. Beads may also be agitated in the chamber to rupture the cells or viruses.

A greater understanding of the invention may be gained by considering the following detailed description and the accompanying drawings.

BRIEF DESCRIPTION OF THE DRAWINGS

FIG. 20 also shows a pressure delivery nozzle sealed to a pressure port formed in the cartridge of FIG. 1.

DETAILED DESCRIPTION

The present invention provides an apparatus and method for analyzing a fluid sample. In a first embodiment, the invention provides a cartridge for separating a desired analyte from a fluid sample and for holding the analyte for a chemical reaction. The fluid sample may be a solution or suspension. In a particular use, the sample may be a bodily fluid (e.g., blood, urine, saliva, sputum, seminal fluid, spinal fluid, mucus, or other bodily fluids). Alternatively, the sample may be a solid made soluble or suspended in a liquid or the sample may be an environmental sample such as ground or waste water, soil extracts, pesticide residues, or airborne spores placed in a fluid. Further, the sample may be mixed with one or more chemicals, reagents, diluents, or buffers. The sample may be pretreated, for example, mixed with chemicals, centrifuged, pelleted, etc., or the sample may be in a raw form.

The desired analyte is typically intracellular material (e.g., nucleic acid, proteins, carbohydrates, lipids, bacteria, or intracellular parasites). In a preferred use, the analyte is nucleic acid which the cartridge separates from the fluid sample and holds for amplification (e.g., using PCR) and optical detection. As used herein, the term "nucleic acid" refers to any synthetic or naturally occurring nucleic acid, such as DNA or RNA, in any possible configuration, i.e., in the form of double-stranded nucleic acid, single-stranded nucleic acid, or any combination thereof.

Figure 1:
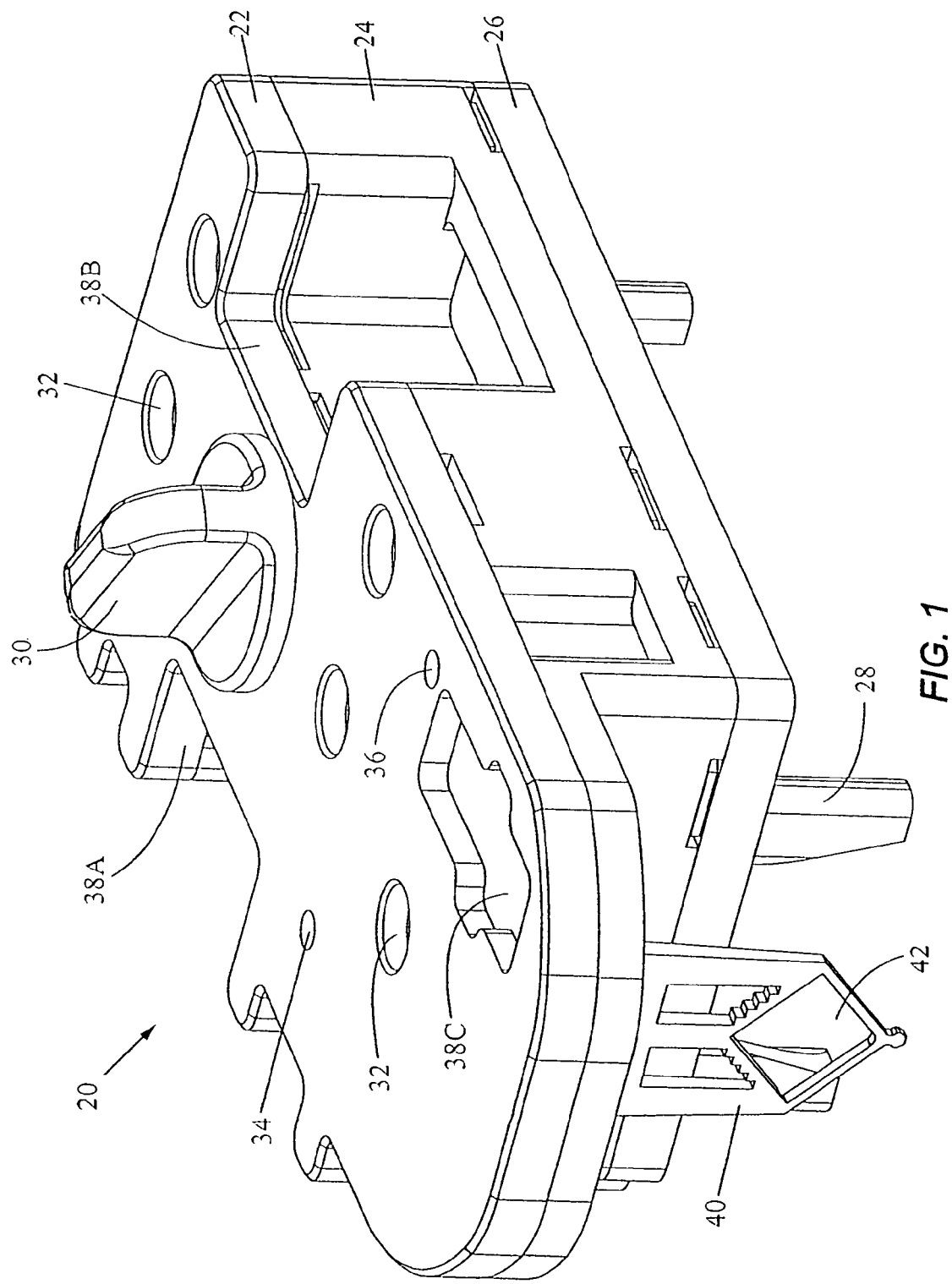
FIG. 1 is an isometric view of a cartridge for analyzing a fluid sample according to a first embodiment of the invention.

FIG. 1 shows an isometric view of a cartridge 20 according to the preferred embodiment. The cartridge 20 is designed to separate nucleic acid from a fluid sample and to hold the nucleic acid for amplification and detection. The cartridge 20 has a body comprising a top piece 22, a middle piece 24, and a bottom piece 26. An inlet port for introducing a fluid sample into the cartridge is formed in the top piece 22 and sealed by a cap 30. Six pressure ports 32 are also formed in the top piece 22. The pressure ports 32 are for receiving nozzles from pressure sources, e.g., pumps or vacuums. The cartridge also includes alignment legs 28 extending from the bottom piece 26 for positioning the cartridge 20 in an instrument (described below with reference to FIG. 10). Indentations or depressions 38A, 38B, and 38C are formed in the top and middle pieces 22, 24. The indentations are for receiving optical sensors that detect fluid flow in the cartridge 20. The cartridge 20 further includes vents 34, 36. Each pressure port and vent preferably includes a hydrophobic membrane that allows the passage of gas but not liquid into or out of the vents and pressure ports. Modified acrylic copolymer membranes are commercially available from, e.g., Gelman Sciences (Ann Arbor, Mich.) and particle-track etched polycarbonate membranes are available from Poretics, Inc. (Livermore, Calif.).

Figure 2:
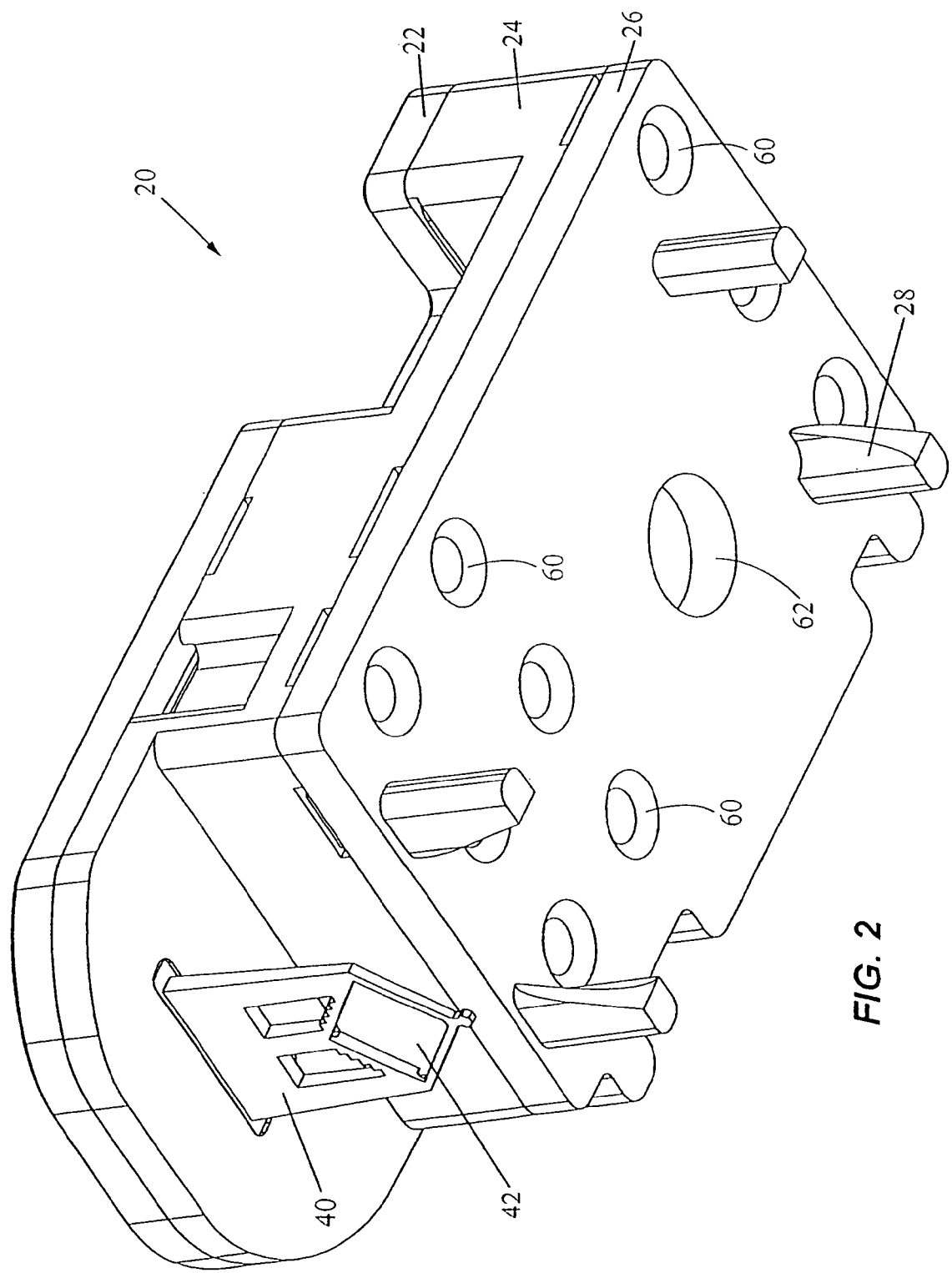
FIG. 2 is a lower isometric view of the cartridge of FIG. 1.

FIG. 2 is an isometric view showing the underside of the cartridge 20. Nine holes 60 are formed in the bottom piece 26 for receiving valve actuators that open and close valves in the cartridge 20. A hole 62 is also formed in the bottom piece 26 for receiving a transducer (described in detail below with reference to FIG. 5). The cartridge 20 also includes a reaction vessel 40 extending outwardly from the body of the cartridge. The vessel 40 has a reaction chamber 42 for holding a reaction mixture (e.g., nucleic acid mixed with amplification reagents and fluorescent probes) for chemical reaction and optical detection. One of the flow paths in the cartridge carries the reaction mixture to the chamber 42 for chemical reaction and optical detection. The vessel 40 extends outwardly from the body of the cartridge 20 so that the vessel 40 may be inserted between a pair of opposing thermal plates (for heating and cooling the chamber 42) without the need for decoupling the vessel 40 from the rest of the cartridge 20. This greatly reduces the risk of contamination and/or spilling. The vessel 40 may be integrally formed with the body of the cartridge (e.g., integrally molded with middle piece 24). It is presently preferred, however, to produce the vessel 40 as a separate element that is coupled to the body during manufacture of the cartridge.

Figure 3:
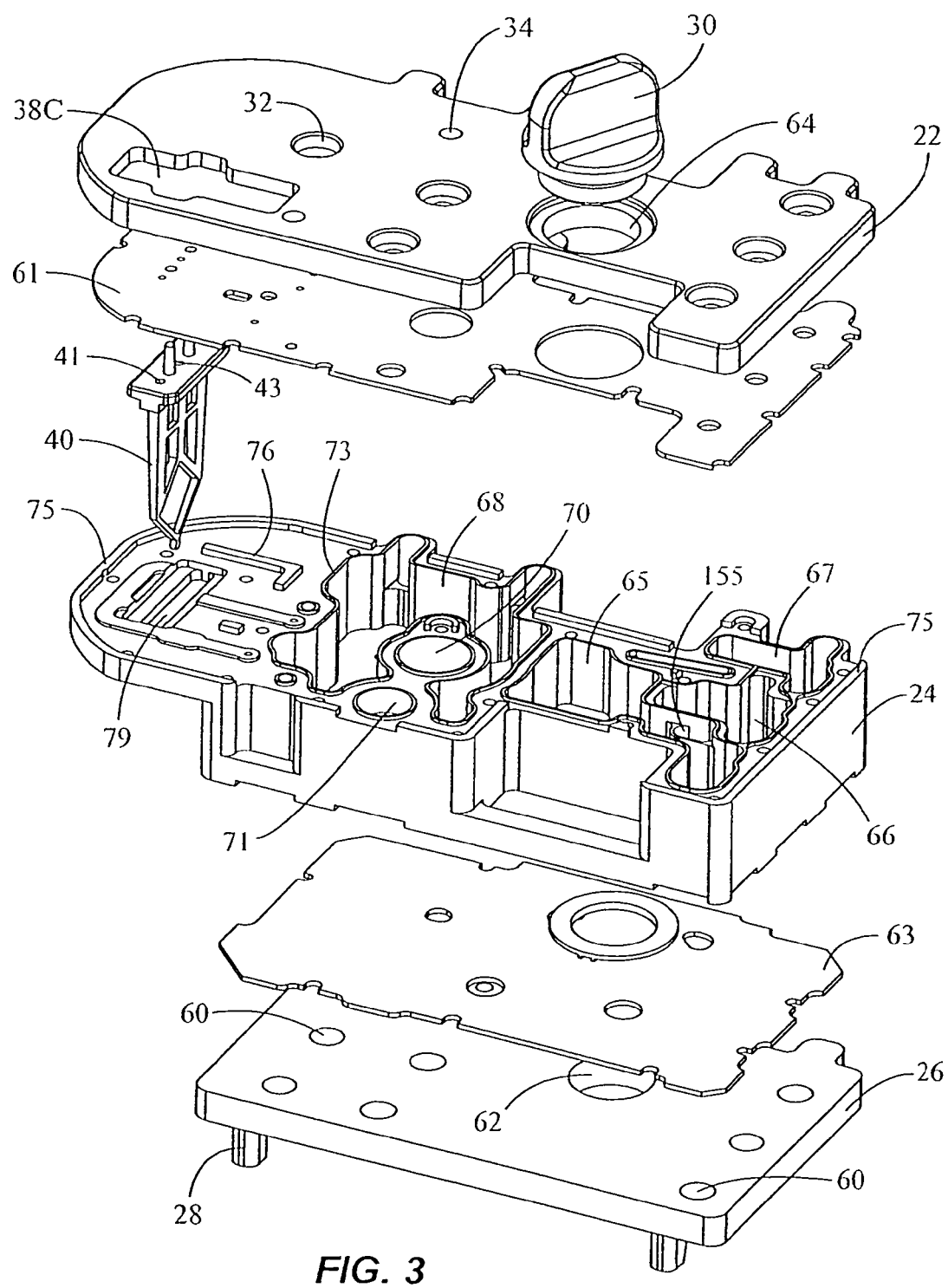
FIG. 3 is an exploded view of the cartridge of FIG. 1.
Figure 4:
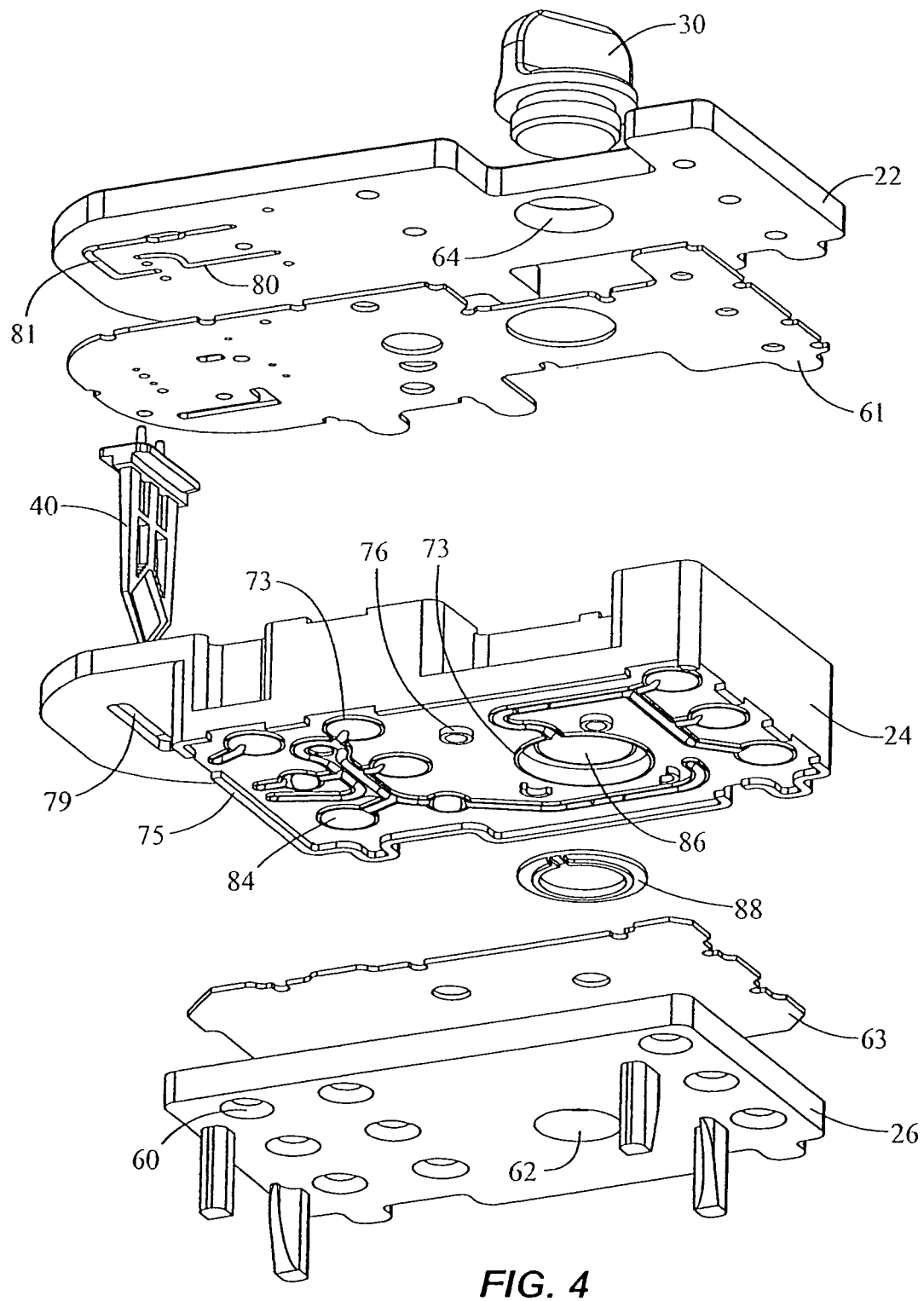
FIG. 4 is another exploded view of the cartridge of FIG. 1.

FIGS. 3-4 show exploded views of the cartridge. As shown in FIG. 3, the middle piece 24 has multiple chambers formed therein. In particular, the middle piece 24 includes a sample chamber 65 for holding a fluid sample introduced through the inlet port 64, a wash chamber 66 for holding a wash solution, a reagent chamber 67 for holding a lysing reagent, a waste chamber 68 for receiving used sample and wash solution, a neutralizer chamber 70 for holding a neutralizer, and a master mix chamber 71 for holding a master mix (e.g., amplification reagents and fluorescent probes) and for mixing the reagents and probes with analyte separated from the fluid sample. The sample chamber 65 optionally includes a side compartment 155 having slightly lower walls than the sample chamber 65. The side compartment 155 is for visually indicating to a user when sufficient sample has been added to the sample chamber 65, i.e., when the liquid level in the chamber 65 is high enough to spill over into the compartment 155.

The top piece 22 includes the vents 34, 36 and the six pressure ports 32, as previously described. An elastomeric membrane or gasket 61 is positioned and squeezed between the pieces 22, 24 to seal the various channels and chambers formed in the pieces. The middle piece 24 preferably includes multiple sealing lips to ensure that the gasket 61 forms an adequate seal. In particular, the middle piece 24 preferably includes sealing lips 73 surrounding each of the chambers 65, 66, 67, 68. 70, and 71. The middle piece 24 also includes support walls 75 around the perimeter, and intermediate sealing lips 76. The sealing lips 73, 76 and support walls 75 locally compress the gasket 61 and achieve a seal.

As shown in FIG. 4, the middle piece 24 has formed in its underside various channels, one of which leads to a lysing chamber 86. The chamber 86 is aligned with the hole 62 in the bottom piece 26 so that a transducer (e.g., an ultrasonic horn) may be inserted through the hole 62 to generate dynamic pressure pulses or pressure waves in the lysing chamber 86. The middle piece 24 also has nine valve seats 84 formed in its bottom surface. The valve seats 84 are aligned with the nine holes 60 in the bottom piece 26 so that valve actuators may be inserted through the holes 60 into the valve seats 84.

An elastomeric membrane or gasket 61 is positioned and squeezed between the pieces 24, 26 to seal the various channels, valve seats, and chamber formed in the middle piece 24. The middle piece 24 preferably includes multiple sealing lips to ensure that the gasket 63 forms an adequate seal. In particular, the middle piece 24 preferably includes sealing lips 73 surrounding the lysing chamber 86, valve seats 84, and various channels. The middle piece 24 also includes support walls 75 around its perimeter, and intermediate sealing lips 76. The sealing lips 73, 76 and support walls 75 locally compress the gasket 63 and achieve a seal. In addition to sealing various channels and chambers, the gasket 63 also functions as a valve stem by compressing, when actuated through one of the holes 60, into a corresponding valve seat 84, thus shutting one of the flow channels in the middle piece 24. This valve action is discussed in greater detail below with reference to FIGS. 15-16.

The gasket 63 also forms the bottom wall of the lysing chamber 86 against which a transducer is placed to effect disruption of cells or viruses in the chamber 86. Each of the gaskets 61, 63 is preferably composed of an elastomer. Suitable gasket materials are silicone rubber, neoprene, EPDM, or any other compliant material. Each of the gaskets 61, 63 preferably has a thickness in the range of 0.005 to 0.125 inches (0.125 to 3.175 mm), and more preferably in the range of 0.01 to 0.06 inches (0.25 to 1.5 mm), with a presently preferred thickness of 0.031 inches (0.79 mm). The thickness is selected to ensure that the gasket is sufficiently compliant to seal the channels and chambers, to compress into the valve seats 84 when forced, and to expand under pressure to contact the transducer.

As shown in FIG. 3, the middle piece 24 includes a slot 79 through which the reaction vessel 40 is inserted during assembly of the cartridge. The vessel 40 has two fluid ports 41, 43 for adding and removing fluid from the vessel. When the top piece 22 is sealed to the middle piece 24 via the gasket 61, the ports 41, 43 are placed into fluidic communication with channels 80, 81, respectively, that are formed in the top piece 22 (see FIG. 4). The gasket 61 seals the respective fluidic interfaces between the ports 41, 43 and the channels 80, 81. The top, middle, and bottom pieces 22, 24, 26 are preferably injection molded parts made of a polymeric material such as polypropylene, polycarbonate, or acrylic. Although molding is preferred for mass production, it also possible to machine the top, middle, and bottom pieces 22, 24, 26. The pieces 22, 24, 26 may be held together by screws or fasteners. Alternatively, ultrasonic bonding, solvent bonding, or snap fit designs could be used to assemble the cartridge.

Figure 6:
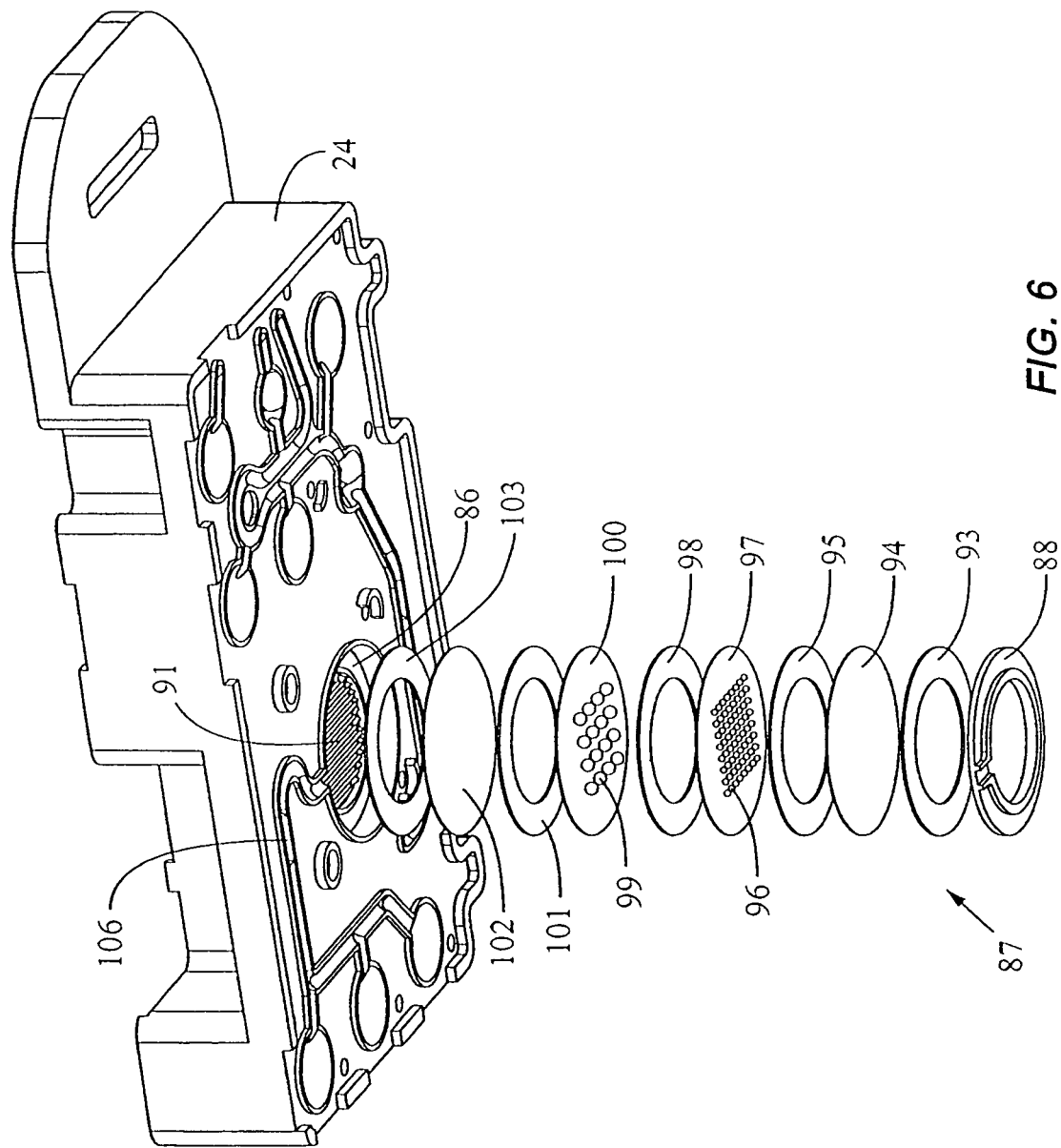
FIG. 6 is an exploded view of a filter stack positioned in the lysing chamber of the cartridge of FIG. 1.

FIG. 4 also shows a filter ring 88. The filter ring 88 compresses and holds a stack of filters in the lysing chamber 86. FIG. 6 shows an exploded view of a filter stack 87. The purpose of the filter stack 87 is to capture cells or viruses from a fluid sample as the sample flows through the lysing chamber 86. The captured cells or viruses are then disrupted (lysed) in the chamber 86. The cells may be animal or plant cells, spores, bacteria, or microorganisms. The viruses may be any type of infective agents having a protein coat surrounding an RNA or DNA core.

The filter stack 87 comprises a gasket 93, a first filter 94, a gasket 95, a second filter 97 having a smaller pore size than the first filter 94, a gasket 98, a third filter 100 having a smaller pore size than the second filter 97, a gasket 101, a woven mesh 102, and a gasket 103. The filter stack also preferably includes a first set of beads 96 disposed between the first and second filters 94 and 97 and a second set of beads 99 disposed between the second and third filters 97 and 100. The filter ring 88 compresses the filter stack 87 into the lysing chamber 86 so that the gasket 93 is pressed against the filter 94, the filter 94 is pressed against the gasket 95, the gasket 95 is pressed against the filter 97, the filter 97 is pressed against the gasket 98, the gasket 98 is pressed against the filter 100, the filter 100 is pressed against the gasket 101, the gasket 101 is pressed against the mesh 102, the mesh 102 is pressed against the gasket 103, and the gasket 103 is pressed against the outer perimeter of the bottom wall of the lysing chamber 86. The gasket 95 is thicker than the average diameter of the beads 96 so that the beads are free to move in the space between the filters 94 and 97. Similarly, the gasket 98 is thicker than the average diameter of the beads 99 so that the beads 99 are free to move in the space between the filters 97 and 100. A fluid sample flowing through the channel 106 into the lysing chamber 86 first flows through filter 94, then through filter 97, next through filter 100, and lastly through the mesh 102. After flowing through the filter stack 87, the sample flows along flow ribs 91 formed in the top of the lysing chamber 86 and through an outlet channel (not shown in FIG. 6).

Figure 5:
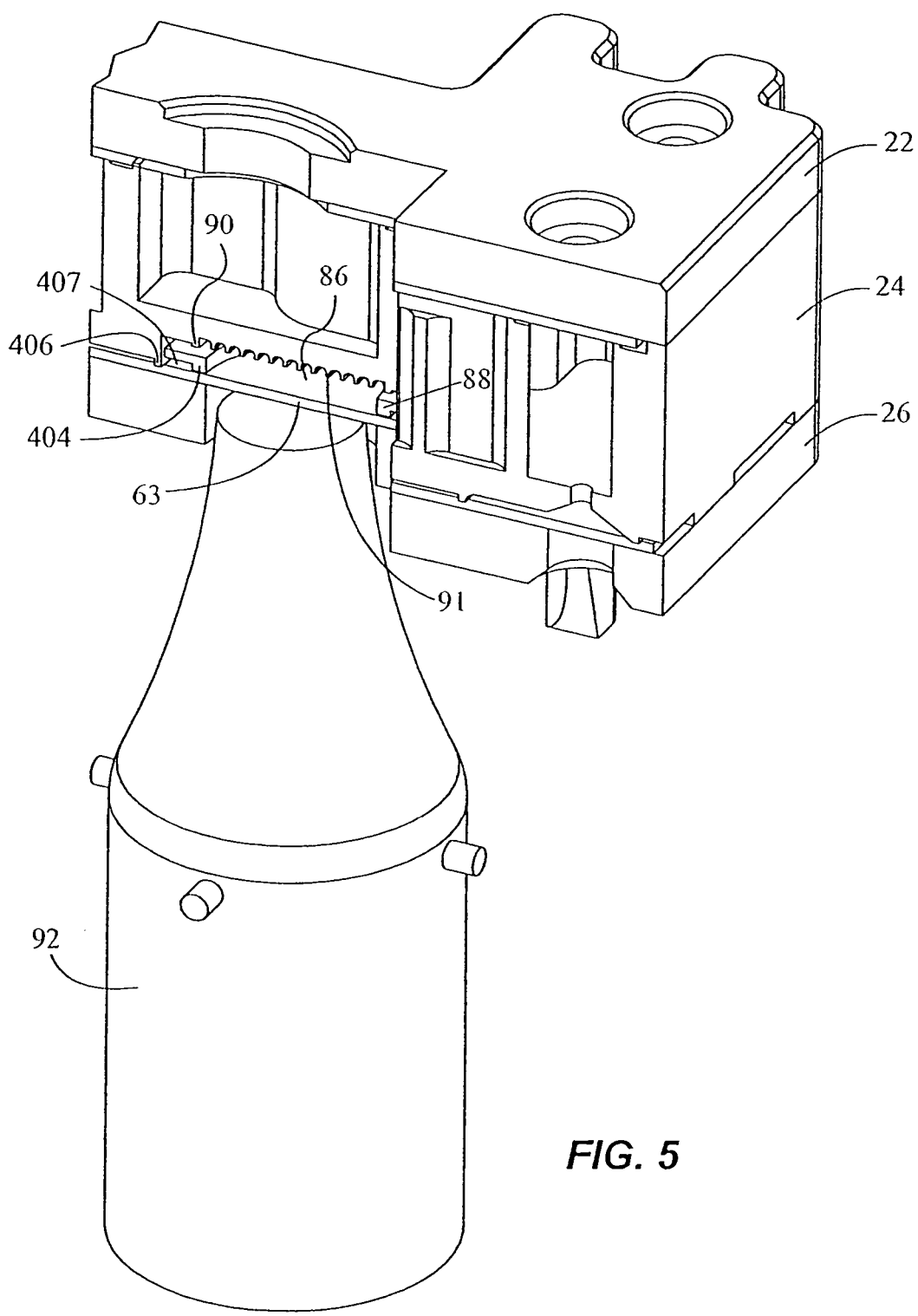
FIG. 5 is a partially cut away view of an ultrasonic horn coupled to a wall of a lysing chamber formed in the cartridge of FIG. 1.

Referring to FIG. 5, the cells or viruses captured in the filter stack (not shown in FIG. 5 for illustrative clarity) are lysed by coupling a transducer 92 (e.g., an ultrasonic horn) directly to the wall of the lysing chamber 86. In this embodiment, the wall of the lysing chamber 86 is formed by the flexible gasket 63. The transducer 92 should directly contact an external surface of the wall. The term "external surface" is intended to mean a surface of the wall that is external to the lysing chamber 86. The transducer 92 is a vibrating or oscillating device that is activated to generate dynamic pressure pulses or pressure waves in the chamber 86. The pressure waves agitate the beads 96, 99 (FIG. 6), and the movement of the beads ruptures the captured cells or viruses. In general, the transducer for contacting the wall of the lysing chamber 86 may be an ultrasonic, piezoelectric, magnetostrictive, or electrostatic transducer. The transducer may also be an electromagnetic device having a wound coil, such as a voice coil motor or a solenoid device. It is presently preferred that the actuator be an ultrasonic transducer, such as an ultrasonic horn. Suitable horns are commercially available from Sonics & Materials, Inc. having an office at 53 Church Hill, Newton, Conn. 06470-1614 USA. Alternatively, the ultrasonic transducer may comprise a piezoelectric disk or any other type of ultrasonic transducer that may be coupled to the container. It is presently preferred to use an ultrasonic horn because the horn structure is highly resonant and provides for repeatable and sharp frequency of excitation and large motion of the horn tip.

As previously described in FIG. 6, the filter stack includes a gasket at both of its ends. As shown in FIG. 5, the middle cartridge piece 24 has a sealing lip 90 against which the gasket at one end of the filter stack is compressed. The gasket at the other end of the filter stack is compressed by the filter ring 88 to form a seal. The gasket material may expand into the relief area outside of the sealing lip 90. The width of the sealing lip 90 is small (typically 0.5 mm) so that an excessive amount of force is not required to achieve a sufficient seal.

The filter ring 88 is held between the filter stack and the cartridge gasket 63. The cartridge gasket 63 is held between the middle piece 24 and the bottom piece 26 by a sealing lip 406. Force is therefore transferred from the bottom piece 26 through the gasket 63 to the filter ring 88 and finally to the filter stack. The filter ring 88 contains a contact lip 404 that contacts the gasket 63. The contact lip 404 is not a primary sealing lip (though it will seal) but a force transfer mechanism. The width of the contact lip 404 is larger than the width of the sealing lip 90 to ensure that deformation and sealing action occurs in the filter stack and not taken up in squeezing the cartridge gasket 63. The cartridge middle piece 24 also has a sealing lip 406 that surrounds the filter ring 88. This is an active sealing area that should not be compromised by the presence of the filter ring 88. For this reason, there is a gap 407 between the sealing lip 406 and the contact lip 404 on the filter ring 88. The gap 407 is provided to allow the gasket 63 to extrude into the gap 407 as it is compressed by the sealing lip 406 and the contact lip 404. If the contact lip 404 comes to a different elevation than the sealing lip 406, the seal will not be compromised because of the gap 407 and the distance between the lips 404 and 406.

Referring again to FIG. 6, the filter stack 87 is effective for capturing cells or viruses as a fluid sample flows through the stack 87 without clogging of any of the filters 94, 97, 100 in the stack. The first filter 94 (having the largest pore size) filters out coarse material such as salt crystals, cellular debris, hair, tissue, etc. The second filter 97 (having the medium pore size) captures cells or viruses in the fluid sample. The third filter 100 (having the smallest pore size) captures smaller cells or viruses in the sample. The filter stack 87 thus enables the simultaneous capture of differently sized sample components without clogging of the filters. The average pore size of the first filter 94 is selected to be small enough to filter coarse material from the fluid sample (e.g., salt crystals, cellular debris, hair, tissue) yet large enough to allow the passage of the target cells or viruses containing the desired analyte (e.g., nucleic acid or proteins). In general, the pore size of the first filter 94 should be in the range of about 2 to 25 μm, with a presently preferred pore size of about 5 μm.

The average pore sizes of the second and third filters are selected in dependence upon the average size of the target cells or viruses that contain the desired analyte(s). For example, in one embodiment, the filter stack 87 is used to capture gonorrhea (GC) and chlamydia (Ct) organisms to determine the presence of the diseases in the fluid sample. The GC and Ct organisms have different average diameters, about 1 to 2 μm for GC organisms and about 0.3 μm for Ct organisms. In this embodiment, the second filter 97 has an average pore size of about 1.2 μm while the third filter 100 has an average pore size of about 0.22 μm so that most of the GC organisms are captured by the second filter 97 while most of the Ct organisms are captured by the third filter 100. The filter stack thus enables the simultaneous capture of differently sized target organisms and does so without clogging of the filters. The pore sizes of the filters 97, 100 may be selected to capture desired cells or viruses of any size, and the scope of the invention is not limited to the specific example given.

The filter stack 87 is also useful for disrupting the captured cells or viruses to release the intracellular material (e.g., nucleic acid) therefrom. The first and second sets of beads 96, 99 serve two useful purposes in this regard. First, the beads are agitated by dynamic pressure pulses or pressure waves generated by the transducer. The movement of the beads ruptures the captured cells or viruses. Second, the beads may shear the nucleic acid released from the lysed cells or viruses so that the strands of nucleic acid are sufficiently short to flow through the filters and out of the lysing chamber 86. Suitable beads for rupturing cells or viruses include borosilicate glass, lime glass, silica, and polystyrene beads.

The beads may be porous or non-porous and preferably have an average diameter in the range of 1 to 200 μm. The average diameter of the beads 96, 99 is selected in dependence upon the intended target cells or viruses to be ruptured by the beads. The average diameter of the beads 96 in the first set may be equal to the average diameter of the beads 99 in the second set. Alternatively, when the first set of beads 96 is used to rupture a type of target cell or virus that differs from the type of cell or virus to be ruptured by the second set of beads 99, it is advantageous to select the average diameter of the beads such that the average diameter of the beads 96 in the first set differs from the average diameter of the beads 99 in the second set. For example, when the filter stack is used to capture GC and Ct cells as described above, the beads 96 are 20 μm diameter borosilicate glass beads for rupturing the GC organisms and the beads 99 are 106 μm diameter soda lime glass beads for rupturing the Ct organisms. Each of the silicone gaskets 95, 98 should be sufficiently thick to allow room for the beads 96, 99 to move and rupture the cells or viruses.

The mesh 102 also serves two useful purposes. First the mesh provides support to the filter stack 87. Second, the mesh breaks up air bubbles so that the bubbles can be channeled through the flow ribs 91 and out of the lysing chamber 86. To effectively break up or reduce the size of the air bubbles, the mesh 102 preferably has a small pore size. Preferably, it is a woven polypropylene mesh having an average pore size of about 25 μm. To ensure that the air bubbles can escape from the lysing chamber 86, it is desirable to use the cartridge in an orientation in which liquid flows up (relative to gravity) through the filter stack 87 and the lysing chamber 86. The upward flow through the chamber 86 aids the flow of air bubbles out of the chamber 86. Thus, the inlet port for entry of fluids into the chamber 86 should generally be at the lowest point in the chamber, while the exit port should be at the highest.

Many different embodiments of the filter stack are possible. For example, in one alternative embodiment, the filter stack has only two filters and one set of beads disposed between the filters. The first filter has the largest pore size (e.g., 5 μm) and filters out coarse material such as salt crystals, cellular debris, hair, tissue, etc. The second filter has a pore size smaller than the first filter and slightly smaller than the target cells or viruses to be captured. Such a filter stack is described below with reference to FIG. 38. In another embodiment of the cartridge, the filter having the largest pore size (for filtering the coarse material) is positioned in a filter chamber (not shown) that is positioned upstream of the lysing chamber 86. A channel connects to the filter chamber to the lysing chamber 86. In this embodiment, a fluid sample flows first through the coarse filter in the filter chamber and then through a second filter in the lysing chamber to trap the target cells or viruses in the lysing chamber.

Further, the beads in the filter stack may have a binding affinity for target cells or viruses in the fluid sample to facilitate capture of the target cells or viruses. For example, antibodies or certain receptors may be coated onto the surface of the beads to bind target cells in the sample. Moreover, the lysing chamber 86 may contain two different types of beads for interacting with target cells or viruses. For example, the lysing chamber may contain a first set of beads coated with antibodies or receptors for binding target cells or viruses and a second set of beads (intermixed with the first set) for rupturing the captured cells or viruses. The beads in the lysing chamber 86 may also have a binding affinity for the intracellular material (e.g., nucleic acid) released from the ruptured cells or viruses. Such beads are useful for isolating target nucleic acid for subsequent elution and analysis. For example, the lysing chamber may contain silica beads to isolate DNA or cellulose beads with oligo dT to isolate messenger RNA for RT-PCR. The lysing chamber 86 may also contain beads for removing unwanted material (e.g., proteins, peptides) or chemicals (e.g., salts, metal ions, or detergents) from the sample that might inhibit PCR. For example, the chamber 86 may contain ion exchange beads for removing proteins. Alternatively beads having metal ion chelators such as iminodiacetic acid will remove metal ions from biological samples.

Figure 21:
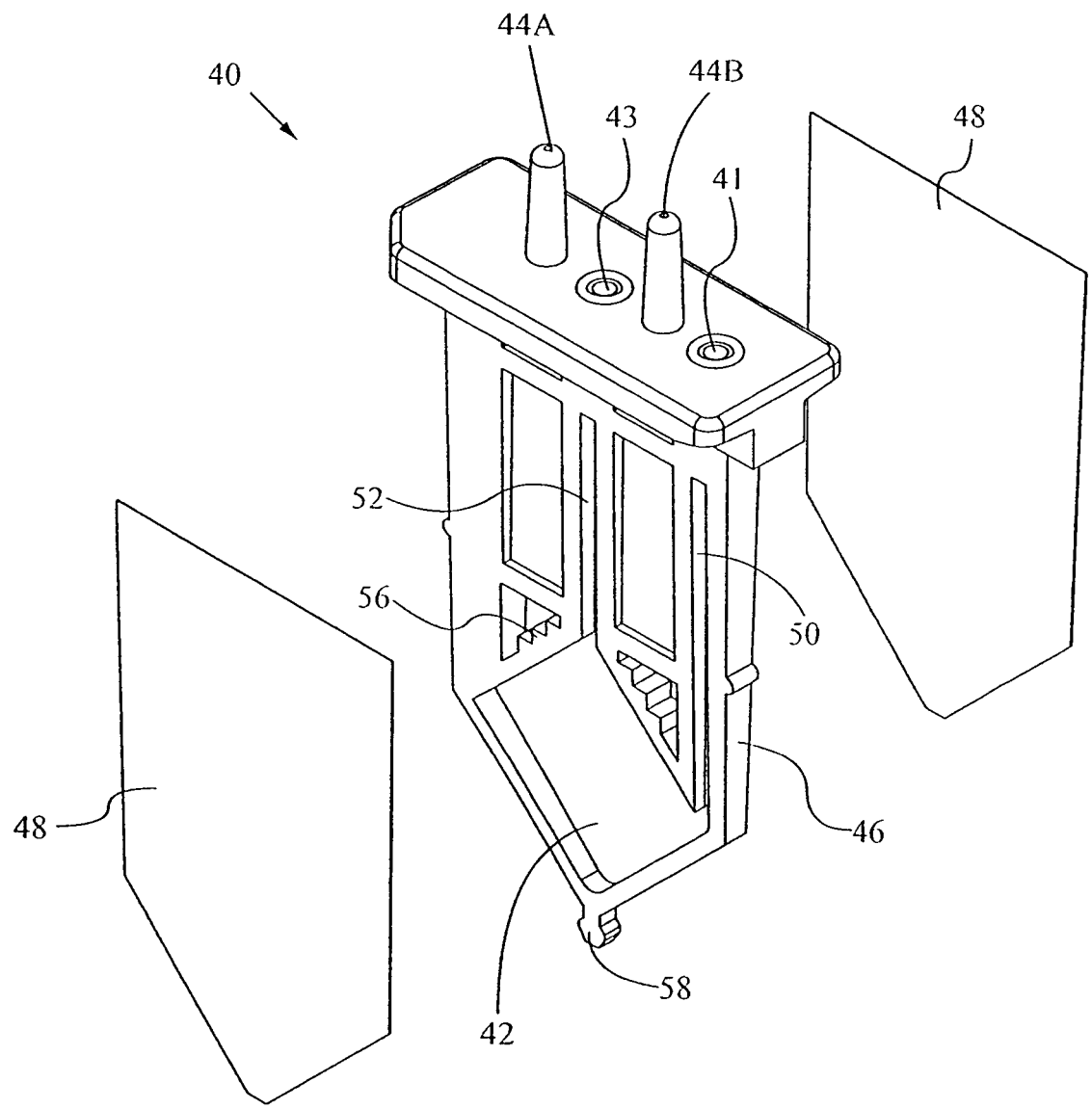
FIG. 21 is a partially exploded, isometric view of a reaction vessel of the cartridge of FIG. 1.
Figure 22:
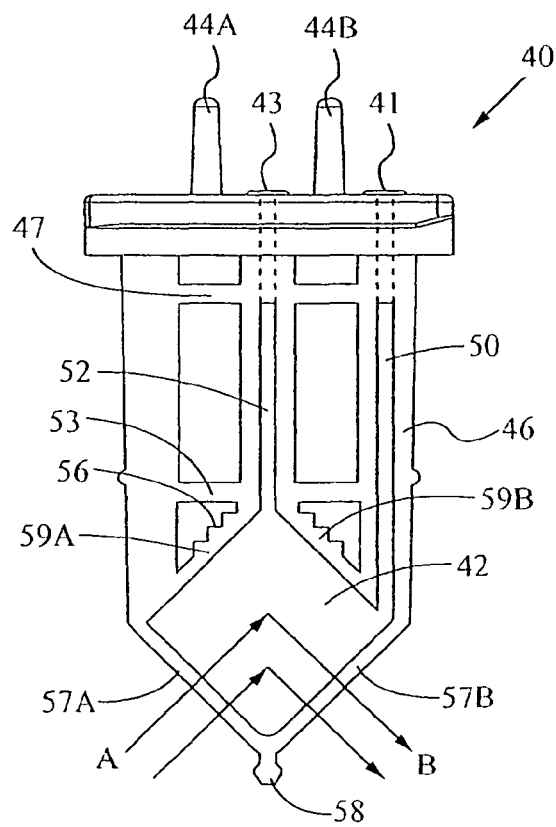
FIG. 22 is a front view of the vessel of FIG. 21.

FIGS. 21-22 illustrate the reaction vessel 40 in greater detail. FIG. 21 shows a partially exploded view of the vessel 40, and FIG. 22 shows a front view of the vessel 40. The vessel 40 includes the reaction chamber 42 (diamond-shaped in this embodiment) for holding a reaction mixture. The vessel 40 is designed for optimal heat transfer to and from the reaction mixture and for efficient optical viewing of the mixture. The thin shape of the vessel contributes to optimal thermal kinetics by providing large surfaces for thermal conduction and for contacting thermal plates. In addition, the walls of the vessel provide optical windows into the chamber 42 so that the entire reaction mixture can be optically interrogated. In more detail to FIGS. 21-22, the reaction vessel 40 includes a rigid frame 46 that defines the side walls 57A, 57B, 59A, 59B of the reaction chamber 42. The frame 46 also defines an inlet port 41 and a channel 50 connecting the port 41 to the chamber 42. The frame 46 also defines an outlet port 43 and a channel 52 connecting the port 43 to the chamber 42. The inlet port 41 and channel 50 are used to add fluid to the chamber 42, and the channel 52 and outlet port 43 are used for exit of fluid from the chamber 42. Alignment prongs 44A, 44B are used to position the vessel 40 correctly during assembly of the cartridge.

As shown in FIG. 21, the vessel 40 also includes thin, flexible sheets attached to opposite sides of the rigid frame 46 to form opposing major walls 48 of the chamber. (The major walls 48 are shown in FIG. 1 exploded from the rigid frame 46 for illustrative clarity). The reaction chamber 42 is thus defined by the rigid side walls 57A, 57B, 59A, 59B of the frame 46 and by the opposing major walls 48. The opposing major walls 48 are sealed to opposite sides of the frame 46 such that the side walls 57A, 57B, 59A, 59B connect the major walls 48 to each other. The walls 48 facilitate optimal thermal conductance to the reaction mixture contained in the chamber 42. Each of the walls 48 is sufficiently flexible to contact and conform to a respective thermal surface, thus providing for optimal thermal contact and heat transfer between the thermal surface and the reaction mixture contained in the chamber 42. Furthermore, the flexible walls 48 continue to conform to the thermal surfaces if the shape of the surfaces changes due to thermal expansion or contraction during the course of the heat-exchanging operation.

Figure 23:
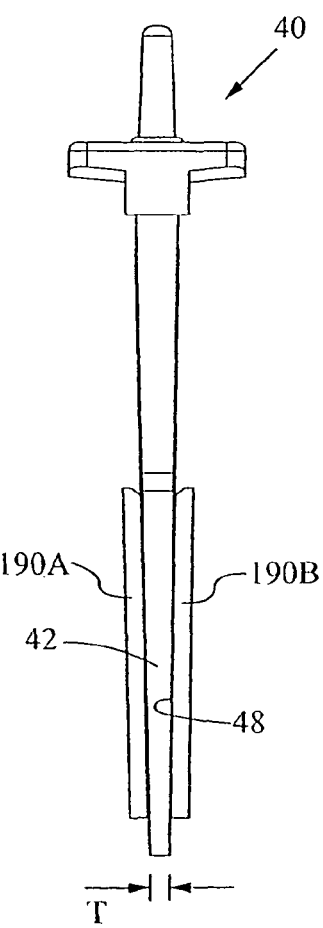
FIG. 23 is a side view of the vessel of FIG. 21 inserted between two heater plates.

As shown in FIG. 23, the thermal surfaces for contacting the flexible walls 48 are preferably formed by a pair of opposing plates 190A, 190B positioned to receive the chamber 42 between them. When the chamber 42 of the vessel 40 is inserted between the plates 190A, 190B, the inner surfaces of the plates contact the walls 48 and the flexible walls conform to the surfaces of the plates. The plates are preferably spaced a distance from each other equal to the thickness T of the chamber 42 as defined by the thickness of the frame 46. In this position, minimal or no gaps are found between the plate surfaces and the walls 48. The plates may be heated and cooled by various thermal elements to induce temperature changes within the chamber 42, as is described in greater detail below.

The walls 48 are preferably flexible films of polymeric material such as polypropylene, polyethylene, polyester, or other polymers. The films may either be layered, e.g., laminates, or the films may be homogeneous. Layered films are preferred because they generally have better strength and structural integrity than homogeneous films. In particular, layered polypropylene films are presently preferred because polypropylene is not inhibitory to PCR. Alternatively, the walls 48 may comprise any other material that may be formed into a thin, flexible sheet and that permits rapid heat transfer. For good thermal conductance, the thickness of each wall 48 is preferably between about 0.003 to 0.5 mm, more preferably between 0.01 to 0.15 mm, and most preferably between 0.025 to 0.08 mm.

Referring again to FIG. 22, the vessel 40 also preferably includes optical windows for in situ optical interrogation of the reaction mixture in the chamber 42. In the preferred embodiment, the optical windows are the side walls 57A, 57B of the rigid frame 46. The side walls 57A, 57B are optically transmissive to permit excitation of the reaction mixture in the chamber 42 through the side wall 57A and detection of light emitted from the chamber 42 through the side wall 57B. Arrows A represent illumination beams entering the chamber 42 through the side wall 57A and arrows B represent emitted light (e.g., fluorescent emission from labeled analytes in the reaction mixture) exiting the chamber 42 through the side wall 57B.

The side walls 57A, 57B are preferably angularly offset from each other. It is usually preferred that the walls 57A, 57B are offset from each other by an angle of about 90°. A 90° angle between excitation and detection paths assures that a minimum amount of excitation radiation entering through the wall 57A will exit through wall 57B. In addition, the 90° angle permits a maximum amount of emitted light (e.g. fluorescence) to be collected through wall 57B. The walls 57A, 57B are preferably joined to each other to form a "V" shaped intersection at the bottom of the chamber 42. Alternatively, the angled walls 57A, 57B need not be directly joined to each other, but may be separated by an intermediary portion, such as another wall or various mechanical or fluidic features which do not interfere with the thermal and optical performance of the vessel. For example, the walls 57A, 57B may meet at a port which leads to another processing area in communication with the chamber 42, such as an integrated capillary electrophoresis area. In the presently preferred embodiment, a locating tab 58 extends from the frame 46 below the intersection of walls 57A, 57B.

The tab 58 is used to properly position the vessel 40 in a heat-exchanging module described below with reference to FIG. 28.

Optimum optical sensitivity may be attained by maximizing the optical path length of the light beams exciting the labeled analyte in the reaction mixture and the emitted light that is detected, as represented by the equation:

$$I_o/I_i = C * L * A,$$

where $I_o$ is the illumination output of the emitted light in volts, photons or the like, C is the concentration of analyte to be detected, It is the input illumination, L is the path length, and A is the intrinsic absorptivity of the dye used to label the analyte.

Figures 26, 27:
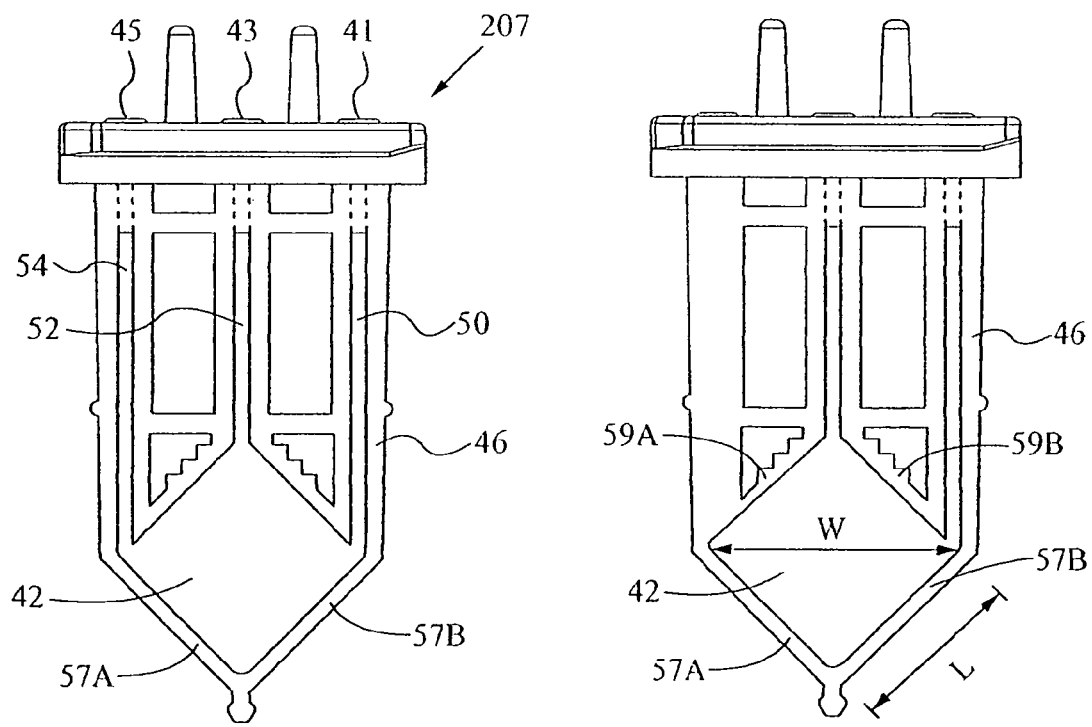
FIG. 26 is a front view of another reaction vessel according to the present invention.
FIG. 27 is another front view of the vessel of FIG. 21.

The thin, flat reaction vessel 40 of the present invention optimizes detection sensitivity by providing maximum optical path length per unit analyte volume. Referring to FIGS. 23 and 27, the vessel 40 is preferably constructed such that each of the sides walls 57A, 57B, 59A, 59B of the chamber 42 has a length L in the range of 1 to 15 mm, the chamber has a width W in the range of 1.4 to 20 mm, the chamber has a thickness T in the range of 0.5 to 5 mm, and the ratio of the width W of the chamber to the thickness T of the chamber is at least 2:1. These parameters are presently preferred to provide a vessel having a relatively large average optical path length through the chamber, i.e. 1 to 15 mm on average, while still keeping the chamber sufficiently thin to allow for extremely rapid heating and cooling of the reaction mixture contained therein. The average optical path length of the chamber 42 is the distance from the center of the side wall 57A to the center of the chamber 42 plus the distance from the center of the chamber 42 to the center of the side wall 57B.

More preferably, the vessel 40 is constructed such that each of the sides walls 57A, 57B, 59A, 59B of the chamber 42 has a length L in the range of 5 to 12 mm, the chamber has a width W in the range of 7 to 17 mm, the chamber has a thickness T in the range of 0.5 to 2 mm, and the ratio of the width W of the chamber to the thickness T of the chamber is at least 4:1. These ranges are more preferable because they provide a vessel having both a larger average optical path length (i.e., 5 to 12 mm) and a volume capacity in the range of 12 to 100 µl while still maintaining a chamber sufficiently thin to permit extremely rapid heating and cooling of a reaction mixture. The relatively large volume capacity provides for increased sensitivity in the detection of low concentration analytes, such as nucleic acids.

In the preferred embodiment, the reaction vessel 40 has a diamond-shaped chamber 42 defined by the side walls 57A, 57B, 59A, 59B, each of the side walls has a length of about 10 mm, the chamber has a width of about 14 mm, the chamber has a thickness T of 1 mm as defined by the thickness of the frame 46, and the chamber has a volume capacity of about 100

μl. This reaction vessel provides a relatively large average optical path length of 10 mm through the chamber 42. Additionally, the thin chamber allows for extremely rapid heating and/or cooling of the reaction mixture contained therein. The diamond-shape of the chamber 42 helps prevent air bubbles from forming in the chamber as it is filled with the reaction mixture and also aids in optical interrogation of the mixture.

Referring again to FIG. 22, the frame 46 is preferably made of an optically transmissive material, e.g., a polycarbonate or clarified polypropylene, so that the side walls 57A, 57B are optically transmissive. As used herein, the term optically transmissive means that one or more wavelengths of light may be transmitted through the walls. In the preferred embodiment, the optically transmissive walls 57A, 57B are substantially transparent. In addition, one or more optical elements may be present on the optically transmissive side walls 57A, 57B. The optical elements may be designed, for example, to maximize the total volume of solution which is illuminated by a light source, to focus excitation light on a specific region of the chamber 42, or to collect as much fluorescence signal from as large a fraction of the chamber volume as possible. In alternative embodiments, the optical elements may comprise gratings for selecting specific wavelengths, filters for allowing only certain wavelengths to pass, or colored lenses to provide filtering functions. The wall surfaces may be coated or comprise materials such as liquid crystal for augmenting the absorption of certain wavelengths. In the presently preferred embodiment, the optically transmissive walls 57A, 57B are substantially clear, flat windows having a thickness of about 1 mm.

The side walls 59A, 59B preferably includes reflective faces 56 which internally reflect light trying to exit the chamber 42 through the side walls 59A, 59B. The reflective faces 56 are arranged such that adjacent faces are angularly offset from each other by about 90°. In addition, the frame 46 defines open spaces between the side walls 59A, 59B and the support ribs 53. The open spaces are occupied by ambient air that has a different refractive index than the material composing the frame (e.g., plastic). Due to the difference in the refractive indexes, the reflective faces 56 are effective for internally reflecting light trying to exit the chamber through the walls 59A, 59B and provide for increased detection of optical signal through the walls 57A, 57B. Preferably, the optically transmissive side walls 57A, 57B define the bottom portion of the diamond-shaped chamber 42, and the retro-reflective side walls 59A, 59B define the top portion of the chamber.

A preferred method for fabricating the reaction vessel 40 will now be described with reference to FIGS. 21-22. The reaction vessel 40 may be fabricated by first molding the rigid frame 46 using known injection molding techniques. The frame 46 is preferably molded as a single piece of polymeric material, e.g., clarified polypropylene. After the frame 46 is produced, thin, flexible sheets are cut to size and sealed to opposite sides of the frame 46 to form the major walls 48 of the chamber 42. The major walls 48 are preferably cast or extruded films of polymeric material, e.g., polypropylene films, that are cut to size and attached to the frame 46 using the following procedure. A first piece of film is placed over one side of the frame 46. The frame 46 preferably includes a tack bar 47 for aligning the top edge of the film. The film is placed over the bottom portion of the frame 46 such that the top edge of the film is aligned with the tack bar 47 and such that the film completely covers the bottom portion of the frame 46 below the tack bar 47. The film should be larger than the bottom portion of the frame 46 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 46, preferably by heat sealing. Heat sealing is presently preferred because it produces a strong seal without introducing potential contaminants to the vessel as the use of adhesive or solvent bonding techniques might do. Heat sealing is also simple and inexpensive. The heat sealing may be performed using, e.g., a heated platen. An identical procedure may be used to cut and seal a second sheet to the opposite side of the frame 46 to complete the chamber 42. Many variations to this fabrication procedure are possible. For example, in an alternative embodiment, the film is stretched across the bottom portion of the frame 46 and then sealed to the frame prior to cutting the film to size. After sealing the film to the frame, the portions of the film that extend past the perimeter of the frame are cut away using, e.g., a laser or die.

Although it is presently preferred to mold the frame 46 as a single piece, it is also possible to fabricate the frame from multiple pieces. For example, the side walls 57A, 57B forming the angled optical windows may be molded from polycarbonate, which has good optical transparency, while the rest of the frame is molded from polypropylene, which is inexpensive and compatible with PCR. The separate pieces can be attached together in a secondary step. For example, the side walls 57A, 57B may be press-fitted and/or bonded to the remaining portion of the frame 46. The flexible walls 48 may then be attached to opposite sides of the frame 46 as previously described.

Referring again to FIG. 3, it is presently preferred to use a gasket 61 to seal the ports 41, 43 of the vessel 40 to corresponding channels 80, 81 (FIG. 4) in the cartridge body. Alternatively, fluidic seals may be established using a luer fitting, compression fitting, or swaged fitting. In another embodiment, the cartridge body and frame of the vessel 40 are molded as a single part, and the flexible major walls of the vessel are heat-sealed to opposite sides of the frame.

Referring again to FIG. 22, the chamber 42 is filled by forcing liquid (e.g., a reaction mixture) to flow through the port 41 and the channel 50 into the chamber 42. The liquid may be forced to flow into the chamber 42 using differential pressure (i.e., either pushing the liquid through the inlet port 41 or aspirating the liquid by applying a vacuum to the outlet port 43). As the liquid fills the chamber 42, it displaces air in the chamber. The displaced air exits the chamber 42 through the channel 52 and the port 43. For optimal detection of analyte in the chamber 42, the chamber should not contain air bubbles. To help prevent the trapping of air bubbles in the chamber 42, the connection between the chamber 42 and the outlet channel 52 should be at the highest point (with respect to gravity) in the chamber 42. This allows air bubbles in the chamber 42 to escape without being trapped. Thus, the vessel 40 is designed to be used in the vertical orientation shown in FIG. 22.

Figure 25:
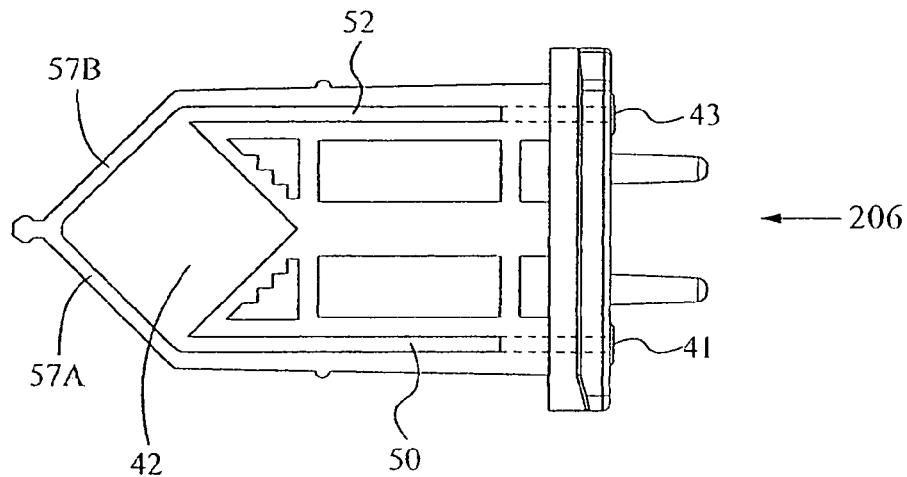
FIG. 25 is a front view of an alternative reaction vessel according to the present invention.

FIG. 25 shows another vessel 206 designed to be used in a horizontal orientation. The vessel 206 has an inlet port 41 and an inlet channel 50 connecting the inlet port 41 to the bottom of the chamber 42. The vessel also has an outlet port 43 and an outlet channel 50 connecting the outlet port 43 to the top of the chamber 42. Thus, any air bubbles in the chamber 42 may escape through the outlet channel 52 without becoming trapped. FIG. 26 shows another vessel 207 having two inlet ports 41, 45 and one outlet port 43. Inlet channels 50, 54 connect the respective inlet ports 41, 45 to the chamber 42, and outlet channel 52 connects the chamber 42 to outlet port 43. Many other different embodiments of the vessel are also possible. In each embodiment, it is desirable to evacuate the chamber 42 from the highest point (with respect to gravity) in the chamber and to introduce liquid into the chamber from a lower point.

Figure 15A:
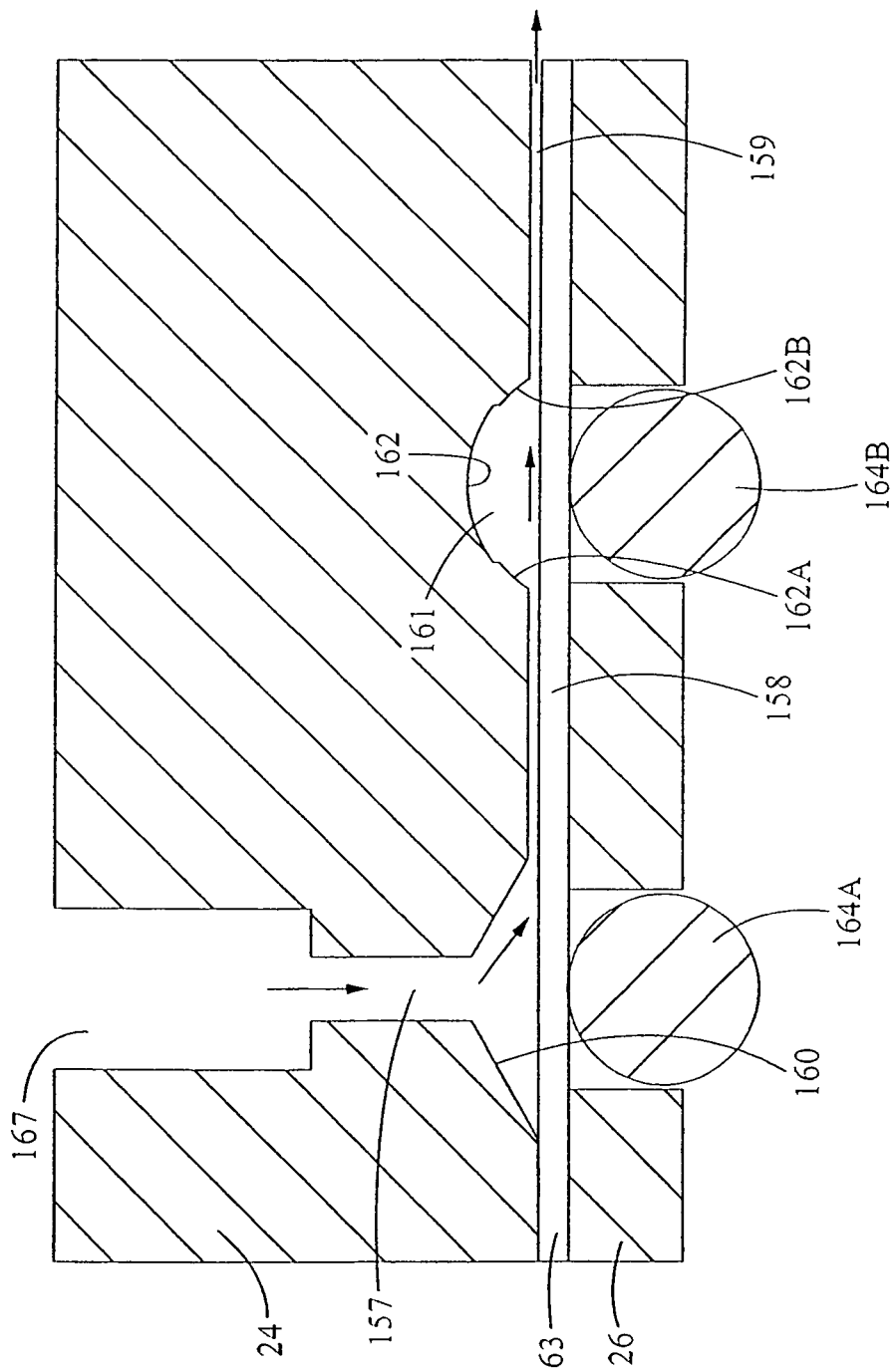
FIG. 15A is a cross-sectional view of a portion of the body of the cartridge of FIG. 1 illustrating two different types of valves in the cartridge.
Figure 15B:
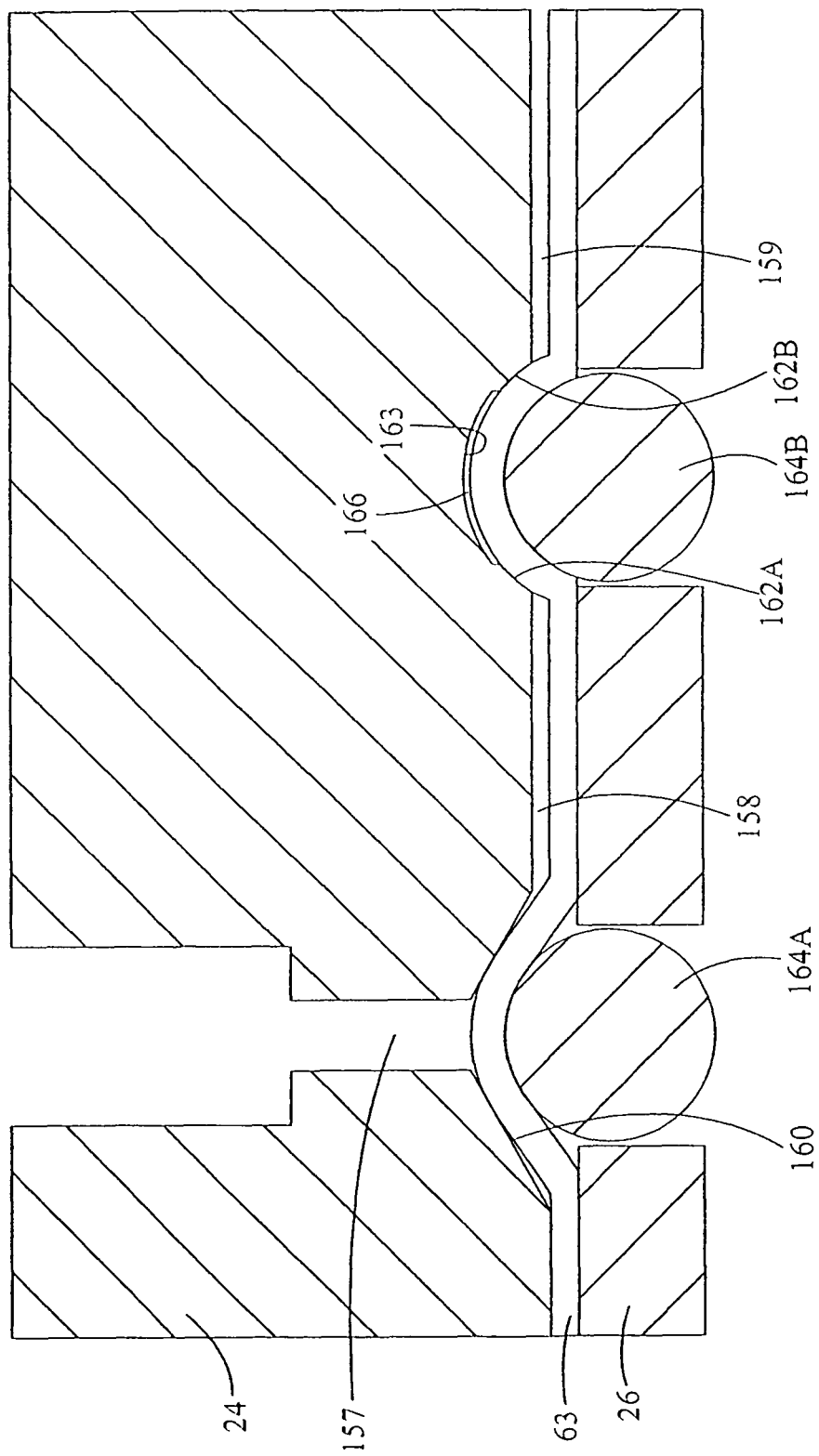
FIG. 15B is a cross-sectional view of the valves of FIG. 15A in a closed position.

FIGS. 15A-15B illustrate two types of valves used in the cartridge. As shown in FIG. 15A, there are two types of fundamental concepts to the valve action, and hence two types of valves. The first valve uses a cone-shaped or conical valve seat 160 formed in the middle cartridge piece 24. The valve seat 160 is a depression, recess, or cavity molded or machined in the middle piece 24. The valve seat 160 is in fluid communication with a chamber 167 through a port or channel 157 that intersects the center of the conical valve seat 160. As shown in FIG. 15B, a valve actuator 164 having a spherical surface is forced against the elastic membrane 63 and into the valve seat 160, establishing a circular ring of contact between the membrane 63 and the valve seat 160. The kinematic principle is that of a ball seated into a cone. The circular seal formed by the membrane 63 and valve seat 160 prevents flow between the channel 157 (and hence the chamber 167) and a side channel 158 extending from a side of the valve seat 160. The side channel 158 is defined by the membrane 63 and the middle cartridge piece 24.

As shown in FIG. 15A, the other type of valve controls the cross flow between the channel 158 and another side channel 159 formed between the membrane 63 and the middle cartridge piece 24. In this case, a circular ring of contact would be ineffective. Instead, the second valve comprises a recess depression or cavity 161 formed in the middle cartridge piece 24. The cavity 161 separates the channels 158, 159 from each other. An end of the channel 158 is positioned on one side of the cavity 161, and an end of the channel 159 is positioned on the opposite side of the cavity 161. The cavity 161 is defined by a first curved surface 162A positioned adjacent the end of the channel 158, a second curved surface 162B positioned adjacent the end of the channel 159, and a third surface 163 between the first and second curved surfaces 162A, 162B. As shown in FIG. 15B, the curved surfaces provide two valve seats that are the primary contact area for the membrane 63 to seal off the flow between the channels 158 and 159. The kinematic principle is that of a ball (or spherical end on a valve actuator) held by three contact points, the upward force on the actuator and the two valve seats 162A, 162B.

Figure 16A:
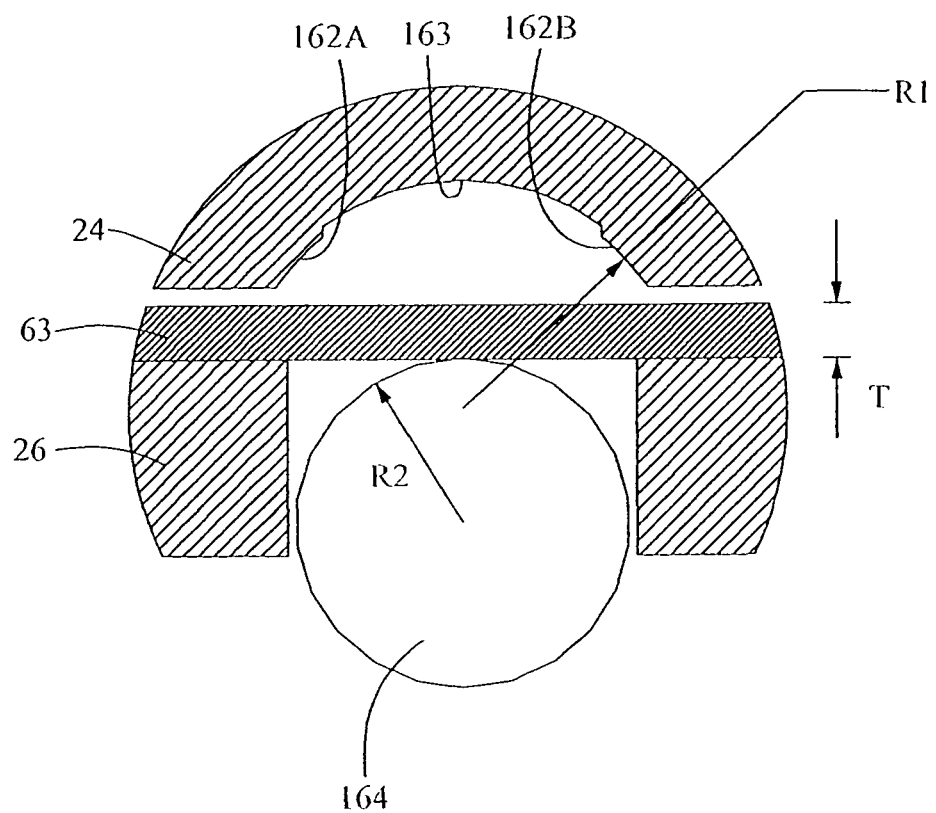
FIG. 16A is another cross-sectional view of one of the valves of FIG. 15A in an open position.

As shown in FIG. 16A, the first and second curved surfaces 162A, 162B are preferably concentric spherical surfaces. The valve actuator 164 has also has a spherical surface for pressing the membrane 63 tightly against the surfaces 162A, 162B. In addition, each of the surfaces 162A, 162B preferably has a spherical radius of curvature R1 equal to the combined radius of curvature R2 of the valve actuator 164 plus the thickness T of the membrane 63. For example, if the radius of curvature R2 of the surface of the valve actuator 164 is 0.094 inches and the membrane 63 has a thickness T of 0.031 inches, then the radius of curvature RI of each of the surfaces 162A, 162B is 0.125 inches. In general, the size and radius of curvature of the valve seats is dependent upon the size of the channels in the cartridge. The valves are preferably made just large enough to effectively seal the channels but no larger so that dead volume in the cartridge is minimized.

Figure 16B:
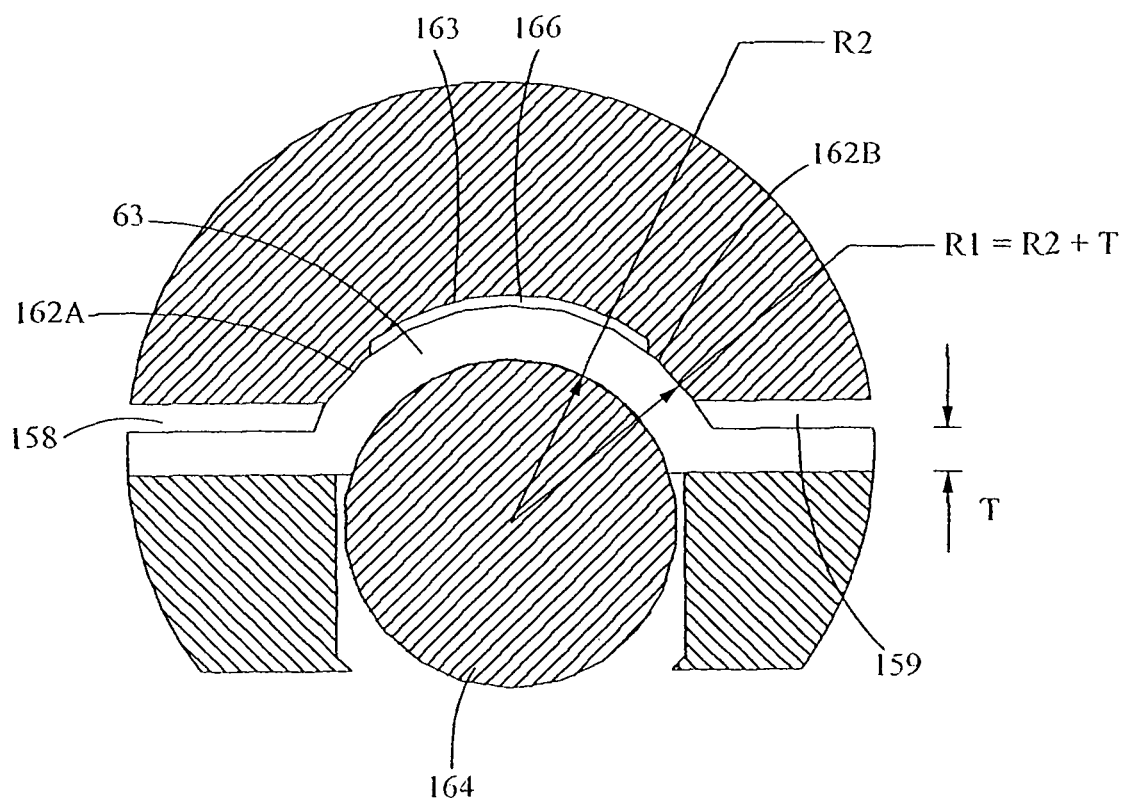
FIG. 16B is a cross-sectional view of the valve of FIG. 16A in a closed position.

As shown in FIG. 16B, the third surface 163 is recessed from the first and second surfaces 162A, 162B to provide a gap 166 between the membrane 63 and the third surface 163 when the membrane 63 is pressed against the first and second surfaces 162A, 162B. Stated another way, the surfaces 162A, 162B are raised or elevated from the surface 163. The gap 166 ensures that the membrane 63 contacts primarily the valve seats 162A, 162B rather than the entire surface of the cavity 161 so that maximum pressure is applied to the valve seats 162A and 162B by the membrane 63. This provides a very strong seal with minimal actuator force required.

Referring again to FIG. 15B, in both types of valves the respective kinematic principle defines the location of the mating parts. In both the ball-in-cone concept and the ball-against-two-spherical-surfaces concept, the ball or spherical shaped valve actuator is permitted to seek its own location as it is forced against the valve seat(s). There is a deliberate clearance (e.g., 0.01 to 0.03 inches) between the valve actuator and the hole in the bottom cartridge piece 26 in which the actuator 164 travels so that only the valve seat action defines the location of the mating pieces.

Figure 17:
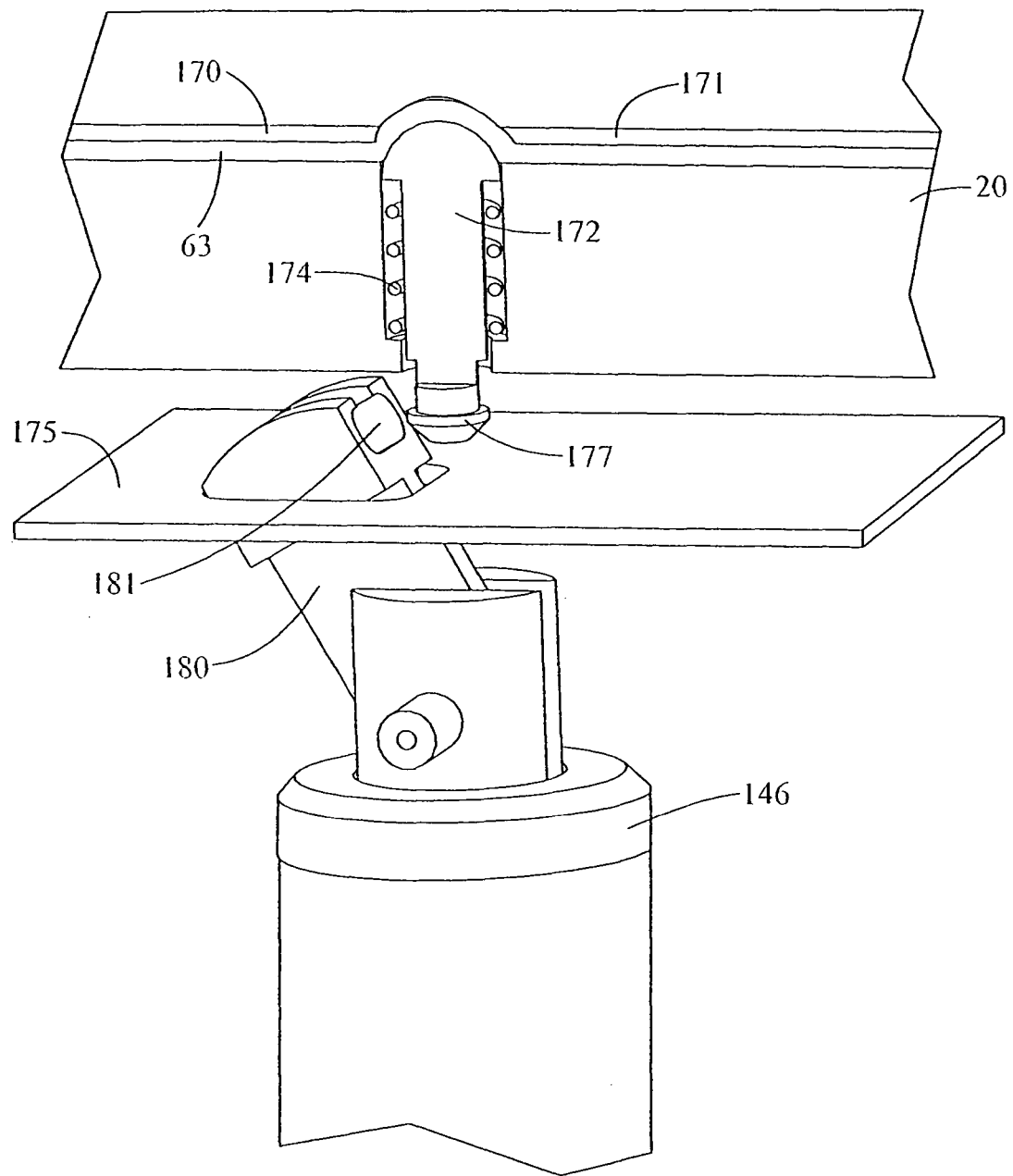
FIGS. 17-19 illustrate a valve actuation system for opening and closing the valves of FIG. 15A.
Figure 18:
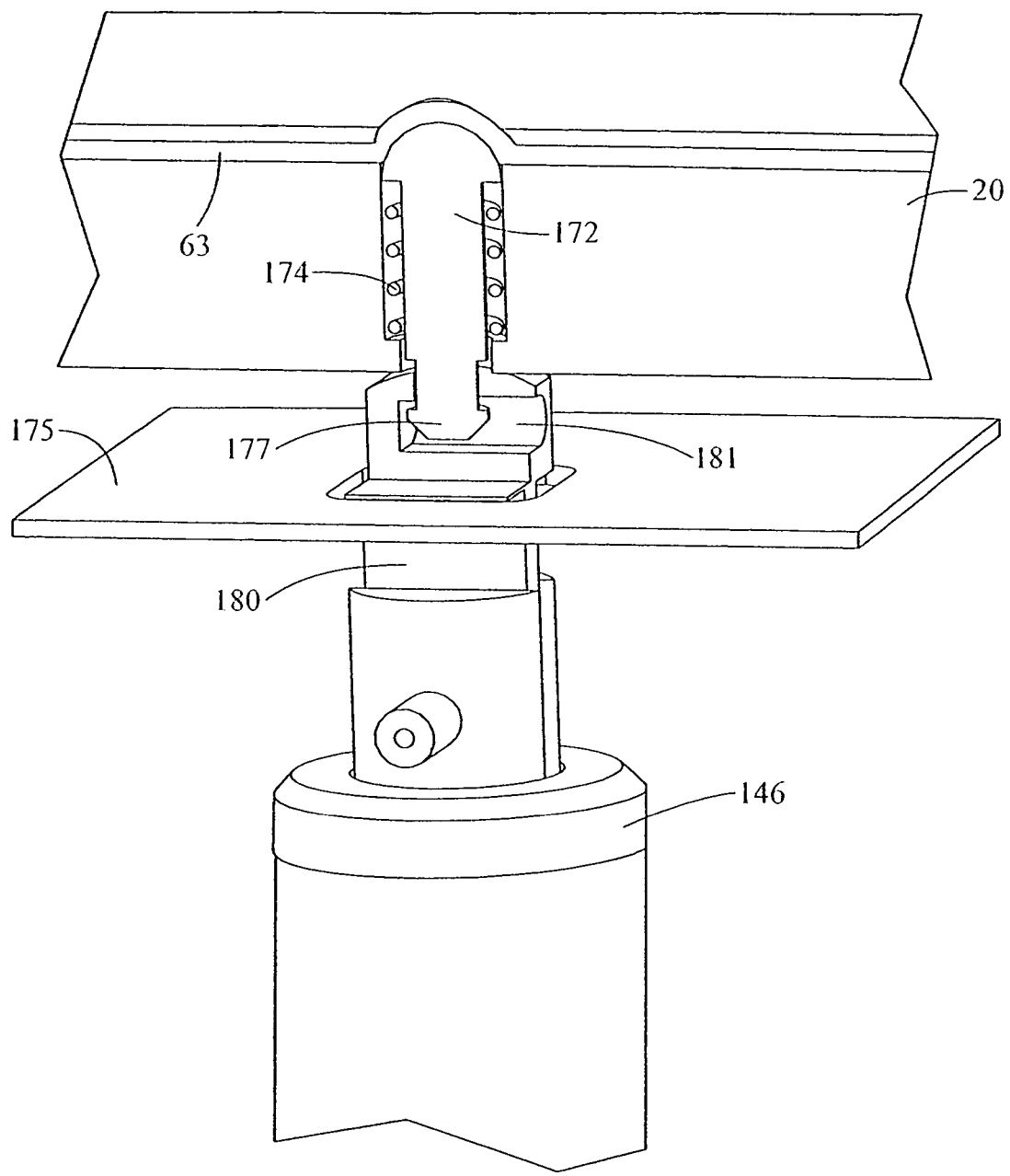
Figure 19:
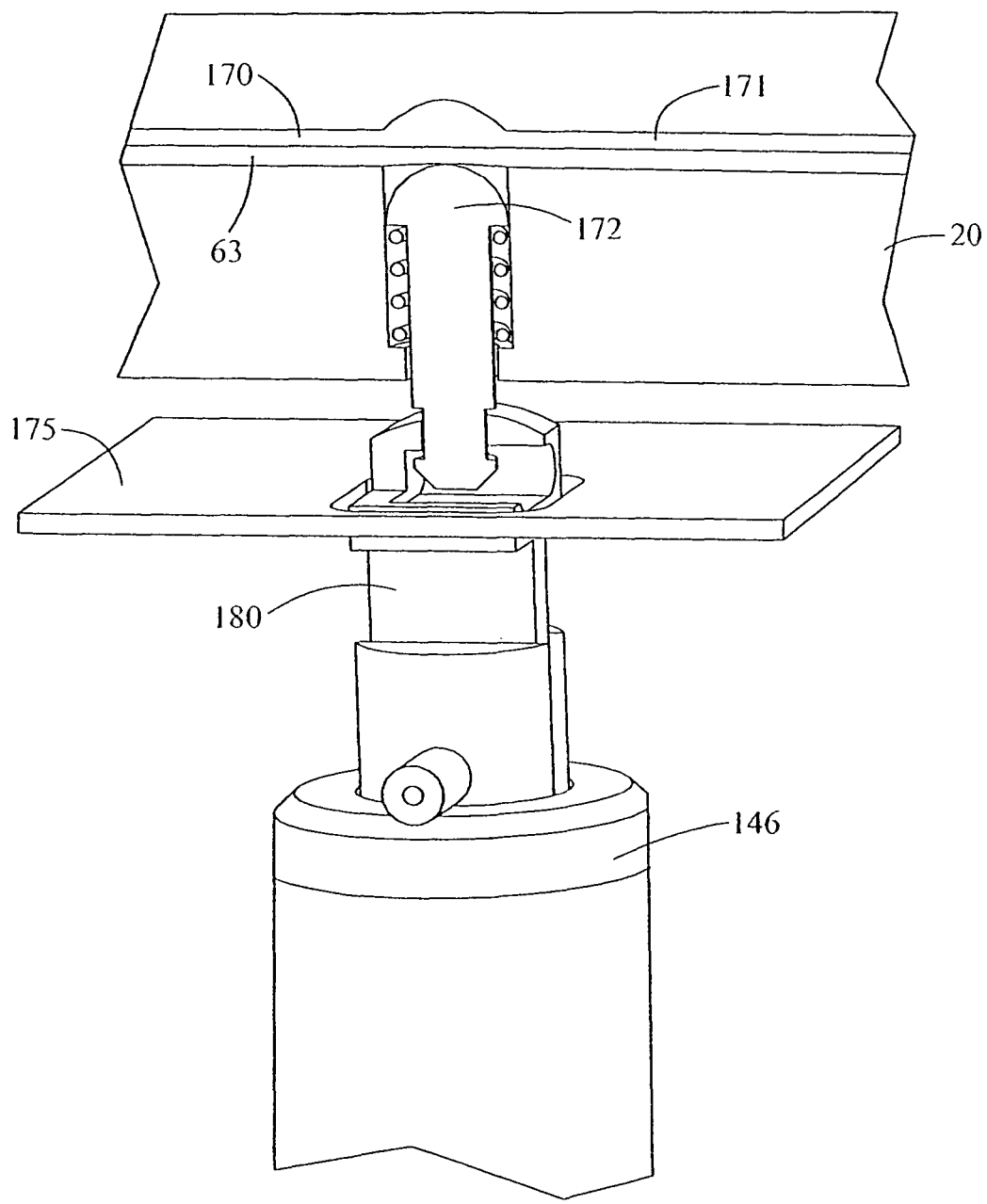

The valve actuators can be controlled by a variety of mechanisms. FIGS. 17-19 illustrate one such mechanism. As shown in FIG. 17, a valve actuator 172 has a spherical surface for pressing the gasket 63 into a valve seat. The actuator 172 also has a flange 177 on its bottom portion. The cartridge includes an elastic body, such as a spring 174, that pushes against a ledge in the lower cartridge piece 26 to bias the valve actuator against the gasket 63. The spring 174 is sufficiently strong to close the valve unless a deliberate force is applied to pull down the actuator 172. The valves in the cartridge may be kept closed in this manner for shipping and storage before the cartridge is used. Thus, the cartridge may be preloaded during manufacture with the necessary reagents and wash solutions to analyze a fluid sample without the fluids leaking out of the cartridge during shipping and storage.

The actuator pull-down mechanism is usually located in an instrument into which the cartridge is placed for sample analysis (one such instrument is described in detail below with reference to FIG. 10). The mechanism comprises a sliding guide 175 that rotates a hinged pull-down member 180 having a jaw 181 for receiving the flange 177 of the actuator 172. As shown in FIG. 18, the sliding guide 175 rotates the hinged pull-down member 180 until the flange 177 is positioned within the jaw 181. As shown in FIG. 19, a solenoid 146 pulls down the member 180 and thus the valve actuator 172 so that the gasket 63 is released from the valve seat, thus opening the valve and permitting fluid flow between the channels 170 and 171.

Figure 20:
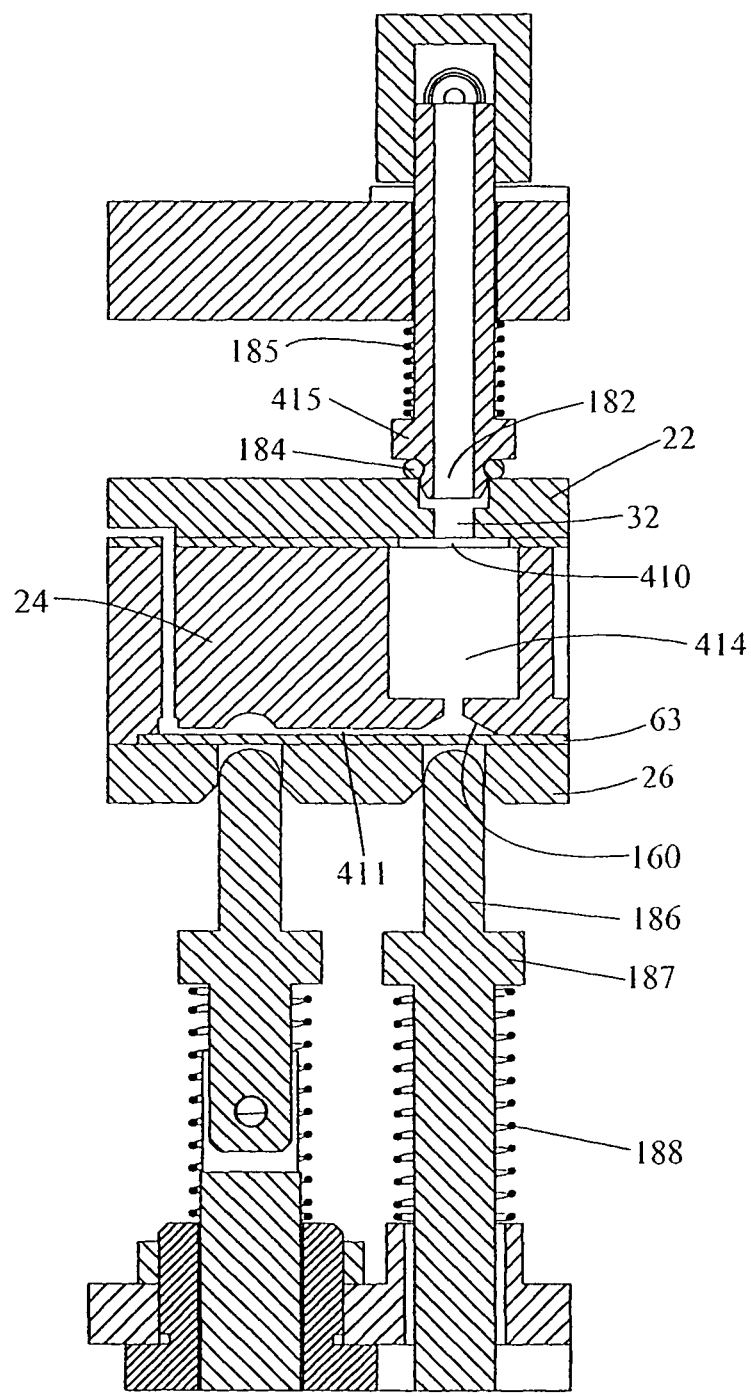
FIG. 20 is a cross sectional view of alternative valve actuators for opening and closing the valves in the cartridge of FIG. 1.

FIG. 20 illustrates the manner in which fluid flow into and out of the sample chamber, wash chamber, neutralizer chamber, and reagent chambers is controlled in the cartridge. Each of these chambers, as illustrated by a chamber 414 in FIG. 20, is covered by a hydrophobic membrane 410 that allows the passage of gas but not liquid therethrough. The hydrophobic membrane 410 is positioned between the chamber 414 and a pressure port 32. The pressure port 32 is formed in the upper cartridge piece 22 and positioned over the chamber 414. The membrane 410 holds liquids in the chamber 414 during shipping and storage of the cartridge, even if the cartridge is turned upside down. The pressure port 32 is sized to receive a pressure nozzle 182 that is connected to a pressure source (e.g., a vacuum or pneumatic pump) usually located in the external instrument. The nozzle 182 includes an o-ring 184 and a flange 415. A spring 185 pushes against the flange 415 to force the nozzle 182 into the pressure port 32 so that the o-ring 184 establishes a seal around the port 32. In operation, positive air pressure or a vacuum is applied to the chamber 414 through the pressure port 32 to force liquids out of or into, respectively, the chamber 414.

A conical valve seat 160 (previously described with reference to FIGS. 15A-15B) is formed in the middle cartridge piece 24 below the chamber 414 to control the flow of liquid between the chamber 414 and a connecting channel 411. The valve is opened and closed by a valve actuator 188 having a flange 187 and a spring 188 pressing against the flange to hold the valve closed until a downward force is applied to the actuator 186. The downward force is preferably supplied by a solenoid that pulls down the actuator 186 to open the valve. The valve actuator 186 and solenoid are preferably located in the instrument.

Figure 7:
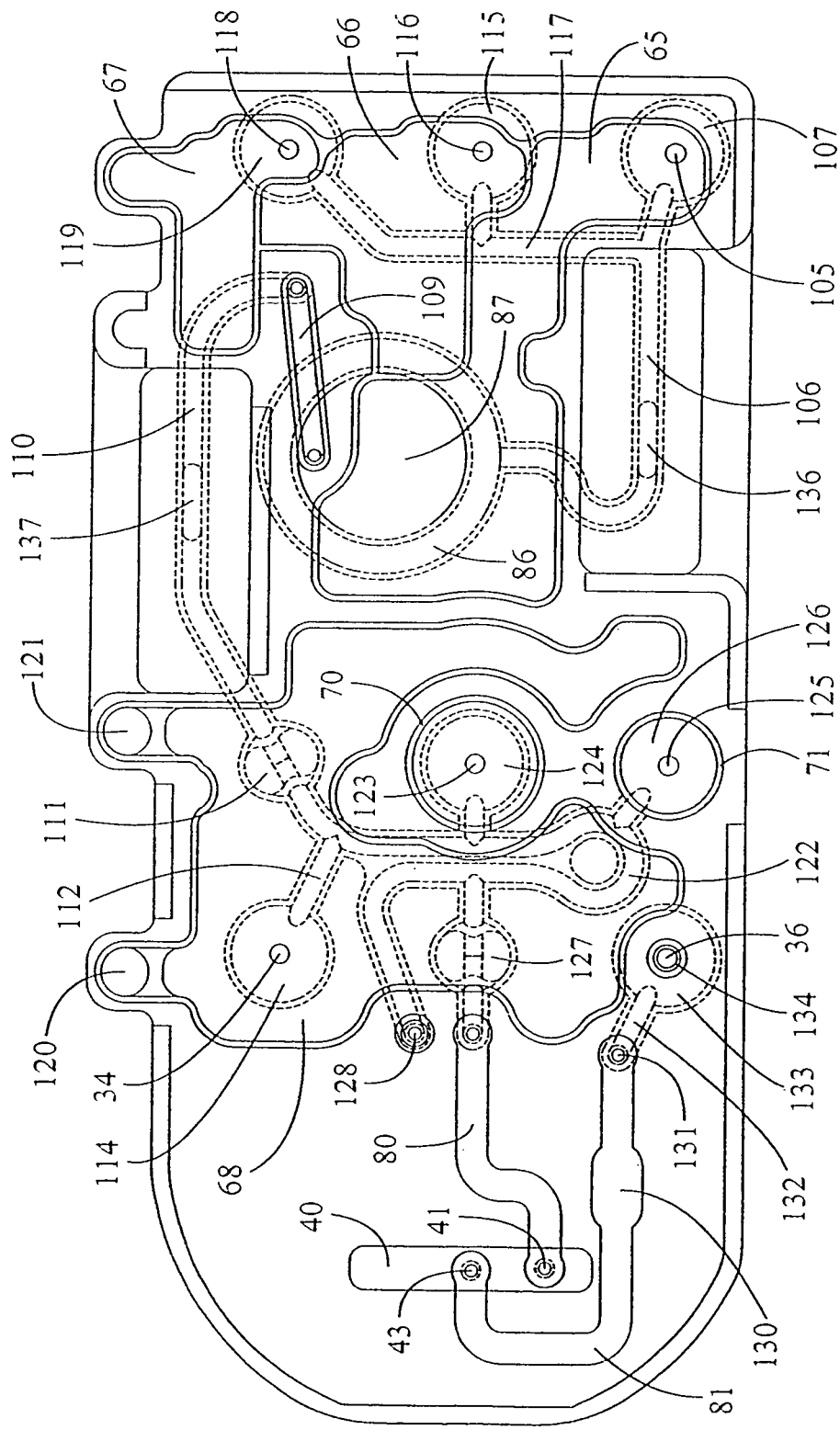
FIG. 7 is a top plan view of the cartridge of FIG. 1.
Figure 8:
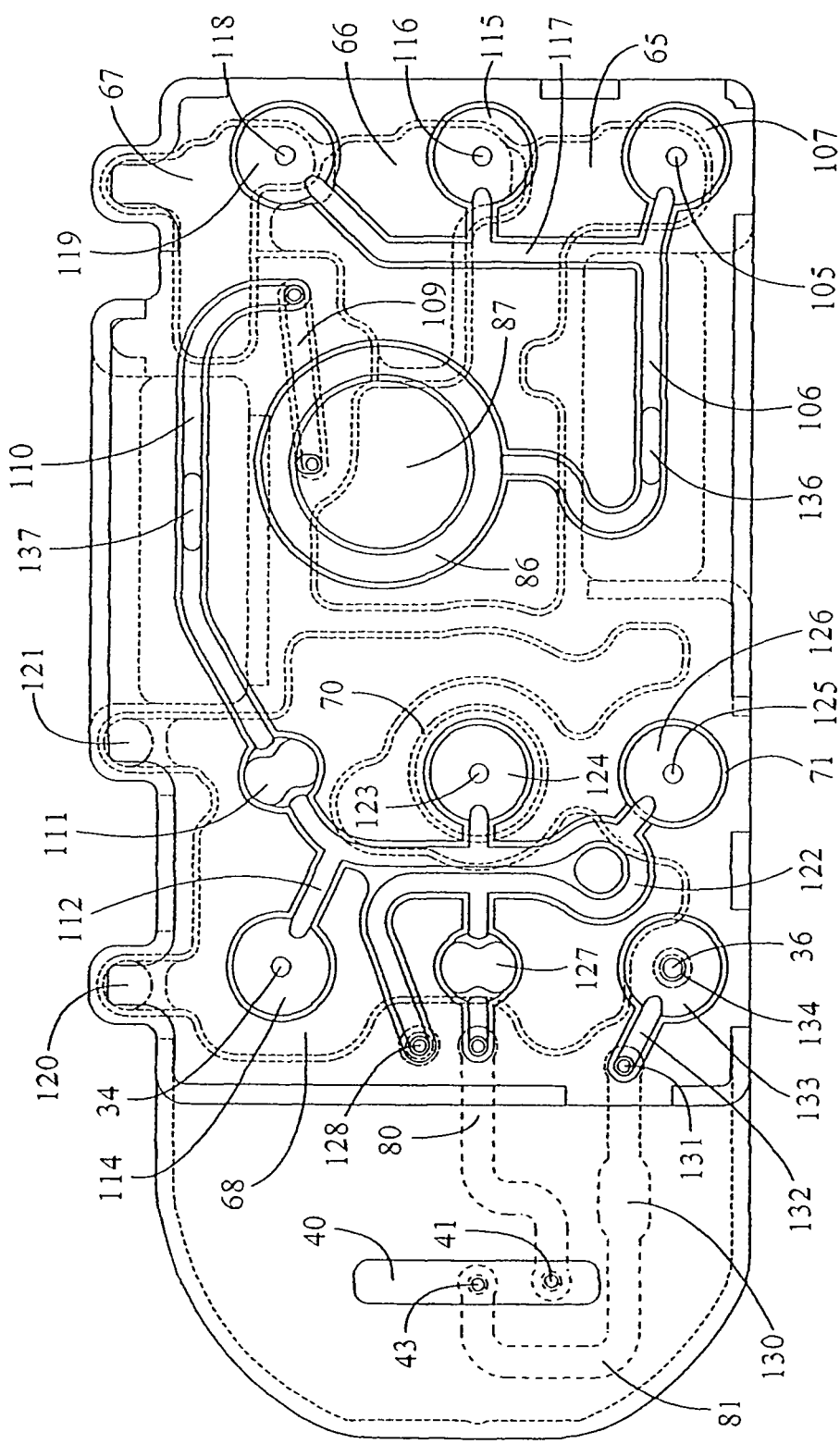
FIG. 8 is a bottom plan view of the cartridge of FIG. 1.
Figure 9:
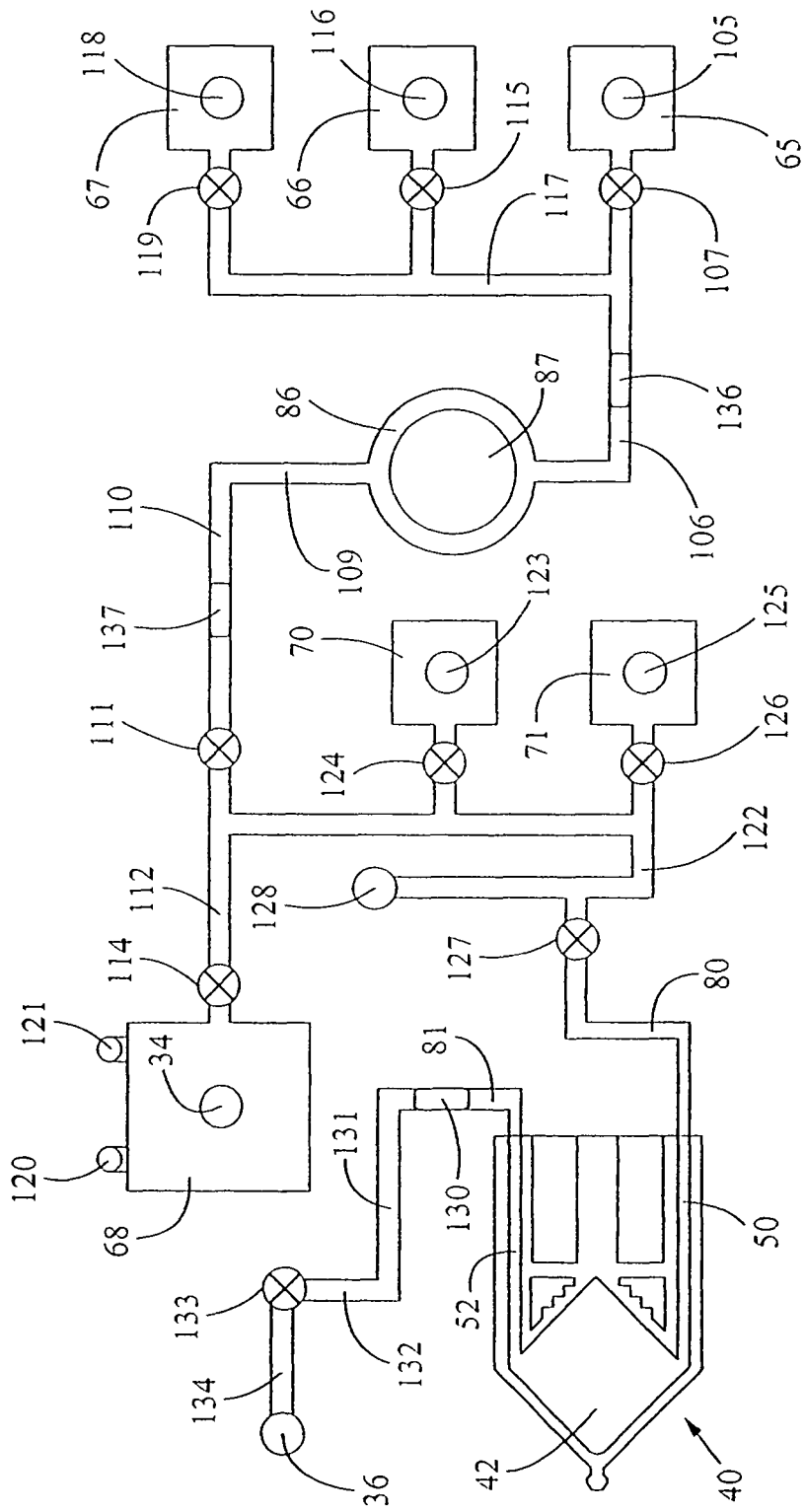
FIG. 9 is a schematic block diagram of the cartridge of FIG. 1.

FIGS. 7-8 show top and bottom plan views, respectively, of the cartridge. FIG. 9 is a schematic block diagram of the cartridge. As shown in any of FIGS. 7-9, the cartridge includes a sample chamber 65 having a port for adding a fluid sample to the cartridge and a sample flow path extending from the sample chamber 65. The sample flow path extends from the sample chamber 65 through a valve 107 and into a channel 106. The channel 106 includes a sensor region 136 in which the channel 106 has a flat bottom enabling easy optical detection of the presence of liquid in the channel. The sample flow path continues from the channel 106 into the lysing chamber 86 and through the filter stack 87. The sample flow path also includes a channel 109 for exit of fluid from the lysing chamber 86, a channel 110 having a flat-bottomed detection region 137, a valve 111, and a channel 112 leading to the vented waste chamber 68 through a valve 114.

The cartridge also includes the wash chamber 66 for holding wash solution and the reagent chamber 67 for holding lysing reagent. The wash chamber 66 is connected to the lysing chamber 86 through a valve 115, channel 117, and channel 106. The reagent chamber 67 is connected to the lysing chamber 86 through a valve 119, channel 117, and channel 106. Sample components (e.g., cells or viruses in the sample) are captured in the filter stack 87 and lysed in the chamber 86 to release target analyte (e.g., nucleic acid) from the sample components. The cartridge also includes an analyte flow path extending from the lysing chamber 86 for carrying the analyte separated from the fluid sample to the reaction vessel 40 for chemical reaction and optical detection. The analyte flow path extends from the chamber 86 through the channel 109, channel 110, and valve 111. After passing through the valve 111, the analyte flow path diverges from the sample flow path. While the sample flow path extends though channel 112 into the waste chamber 68, the analyte flow path diverges into the U-shaped channel 122. The analyte flow path then extends into and out of the neutralizer chamber 70 through a valve 124. The analyte flow path also passes into and out of the master mix chamber 71 through a valve 126. From the master mix chamber 71, the analyte flow path extends along the channel 122, through a valve 127, through channel 80, and into the reaction vessel 40 through the port 41.

The reaction vessel 40 includes the port 41 for adding a reaction mixture to the vessel, and the port 43 for exit of fluids (e.g., air or excess reaction mixture) from the vessel. The cartridge also includes channel 81 in fluid communication with the port 43. The channel 81 includes a flat-bottomed detection region 130 for detecting the presence of liquid in the channel. The channel 81 connects to a channel 131 (channel 131 extends straight down perpendicular to the page in the top plan view of FIG. 7). Channel 131 connects to a channel 132 which in turn connects to a channel 134 through a valve 133 (channel 134 extends straight up perpendicular to the page in the top plan view of FIG. 7). The channel 134 leads to the vent 36 which has a hydrophobic membrane to permit the escape of gas but not liquid from the cartridge. The channels, vent and valve positioned downstream from the reaction vessel 40 are used to pressurize the chamber 42 of the vessel, as is described in the operation section below.

The cartridge also includes a first pressure port 105 positioned above the sample chamber 65, a second pressure port 116 positioned above the wash chamber 66, a third pressure port 118 positioned above the reagent chamber 67, a fourth pressure port 123 positioned above the neutralizer chamber 70, a fifth pressure port 125 positioned above the master mix chamber 71, and a sixth pressure port 128 positioned at the end of the U-shaped channel 122. The cartridge further includes sensor chambers 120 and 121 in fluid communication with the waste chamber 68. The sensor chambers 120 and 121 indicate when predetermined volumes of liquid have been received in the waste chamber 68, as is described in detail below.

Figure 10:
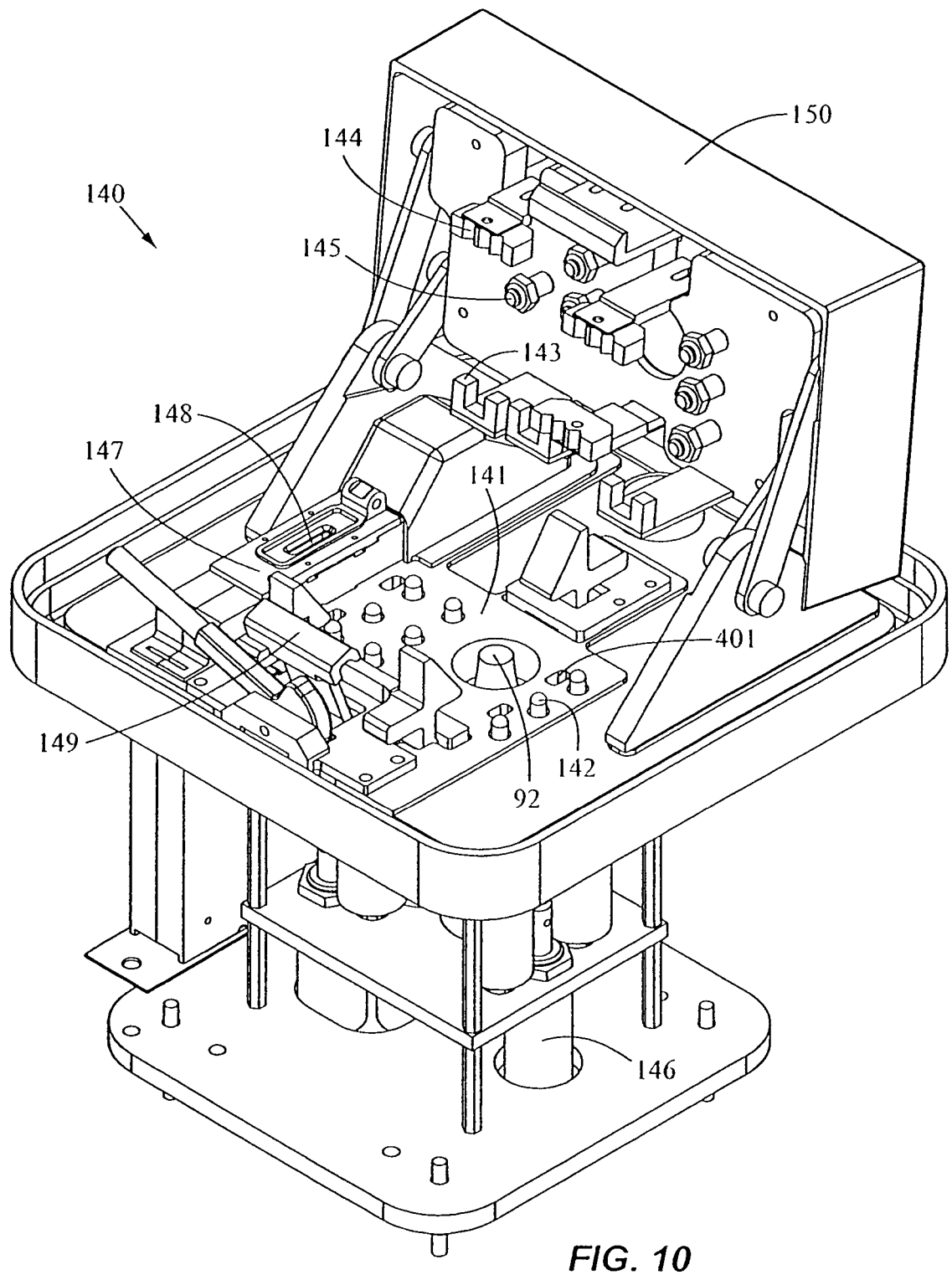
FIG. 10 is an isometric view of an instrument into which the cartridge of FIG. 1 is placed for processing.

Referring to FIG. 10, the cartridge is preferably used in combination with an instrument 140 designed to accept one or more of the cartridges. For clarity of illustration, the instrument 140 shown in FIG. 10 accepts just one cartridge. It is to be understood, however, that the instrument may be designed to process multiple cartridges simultaneously. The instrument 140 includes a cartridge nest 141 into which the cartridge is placed for processing. The instrument 140 also includes the transducer 92 (e.g., an ultrasonic horn) for generating dynamic pressure pulses or pressure waves in the lysing chamber of the cartridge, nine valve actuators 142 for actuating the nine valves in the cartridge, nine corresponding solenoids 146 for pulling down the valve actuators, and six pressure nozzles 145 for interfacing with six corresponding pressure ports formed in the cartridge. In addition, the instrument includes or is connected to one or more regulated pressure sources for supplying pressure to the cartridge through the pressure nozzles 145. Suitable pressure sources include syringe pumps, compressed air sources, pneumatic pumps, or connections to external sources of pressure. The instrument further includes three slotted optical sensors 143 and three reflective optical sensors 144.

Figure 13:
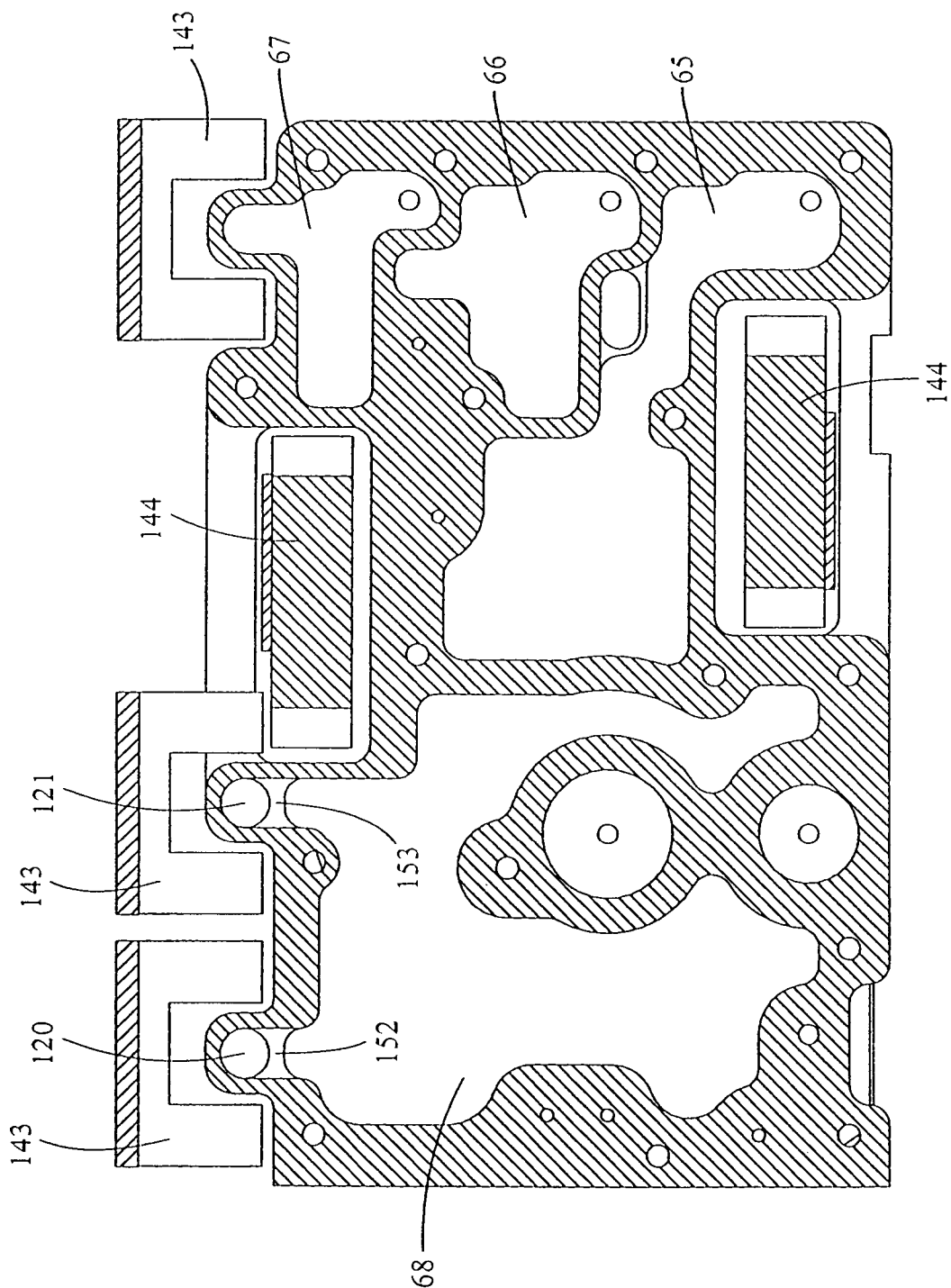
FIG. 13 is a schematic, plan view of optical sensors positioned to detect liquid levels in the cartridge of FIG. 1.

FIG. 13 illustrates the slotted optical sensors 143 positioned to detect liquid in the sensor chambers 120, 121 and in the reagent chamber 67. Each sensor 143 includes a built in LED and photodiode positioned on opposite sides of the sensor. The LED emits a beam that is detected by the photodiode if the beam is not substantially refracted. Such slotted optical sensors are commercially available from a number of suppliers. The cartridge is shaped so that the slotted optical sensors fit around the chambers 67, 120, and 121. The operation of each sensor is as follows. If liquid is not present in the chamber the sensor surrounds, the beam from the LED is substantially refracted by air in the chamber and the curved inner walls of the chamber and only a weak signal, if any, is detected by the photodiode since air has an index of refraction that does not closely match that of the plastic cartridge. If there is liquid present in the chamber, however, the beam from the LED does not refract or is only slightly refracted and produces a much stronger signal detected by the photodiode since the liquid has an index of refraction closely matching that of the plastic cartridge. The optical sensors 143 are therefore useful for determining the presence or absence of liquid in the chambers 67, 120, and 121.

Figure 14:
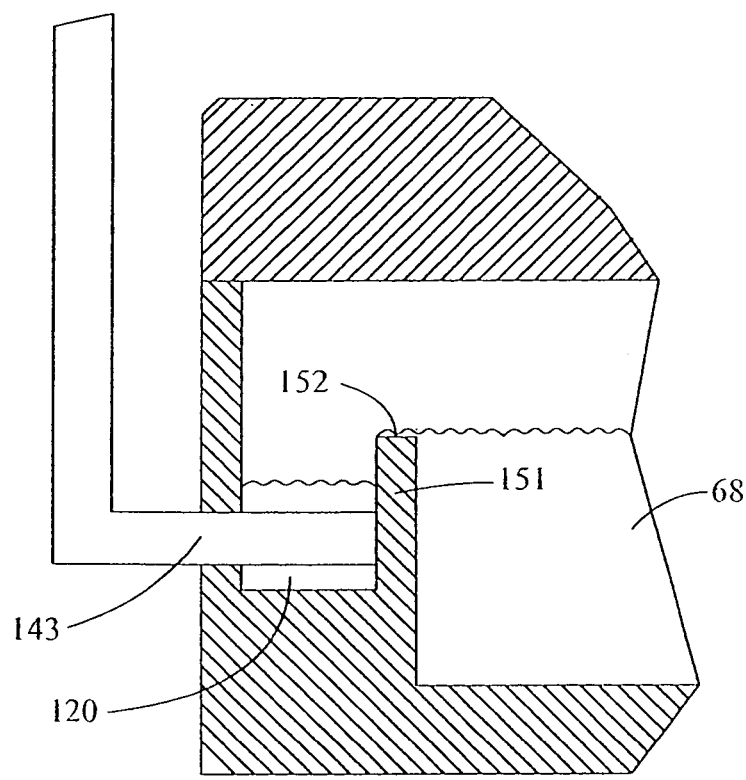
FIG. 14 is a partially cut away, schematic, side view of a slotted optical sensor positioned to detect the liquid level in a sensor chamber of the cartridge of FIG. 1.

FIG. 14 shows a cut-away, schematic side view of the sensor chamber 120 in fluid communication with the waste chamber 68 and surrounded by the slotted optical sensor 143. The sensor chamber 120 and sensor 143 are used to indicate when a predetermined volume of liquid is present in the waste chamber 68. The sensor chamber 120 is partially separated from the waste chamber 68 by a wall 151 having a spillover rim 152. The height of the wall is selected so that when the predetermined volume of liquid is received in the waste chamber 68, the liquid spills over the spillover rim 152 and into the sensor chamber 120. The liquid in the sensor chamber 120 is then detected by the sensor 143.

Referring again to FIG. 13, the cartridge may also include a second sensor chamber 121 in fluid communication with the waste chamber 68. The second sensor chamber 121 is also separated from the waste chamber 68 by a wall 153 having a spillover rim. The wall 153 is taller than the wall 152 so that liquid does not spill over the wall 153 until a second predetermined volume of fluid in addition to the first predetermined volume of fluid has been received in the waste chamber 68. The sensor chambers 120, 121 and the optical sensors 143 are useful for controlling the operation of the cartridge. The height of the wall 152 is preferably selected such that when a fixed volume of fluid sample from the sample chamber 65 has flowed through the sample flow path to the waste chamber 68, the sample liquid spills over into the sensor chamber 120 and is detected. The detection in chamber 120 triggers the release of wash solution from the wash chamber 66 which flows through the sample flow path to the waste chamber 68. When an incremental volume of the wash solution is received in the chamber 68, liquid spills over the wall 153 into the sensor chamber 121 and is detected. The detection of liquid in the chamber 121 then triggers the release of lysing reagent from the chamber 67. The sensor 143 surrounding the chamber 67 may then be used to indicate when the chamber 67 is empty, triggering the start of ultrasonic lysis. In an alternative embodiment, the cartridge may have two waste chambers, one for sample and one for wash, with each waste chamber having a respective sensor chamber connected thereto.

In-line reflective optical sensors 144 are used to determine the presence or absence of liquid in the flat-bottomed detection regions 130, 136, 137, of channels 81, 106, and 110, respectively (FIG. 7). Each sensor 144 has a built in emitter and detector that is positioned over a flat-bottomed detection region. The emitter emits a beam that is reflected from the cartridge and detected by the detector. The sensor detects a change in signal when as an air/liquid interface passes through the detection region. Optionally, dual emitter reflective optical sensors may be used for a more reliable detection operation. Both types of reflective optical sensors are well known in the art and commercially available.

Referring again to FIG. 10, the instrument 140 also includes a heat-exchanging module 147 having a slot 148 for receiving the reaction vessel of the cartridge. The module 147 is described in detail below with reference to FIG. 28. The instrument 140 further includes a latch mechanism 149 for latching a lid 150 over a cartridge. The cartridge nest 141 includes alignment holes 401 for receiving the legs of the cartridge. The alignment holes 401 ensure proper positioning of the cartridge in the nest 141 so that the pressure nozzles 145, transducer 92, and valve actuators 142 fit into the corresponding ports in the cartridge and so that the reaction vessel fits into the slot 148. The transducer 92 should be positioned in the instrument 140 such that when the cartridge is placed in the nest 141, the transducer contacts the bottom wall of the lysing chamber 86, as shown in the cut-away view of FIG. 5. In addition, the instrument may include a spring or similar mechanism to bias the transducer 92 against the wall of the lysing chamber 86.

The instrument 140 also includes various conventional equipment not shown in FIG. 10 including a main logic board having a microcontroller for controlling the operation of the solenoids 146, transducer 92, heat-exchanging module 147, and optical sensors 143, 144. The instrument also includes or is connected to a power supply for powering the instrument and a pneumatic pump for supplying air pressure through the nozzles 145. The instrument 140 is preferably computer-controlled using, e.g., the microcontroller which is programmed to perform the functions described in the operation section below. Alternatively, the instrument may controlled by a separate computer, or controlled by a combination of a separate computer and an on-board microcontroller.

Figure 11:
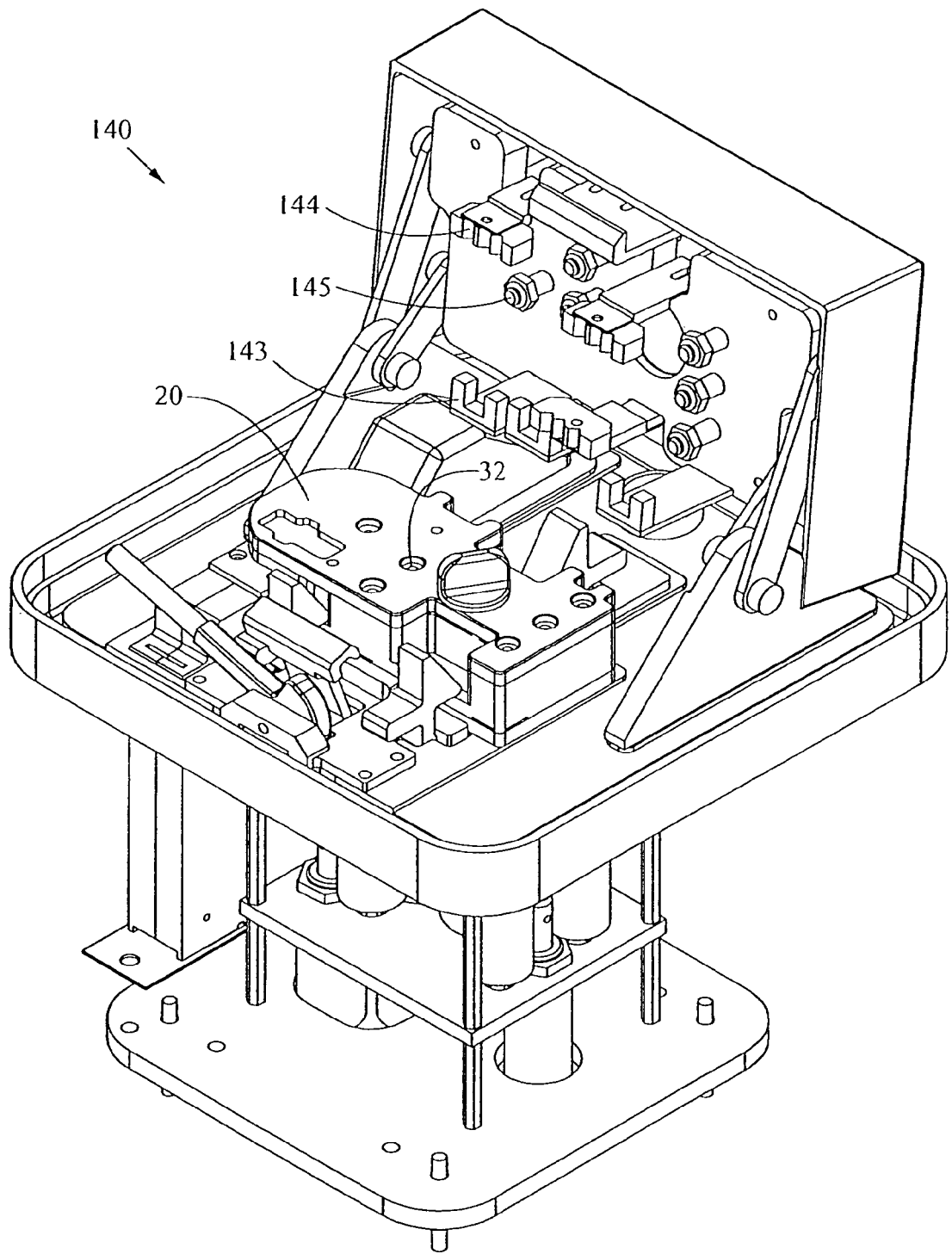
FIG. 11 is an isometric view of the cartridge of FIG. 1 in the instrument of FIG. 10.
Figure 12:
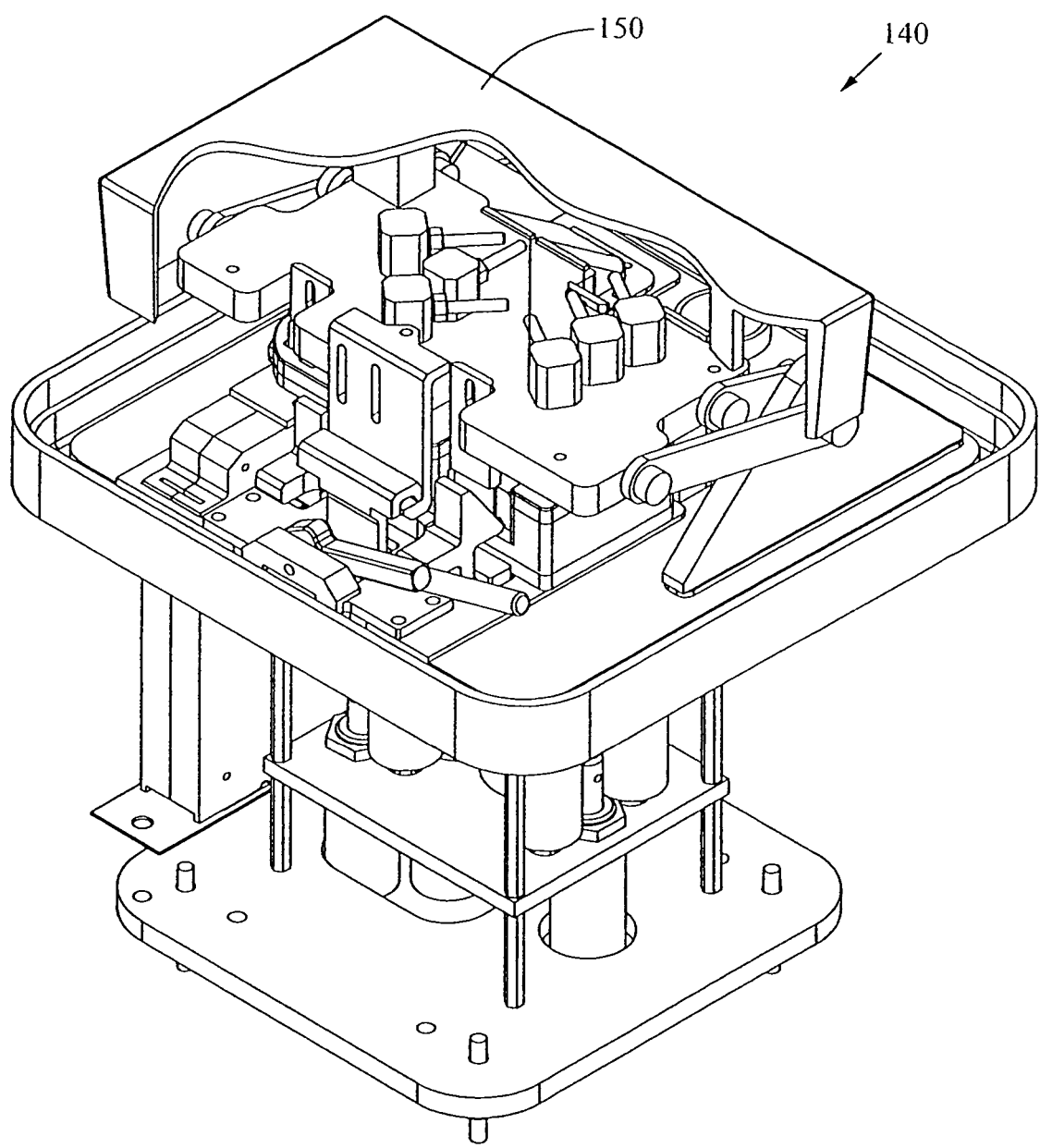
FIG. 12 is a partially cut-away view of the cartridge of FIG. 1 in the instrument of FIG. 10.

FIG. 11 shows an isometric view of the cartridge 20 placed in the instrument 140 for processing. FIG. 11 shows a partial cut-away view of the instrument 140 with the lid 150 closed. Referring again to FIG. 11, a memory or microprocessor chip may optionally be incorporated as part of the cartridge 20. This chip preferably contains information such as the type of cartridge, program information such as specific protocols for the processing of the cartridge, tolerances for accept and reject, serial numbers and lot codes for quality tracking, and provision for storing the results of the processing. Integrated electronic memory on the cartridge 20 allows for rapid, easy, and error-free set-up of the instrument 140 for different fluidic processing protocols. When the cartridge 20 is inserted into the instrument 140, the instrument may electronically address the memory on the cartridge, and thus automatically receive the appropriate set of instructions for controlling the time-sequence of fluidic operations to be carried out with the inserted cartridge. The instrument 140 may simply sequentially retrieve and execute each step in the cartridge's memory, or download its contents so that the user may edit the sequence using, e.g., the controller computer.

If suitable memory is included on the cartridge, such as writable memory (e.g., erasable programmable read-only memory (EPROM), electrically erasable programmable read-only memory (EEPROM), etc., intermediate and final results, based on the sample introduced into the cartridge, could be written by the instrument into the cartridge's memory for co-located storage with the physical sample after processing. This is particularly advantageous in applications where archiving of samples and results is necessary, such as forensics. In addition, other information can be stored in the memory on the cartridge, in unalterable (or alterable) forms. For example, cartridge serial number, lot manufacture information, and related information could be pre-programmed and unalterable. User data, technician identification number, date of test, location of test and instrument serial number could be unalterably written into the cartridge. This allows for easy identification of the "chain of custody" in the handling of a specimen. Engineers skilled in the art of data storage will recognize that other memory means than electronic can be used, such as optically-addressed printed regions (e.g., ink-jet or thermal), magnetic strips, etc.

Figure 28:
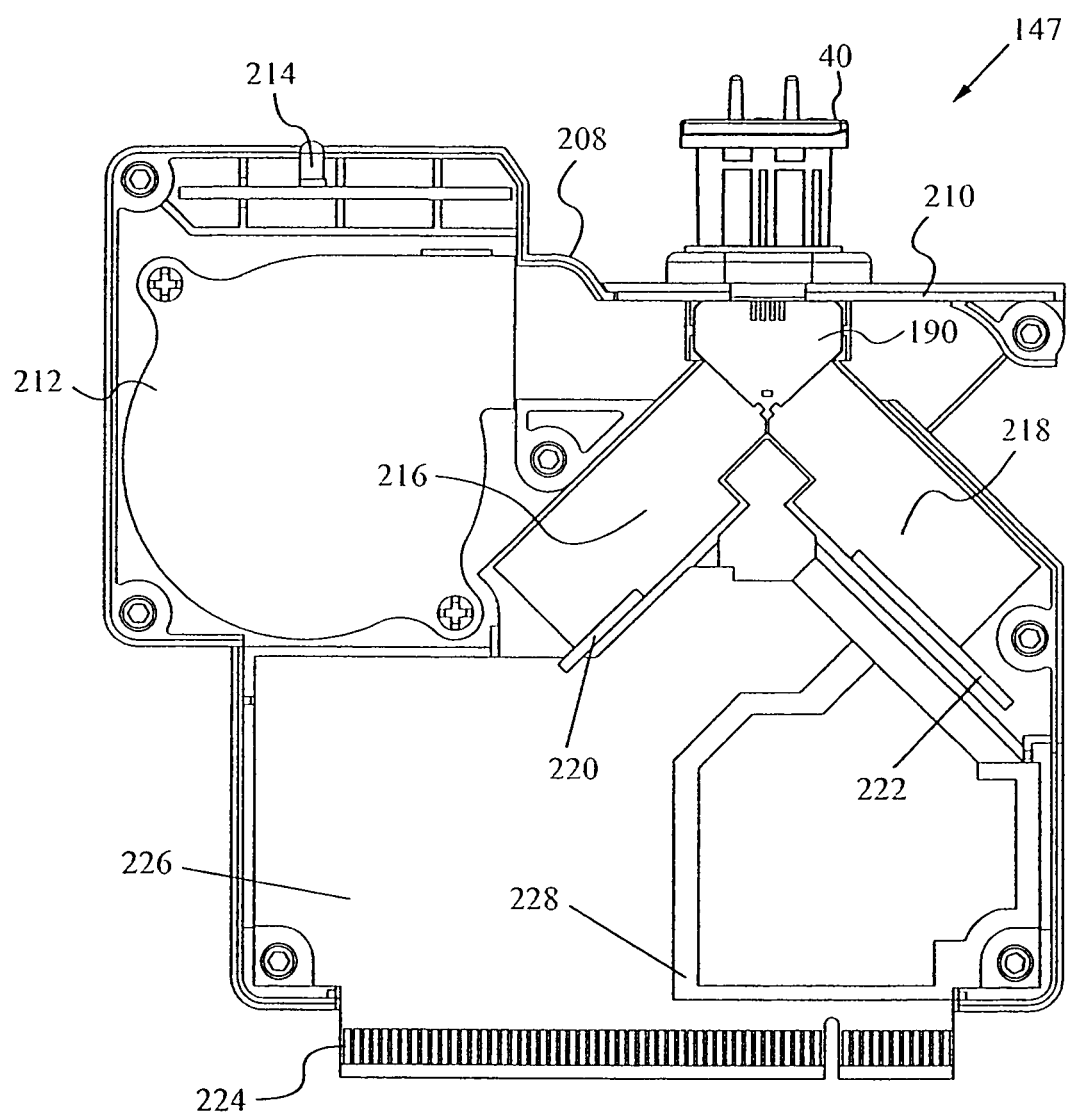
FIG. 28 is a front view of the vessel of FIG. 21 inserted into a heat-exchanging module of the instrument of FIG. 10.

FIG. 28 shows the heat-exchanging module 147 of the instrument into which the reaction vessel 40 is inserted for thermal processing and optical detection of target analyte(s) in the reaction mixture. The module 147 preferably includes a housing 208 for holding the various components of the module. The module 147 also includes the thermal plates 190 described above. The housing 208 includes a slot (not shown in FIG. 28) above the plates 190 so that the reaction chamber of the vessel 40 may be inserted through the slot and between the plates. The heat-exchanging module 147 also preferably includes a cooling system, such as a fan 212. The fan 212 is 1 positioned to blow cooling air past the surfaces of the plates 190 to cool the plates and hence cool the reaction mixture in the vessel 40. The housing 208 preferably defines channels for directing the cooling air past the plates 190 and out of the module 147.

The heat-exchanging module 147 further includes an optical excitation assembly 216 and an optical detection assembly 218 for optically interrogating the reaction mixture contained in the vessel 40. The excitation assembly 216 includes a first circuit board 220 for holding its electronic components, and the detection assembly 216 includes a second circuit board 222 for holding its electronic components. The excitation assembly 216 includes one or more light sources (e.g., an LED, laser, or light bulb) for exciting fluorescently-labeled analytes in the vessel 40. The excitation assembly 216 also includes one or more lenses for collimating the light from the light sources, as well as filters for selecting the excitation wavelength ranges of interest. The detection assembly 218 includes one or more detectors (e.g., a photodiode, photomultiplier tube, or CCD) for detecting the light emitted from the vessel 40. The detection assembly 218 also includes one or more lenses for focusing and collimating the emitted light, as well as filters for selecting the emission wavelength ranges of interest. Suitable optical excitation and detection assemblies for use in the heat-exchanging module 147 are described in International Publication Number WO 99/60380 (International Application Number PCT/US99/11182) published Nov. 25, 1999, the disclosure of which is incorporated by reference herein.

The optics assemblies 216, 218 are positioned in the housing 208 such that when the chamber of the vessel 40 is inserted between the plates 190, the excitation assembly 216 is in optical communication with the chamber 42 through the optically transmissive side wall 57A (see FIG. 22) and the detection assembly 218 is in optical communication with the chamber through the optically transmissive side wall 57B (FIG. 22). In the preferred embodiment, the optics assemblies 216, 218 are placed into optical communication with the optically transmissive side walls by simply locating the optics assemblies 216, 218 next to the bottom edges of the plates 190 so that when the chamber of the vessel is placed between the plates, the optics assemblies 216, 218 directly contact, or are in close proximity to, the side walls.

Figure 34:
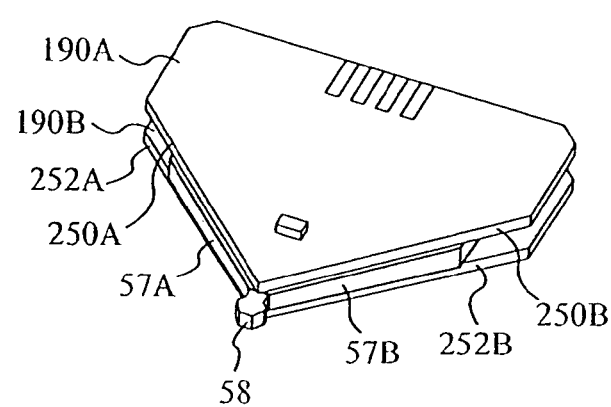
FIG. 34 is a partially cut away, isometric view of the reaction vessel of FIG. 21 inserted between the plates of FIG. 23. Only the lower portion of the vessel is included in the figure.

FIG. 34 shows a partially cut-away, isometric view of the chamber of the vessel inserted between the plates 190A, 190B (the top portion of the vessel is cut away). The vessel preferably has an angled bottom portion (e.g., triangular) formed by the optically transmissive side walls 57A, 57B. Each of the plates 190A, 190B has a correspondingly shaped bottom portion. The bottom portion of the first plate 190A has a first bottom edge 250A and a second bottom edge 2190B. Similarly, the bottom portion of the second plate 190B has a first bottom edge 252A and a second bottom edge 252B. The first and second bottom edges of each plate are preferably angularly offset from each other by the same angle that the side walls 57A, 57B are offset from each other (e.g., 90°). Additionally, the plates 190A, 190B are preferably positioned to receive the chamber of the vessel between them such that the first side wall 57A is positioned substantially adjacent and parallel to each of the first bottom edges 250A, 252A and such that the second side wall 57B is positioned substantially adjacent and parallel to each of the second bottom edges 2190B, 252B. This arrangement provides for easy optical access to the optically transmissive side walls 57A, 57B and hence to the chamber of the vessel. A gel or fluid may optionally be used to establish or improve optical communication between each optics assembly and the side walls 57A, 57B. The gel or fluid should have a refractive index close to the refractive indexes of the elements that it is coupling.

Referring again to FIG. 28, the optics assemblies 216, 218 are preferably arranged to provide a 90° angle between excitation and detection paths. The 90° angle between excitation and detection paths assures that a minimum amount of excitation radiation entering through the first side wall of the chamber exits through the second side wall. Also, the 90° angle permits a maximum amount of emitted radiation to be collected through the second side wall. In the preferred embodiment, the vessel 40 includes a locating tab 58 (see FIG. 22) that fits into a slot formed between the optics assemblies 216, 218 to ensure proper positioning of the vessel 40 for optical detection. For improved detection, the module 147 also preferably includes a light-tight lid (not shown) that is placed over the top of the vessel 40 and made light-tight to the housing 208 after the vessel is inserted between the plates 190.

Although it is presently preferred to locate the optics assemblies 216, 218 next to the bottom edges of the plates 190, many other arrangements are possible. For example, optical communication may be established between the optics assemblies 216, 218 and the walls of the vessel 40 via optical fibers, light pipes, wave guides, or similar devices. One advantage of these devices is that they eliminate the need to locate the optics assemblies 216, 218 physically adjacent to the plates 190. This leaves more room around the plates in which to circulate cooling air or refrigerant, so that cooling may be improved.

The heat-exchanging module 147 also includes a PC board 226 for holding the electronic components of the module and an edge connector 224 for connecting the module 147 to the instrument 140 (FIG. 10). The heating elements and temperature sensors on the plates 190, as well as the optical boards 220, 222, are connected to the PC board 226 by flex cables (not shown in FIG. 28 for clarity of illustration). The module 147 may also include a grounding trace 228 for shielding the optical detection circuit. The module 147 may optionally include an indicator, such as an LED 214, for indicating to a user the current status of the module such as "heating," "cooling," "finished," or "fault".

The housing 208 may be molded from a rigid, high-performance plastic, or other conventional material. The primary functions of the housing 208 are to provide a frame for holding the plates 190, optics assemblies 216, 218, fan 212, and PC board 226. The housing 208 also preferably provides flow channels and ports for directing cooling air from the fan 212 across the surfaces of the plates 190 and out of the housing. In the preferred embodiment, the housing 208 comprises complementary pieces (only one piece shown in the schematic side view of FIG. 28) that fit together to enclose the components of the module 147 between them.

Referring again to FIG. 23, the plates 190A, 190B may be made of various thermally conductive materials including ceramics or metals. Suitable ceramic materials include aluminum nitride, aluminum oxide, beryllium oxide, and silicon nitride. Other materials from which the plates may be made include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible plate materials include chrome/aluminum, superalloys, zircaloy, aluminum, steel, gold, silver, copper, tungsten, molybdenum, tantalum, brass, sapphire, or any of the other numerous ceramic, metal, or polymeric materials available in the art.

Ceramic plates are presently preferred because their inside surfaces may be conveniently machined to very high smoothness for high wear resistance, high chemical resistance, and good thermal contact to the flexible walls of the reaction vessel. Ceramic plates can also be made very thin, preferably between about 0.6 and 1.3 mm, for low thermal mass to provide for extremely rapid temperature changes. A plate made from ceramic is also both a good thermal conductor and an electrical insulator, so that the temperature of the plate may be well controlled using a resistive heating element coupled to the plate.

Various thermal elements may be employed to heat and/or cool the plates 190A, 190B and thus control the temperature of the reaction mixture in the chamber 42. In general, suitable heating elements for heating the plate include conductive heaters, convection heaters, or radiation heaters. Examples of conductive heaters include resistive or inductive heating elements coupled to the plates, e.g., resistors or thermoelectric devices. Suitable convection heaters include forced air heaters or fluid heat-exchangers for flowing fluids past the plates. Suitable radiation heaters include infrared or microwave heaters. Similarly, various cooling elements may be used to cool the plates. For example, various convection cooling elements may be employed such as a fan, peltier device, refrigeration device, or jet nozzle for flowing cooling fluids past the surfaces of the plates. Alternatively, various conductive cooling elements may be used, such as a heat sink, e.g. a cooled metal block, in direct contact with the plates.

Figure 24:
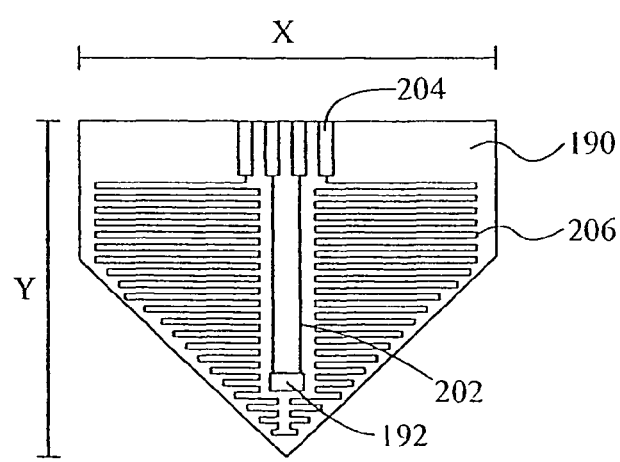
FIG. 24 is a front view of one of the heater plates of FIG. 23.

Referring to FIG. 24, each plate 190 preferably has a resistive heating element 206 disposed on its outer surface. The resistive heating element 206 is preferably a thick or thin film and may be directly screen printed onto each plate 190, particularly plates comprising a ceramic material, such as aluminum nitride or aluminum oxide. Screen-printing provides high reliability and low cross-section for efficient transfer of heat into the reaction chamber. Thick or thin film resistors of varying geometric patterns may be deposited on the outer surfaces of the plates to provide more uniform heating, for example by having denser resistors at the extremities and thinner resistors in the middle. Although it is presently preferred to deposit a heating element on the outer surface of each plate, a heating element may alternatively be baked inside of each plate, particularly if the plates are ceramic. The heating element 206 may comprise metals, tungsten, polysilicon, or other materials that heat when a voltage difference is applied across the material. The heating element 206 has two ends which are connected to respective contacts 204 which are in turn connected to a voltage source (not shown in FIG. 24) to cause a current to flow through the heating element. Each plate 190 also preferably includes a temperature sensor 192, such as a thermocouple, thermistor, or RTD, which is connected by two traces 202 to respective ones of the contacts 204. The temperature sensor 192 is be used to monitor the temperature of the plate 190 in a controlled feedback loop.

Figure 29:
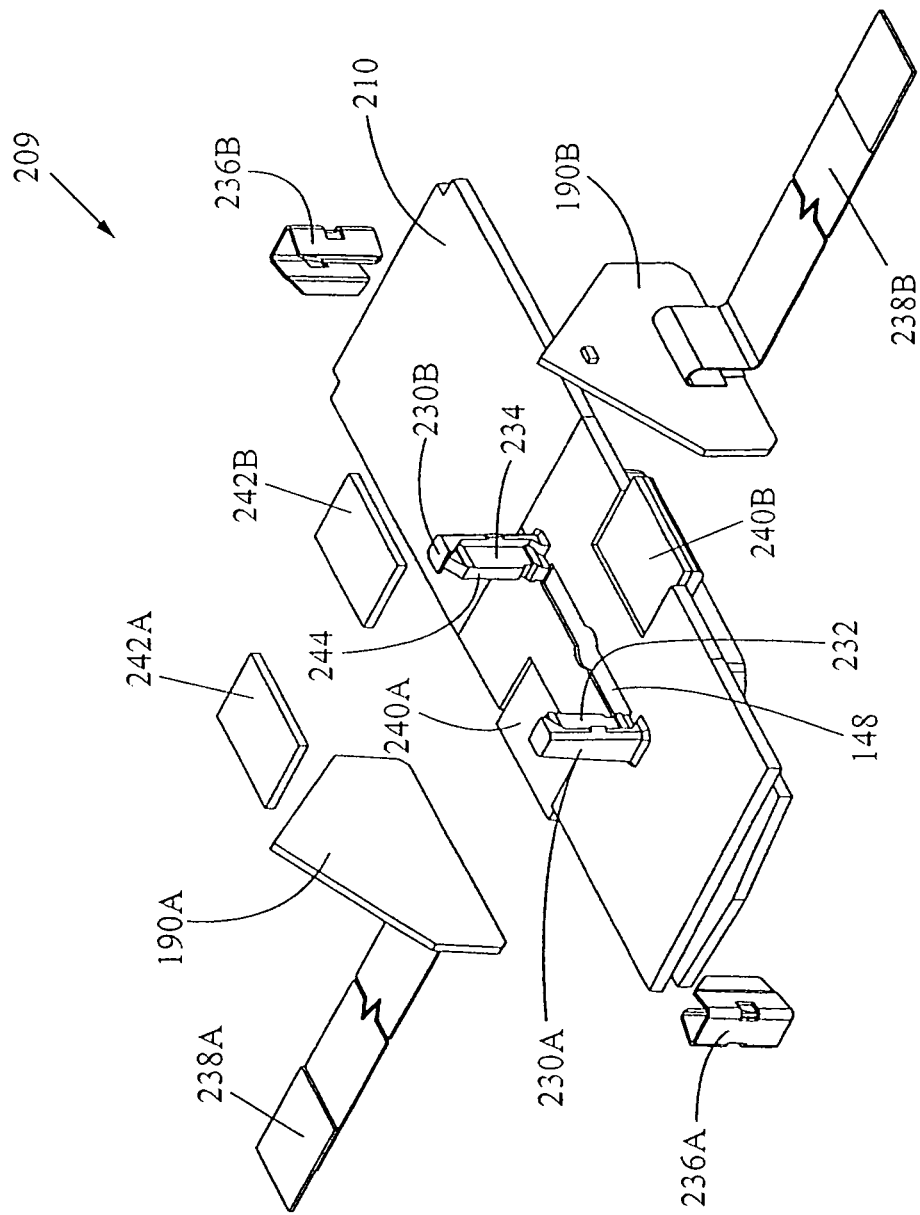
FIG. 29 is an exploded view of a support structure for holding the plates of FIG. 23.
Figure 30:
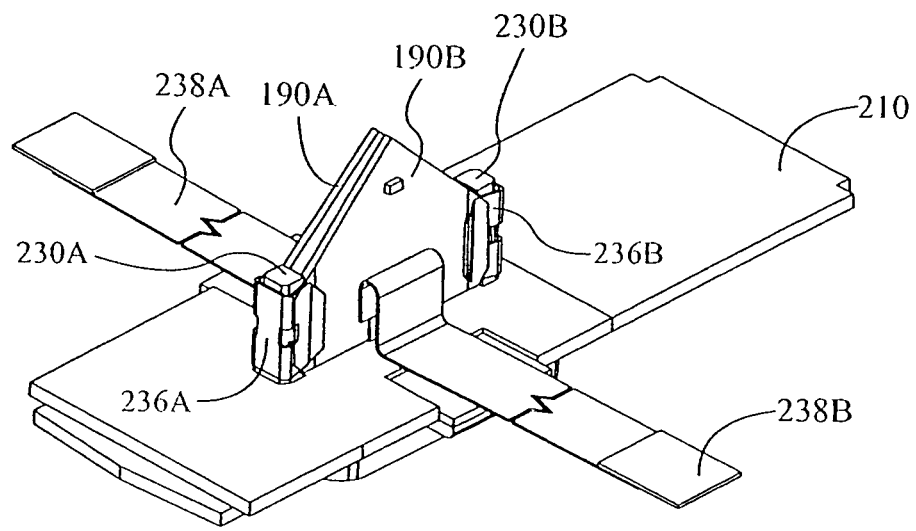
FIGS. 30-31 are assembled views of the support structure of FIG. 29.

The plates have a low thermal mass to enable rapid heating and cooling of the plates. In particular, it is presently preferred that each of the plates has a thermal mass less than about 5 J/° C., more preferably less than 3 J/° C., and most preferably less than 1 J/° C. As used herein, the term thermal mass of a plate is defined as the specific heat of the plate multiplied by the mass of the plate. In addition, each plate should be large enough to cover a respective major wall of the reaction chamber. In the presently preferred embodiment, for example, each of the plates has a width X in the range of 2 to 22 mm, a length Y in the range of 2 to 22 mm, and a thickness in the range of 0.5 to 5 mm. The width X and length Y of each plate is selected to be slightly larger than the width and length of the reaction chamber. Moreover, each plate preferably has an angled bottom portion matching the geometry of the bottom portion of the reaction chamber, as previously described with reference to FIG. 34. Also in the preferred embodiment, each of the plates is made of aluminum nitride having a specific heat of about 0.75 J/g ° C. The mass of each plate is preferably in the range of 0.005 to 5.0 g so that each plate has a thermal mass in the range of 0.00375 to 3.75 J/° C. The opposing plates 190 are positioned to receive the chamber of the vessel 40 between them such that the flexible major walls of the chamber contact and conform to the inner surfaces of the plates. It is presently preferred that the plates 190 be held in an opposing relationship to each other using, e.g., brackets, supports, or retainers. Alternatively, the plates 190 may be spring-biased towards each other as described in International Publication Number WO 98/38487, the disclosure of which is incorporated by reference herein. In another embodiment of the invention, one of the plates is held in a fixed position, and the second plate is spring-biased towards the first plate. If one or more springs are used to bias the plates towards each other, the springs should be sufficiently stiff to ensure that the plates are pressed against the flexible walls of the vessel with sufficient force to cause the walls to conform to the inner surfaces of the plates. FIGS. 29-30 illustrate a preferred support structure 209 for holding the plates 190A, 1 90B in an opposing relationship to each other. FIG. 29 shows an exploded view of the structure, and FIG. 30 shows an assembled view of the structure. For clarity of illustration, the support structure 209 and plates 190A, 190B are shown upside down relative to their normal orientation in the heat-exchanging module of FIG. 28. Referring to FIG. 29, the support structure 209 includes a mounting plate 210 having the slot 148 formed therein. The slot 148 is sufficiently large to enable the chamber of the vessel to be inserted through it. Spacing posts 230A, 230B extend from the mounting plate 210 on opposite sides of the slot 148. Spacing post 230A has indentations 232 formed on opposite sides thereof (only one side visible in the isometric view of FIG. 29), and spacing post 230B has indentations 234 formed on opposite sides thereof (only one side visible in the isometric view of FIG. 29). The indentations 232, 234 in the spacing posts are for receiving the edges of the plates 190A, 1 90B. To assemble the structure, the plates 1 90A, 1 90B are placed against opposite sides of the spacing posts 230A, 230B such that the edges of the plates are positioned in the indentations 232, 234. The edges of the plates are then held in the indentations using a suitable retention means. In the preferred embodiment, the plates are retained by retention clips 236A, 236B. Alternatively, the plates 190A, 190B may be retained by adhesive bonds, screws, bolts, clamps, or any other suitable means.

The mounting plate 210 and spacing posts 230A, 230B are preferably integrally formed as a single molded piece of plastic. The plastic should be a high temperature plastic, such as polyetherimide, which will not deform of melt when the plates 190A, 190B are heated. The retention clips 230A, 230B are preferably stainless steel. The mounting plate 210 may optionally include indentations 240A, 240B for receiving flex cables 238A, 238B, respectively, that connect the heating elements and temperature sensors disposed on the plates 190A, 190B to the PC board 226 of the heat-exchanging module 147 (FIG. 28). The portion of the flex cables 238A adjacent the plate 190A is held in the indentation 240A by a piece of tape 242A, and the portion of the flex cables 238B adjacent the plate 190B is held in the indentation 240B by a piece of tape 242B.

Figure 31:
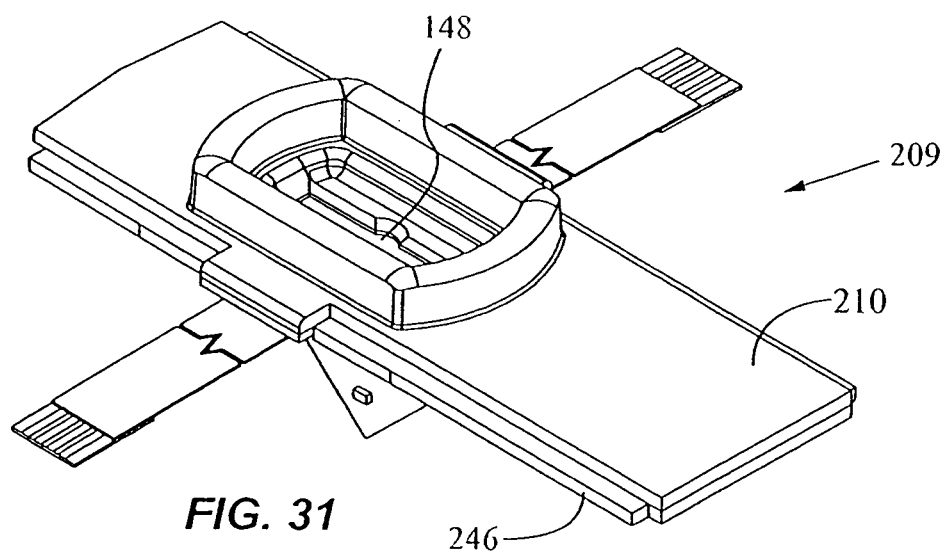

FIG. 31 is an isometric view of the assembled support structure 209. The mounting plate 210 preferably includes tabs 246 extending from opposite sides thereof for securing the structure 209 to the housing of the heat-exchanging module. Referring again to FIG. 28, the housing 208 preferably includes slots for receiving the tabs to hold the mounting plate 210 securely in place. Alternatively, the mounting plate 210 may be attached to the housing 208 using, e.g., adhesive bonding, screws, bolts, clamps, or any other conventional means of attachment.

Referring again to FIG. 29, the support structure 209 preferably holds the plates 190A, 190B so that their inner surfaces are angled very slightly towards each other. In the preferred embodiment, each of the spacing posts 230A, 230B has a wall 244 that is slightly tapered so that when the plates 190A, 190B are pressed against opposite sides of the wall, the inner surfaces of the plates are angled slightly towards each other. As best shown in FIG. 23, the inner surfaces of the plates 190A, 190B angle towards each other to form a slightly V-shaped slot into which the chamber 42 is inserted. The amount by which the inner surfaces are angled towards each other is very slight, preferably about 1° from parallel. The surfaces are angled towards each other so that, prior to the insertion of the chamber 42 between the plates 190A, 190B, the bottoms of the plates are slightly closer to each other than the tops. This slight angling of the inner surfaces enables the chamber 42 of the vessel to be inserted between the plates and withdrawn from the plates more easily. Alternatively, the inner surfaces of the plates 190A, 190B could be held parallel to each other, but insertion and removal of the vessel 40 would be more difficult.

In addition, the inner surfaces of the plates 190A, 190B are preferably spaced from each other a distance equal to the thickness of the frame 46. In embodiments in which the inner surfaces are angled towards each other, the centers of the inner surfaces are preferably spaced a distance equal to the thickness of the frame 46 and the bottoms of the plates are initially spaced a distance that is slightly less than the thickness of the frame 46. When the chamber 42 is inserted between the plates 190A, 190B, the rigid frame 46 forces the bottom portions of the plates apart so that the chamber 42 is firmly sandwiched between the plates. The distance that the plates 190A, 190B are wedged apart by the frame 46 is usually very small, e.g., about 0.035 mm if the thickness of the frame is 1 mm and the inner surfaces are angled towards each other by 1°.

Referring again to FIG. 30, the retention clips 236A, 236B should be sufficiently flexible to accommodate this slight outward movement of the plates 190A, 190B, yet sufficiently stiff to hold the plates within the recesses in the spacing posts 230A, 230B during insertion and removal of the vessel. The wedging of the vessel between the plates 190A, 190B provides an initial preload against the chamber and ensures that the flexible major walls of the chamber, when pressurized, establish good thermal contact with the inner surfaces of the plates.

Figure 32:
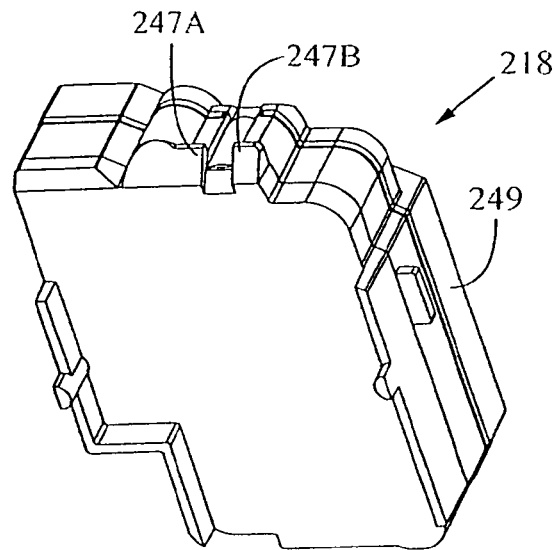
FIG. 32 is an isometric view showing the exterior of one the optics assemblies in the heat-exchanging module of FIG. 28.
Figure 33:
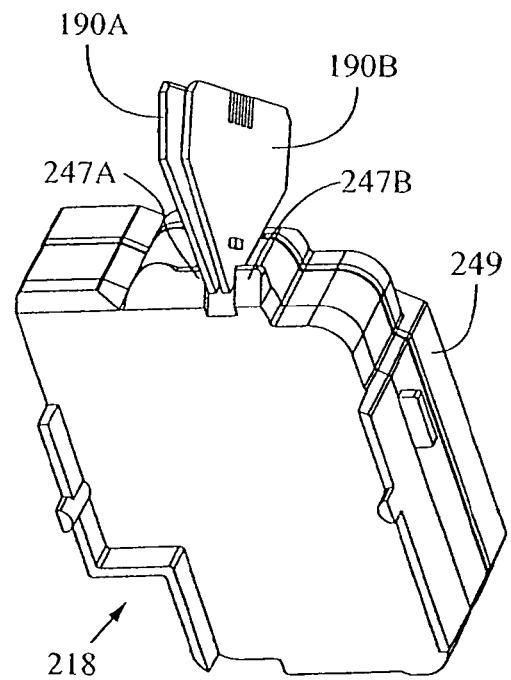
FIG. 33 is an isometric view of the plates of FIG. 23 in contact with the optics assembly of FIG. 32.

Referring again to FIG. 28, to limit the amount that the plates 190 can spread apart due to the pressurization of the vessel 40, stops may be molded into the housings of optics assemblies 216, 218. As shown in FIG. 32, the housing 249 of the optics assembly 218 includes claw-like stops 247A, 247B that extend outwardly from the housing. As shown in FIG. 33, the housing 249 is positioned such that the bottom edges of the plates 190A, 190B are inserted between the stops 247A, 247B. The stops 247A, 247B thus prevent the plates 190A, 190B from spreading farther than a predetermined maximum distance from each other. Although not shown in FIG. 33 for illustrative clarity, the optics assembly 216 (see FIG. 28) has a housing with corresponding stops for preventing the other halves of the plates from spreading farther than the predetermined maximum distance from each other. Referring again to FIG. 23, the maximum distance that stops permit the inner surfaces of the plates 190A, 190B to be spaced from each other should closely match the thickness of the frame 46. Preferably, the maximum spacing of the inner surfaces of the plates 190A, 190B is slightly larger than the thickness of the frame 46 to accommodate tolerance variations in the vessel 40 and plates 190A, 190B. For example, the maximum spacing is preferably about 0.1 to 0.3 mm greater than the thickness of the frame 46.

Figure 35:
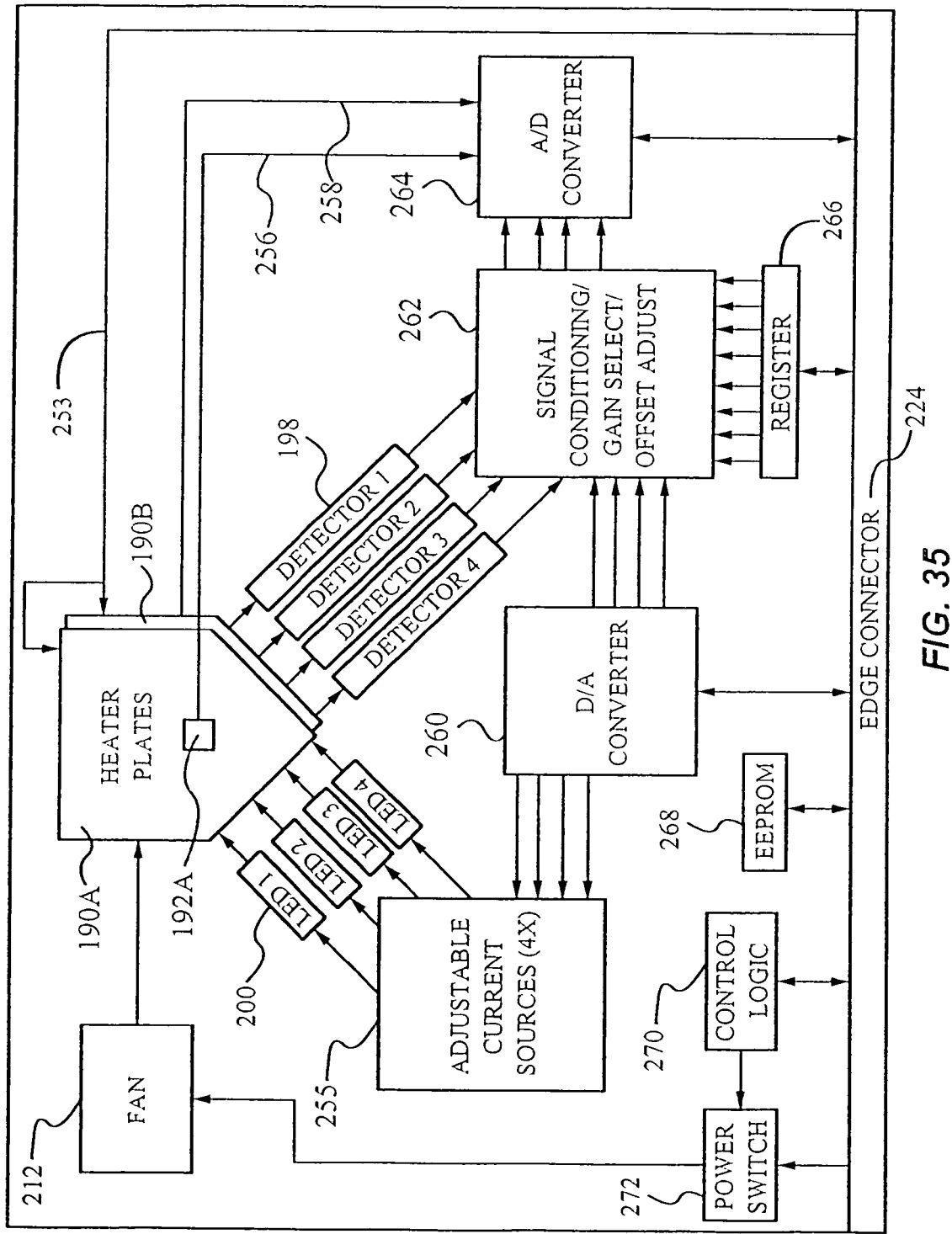
FIG. 35 is a schematic block diagram of the electronics of the heat-exchanging module of FIG. 28.

FIG. 35 is a schematic, block diagram of the electronic components of the heat-exchanging module 147. The module includes a connector 224 or flex cable for connection to the main logic board of the instrument. The module also includes heater plates 190A, 190B each having a resistive heating element as described above. The plates 190A, 190B are wired in parallel to receive power input 253 from the instrument. The plates 190A, 190B also include temperature sensors 192A, 192B that output analog temperature signals to an analog-to-digital converter 264. The converter 264 converts the analog signals to digital signals and routes them to the microcontroller in the instrument through the connector 224.

The heat-exchanging module also includes a cooling system, such as a fan 212, for cooling the plates 190A, 190B and the reaction mixture contained in the vessel inserted between the plates. The fan 212 is activated by switching a power switch 272, which is in turn controlled by a control logic block 270 that receives control signals from the microcontroller. The module further includes four light sources, such as LEDs 200, for excitation of labeled analytes in the reaction mixture and four detectors 198, preferably photodiodes, for detecting fluorescent emissions from the reaction mixture. The module also includes an adjustable current source 255 for supplying a variable amount of current (e.g., in the range of 0 to 30 mA) to each LED to vary the brightness of the LED. A digital-to-analog converter 260 is connected between the adjustable current source 255 and the microcontroller to permit the microcontroller to adjust the current source digitally.

The adjustable current source 255 is preferably used to ensure that each LED has about the same brightness when activated. Due to manufacturing variances, many LEDs have different brightnesses when provided with the same amount of current. Therefore, it is presently preferred to test the brightness of each LED during manufacture of the heat-exchanging module and to store calibration data in a memory 268 of the module. The calibration data indicates the correct amount of current to provide to each LED. The microcontroller reads the calibration data from the memory 268 and controls the current source 255 accordingly.

The module additionally includes a signal conditioning/gain select/offset adjust block 262 comprised of amplifiers, switches, electronic filters, and a digital-to-analog converter. The block 262 adjusts the signals from the detectors 198 to increase gain, offset, and reduce noise. The microcontroller controls block 262 through a digital output register 266. The output register 266 receives data from the microcontroller and outputs control voltages to the block 262. The block 262 outputs the adjusted detector signals to the microcontroller through the analog-to-digital converter 264 and the connector 224. The module also includes the memory 268, preferably a serial EEPROM, for storing data specific to the module, such as calibration data for the LEDs 200, thermal plates 190A, 190B, and temperature sensors 192A, 192B.

The operation of the cartridge and instrument will now be described. As shown in FIG. 3, a fluid sample to be analyzed is added to the sample chamber 65 through the sample port 64 and the cap 30 screwed into the port 64 to seal the port shut. Referring to FIG. 10, the cartridge 20 is then placed into the cartridge nest 141 of the instrument 140 for processing. All valves in the cartridge 20 are initially closed when the cartridge is placed into the instrument 140. When the cartridge is placed in the instrument, the transducer 92 contacts an external surface of the flexible gasket 63 forming the bottom wall of the lysing chamber 86, as shown in FIG. 5.

Referring again to FIG. 10, the instrument 140 is preferably computer-controlled to perform the functions described in the following section, e.g., opening and closing valves in the cartridge using valve actuators 142, providing pressure to the cartridge through nozzles 145, activating the transducer 92, sensing liquid presence or liquid levels using optical sensors 143 and 144, and controlling the heat-exchanging and optical detection module 147. A programmer having ordinary skill in the art will be able to program a microcontroller and/or computer to perform these functions based upon the following description.

Referring to FIG. 9, liquids are preferably forced to flow through the cartridge using differential pressure. Although positive pressure is described herein, negative pressure (vacuum) may also be used to control fluid flow in the cartridge. The maximum amount of positive pressure that can be applied is usually limited by the hydrophobic membranes which may reach liquid break-through pressure above 30 pounds per square inch (psi). The lower limit of pressure is limited by the need to move sample and other fluids through the cartridge sufficiently quickly to meet assay goals. Below 1 psi, for example, sample may not flow efficiently through the filter stack 87. Pressure in the range of 6 to 20 psi is generally adequate. The sample flow rate through the cartridge is preferably in the range of 10 to 30 ml/minute. The wash flow rate may be slower, e.g. 6 to 18 ml/minute so that the wash effectively washes the lysing chamber 86.

A specific protocol will now be described with reference to FIG. 9 to illustrate the operation of the cartridge. It is to be understood that this is merely an example of one possible protocol and is not intended to limit the scope of the invention. To begin, the cartridge is preferably primed with wash solution from the wash chamber 66 before the fluid sample is forced to flow from the sample chamber 65. To prime the cartridge, valves 111 and 115 are opened and a pressure of 10 psi is applied to the chamber 66 through the pressure port 116 for about two seconds. A small portion of the wash solution flows through the channels 117 and 106, through the lysing chamber 86, through the channels 109 and 110, into the U-shaped channel 122, and all the way to the hydrophobic membrane below the pressure port 128.

Following priming, valve 115 and pressure port 116 are closed and valves 107 and 114 are opened. At the same time, a pressure of 20 psi is applied to the sample chamber 65 through the pressure port 105 for about 15 seconds to force the sample to flow through the channel 106, through the filter stack 87 in the chamber 87, through the channels 110, 111, 112 and into the vented waste chamber 68. As the sample passes the detection region 136 in the channel 106, the reflective optical sensor 144 (FIG. 13) may be used to determine when the sample chamber 65 has been emptied. As the sample liquid flows through the filter stack 87, target cells or viruses in the sample are captured. When a predetermined volume of sample reaches the waste chamber 68, some of the liquid spills over into the sensor chamber 120, triggering the next step in the protocol. Alternatively, instead of using feedback from optical sensors to trigger events, the steps in a predetermined protocol may simply be timed, e.g., applying predetermined pressures for predetermined durations of time to move known volumes of fluid at known flow rates.

The flow-through design of the lysing chamber 86 permits target cells or viruses from a relatively large sample volume to be concentrated into a much smaller volume for amplification and detection. This is important for the detection of low concentration analyte in the sample, such as nucleic acid. In particular, the ratio of the volume of the sample forced to flow through the lysing chamber 86 to the volume capacity of the chamber 86 is preferably at least 2:1, and more preferably at least 5:1. The volume of sample forced to flow through the chamber 86 is preferably at least 100 □l, and more preferably at least 1 ml. In the presently preferred embodiment, a sample volume of 5 ml is forced to flow through the lysing chamber 86, and the chamber 86 has a volume capacity of about 0.5 ml, so that the ratio is 10:1. In addition, the lysing chamber 86 may be sonicated (e.g., using an ultrasonic horn coupled to a wall of the chamber) as the sample is forced to flow through the chamber. Sonicating the chamber 86 helps to prevent clogging of the filter stack 87, providing for more uniform flow through the chamber 86. In particular, the sound waves help keep particulate matter or the beads in the filter stack from clogging one or more filters.

In the next step, valves 111, 114, 115 are opened and a pressure of 20 psi is applied to the wash chamber 66 for about seven seconds to force the wash solution to flow through the channels 117 and 106 into the lysing chamber 86. The washing solution washes away PCR inhibitors and contaminants from the lysing chamber 86 and carries then through the channels 109, 110, and 112 into the waste chamber 68. A variety of suitable wash solutions of varying pH, solvent composition, and ionic strength may be used for this purpose and are well known in the art. For example, a suitable washing reagent is a solution of 80mM potassium acetate, 8.3 mM Tris-HCl, pH 7.5, 40 uM EDTA, and 55% ethanol. The lysing chamber 86 may be sonicated (e.g., using an ultrasonic horn coupled to a wall of the chamber) while the wash solution is forced to flow through the chamber. Sonicating the chamber 86 helps to prevent clogging of the filter stack 87, providing for more uniform flow through the chamber 86 as previously described. In addition, the sound waves may help loosen the material to be washed away. When the incremental volume of wash solution reaches the waste chamber 68, some of the liquid spills over into the sensor chamber 121, triggering the next step in the protocol.

In the next step, valve 115 is closed and valve 119 is opened while a pressure of 15 psi is applied to the reagent chamber 67 through the pressure port 118 for about three seconds. The pressure forces lysing reagent to flow from the chamber 67 through the channels 117, 106 into the lysing chamber 86, and into the channel 110. The chamber 86 is thus filled with liquid. Suitable lysing reagents include, e.g., solutions containing a chaotropic salt, such as guanidine HCl, guanidine thiocyanate, guanidine isothiocyanate, sodium iodide, urea, sodium perchlorate, and potassium bromide. In the presently preferred embodiment, a lysing reagent that is not inhibitory to PCR is used. The lysing reagent comprises 10 mM tris, 5% tween–20, 1 mM tris (2-carboxyethyl phosphine hydrochloride), 0.1 mM Ethylene Glycol-bis(b-amino-ethylether)-N, N,N',N'-tetracetic acid. After the lysing chamber 86 is filled with lysing reagent, the valves 111, 114 are closed. Valve 119 remains open and a pressure of 20 psi is applied to pressure port 118. The static pressure in the lysis chamber 86 is therefore increased to 20 psi in preparation for the lysis of the cells or viruses trapped in the filter stack 87.

Referring again to FIG. 5, the pressurization of the lysing chamber 86 is important because it ensures effective coupling between the transducer 92 and the flexible wall 63 of the lysing chamber 86. To disrupt the cells or viruses in the chamber 86, the transducer 92 is activated (i.e., set into vibratory motion). The flexible wall 63 of the lysing chamber 86 transfers the vibratory motion of the transducer 92 to the liquid in the chamber 86 by allowing slight deflections without creating high stresses in the wall. The wall 63 may be formed by the elastomeric membrane as previously described. Alternatively, the wall may be a film or sheet of polymeric material (e.g., a polypropylene film) preferably having a thickness in the range of 0.025 to 0.1 mm. The transducer 92 is preferably an ultrasonic horn for sonicating the chamber 86. The chamber 86 is preferably sonicated for 10 to 40 seconds at a frequency in the range of 20 to 60 kHz. In the exemplary protocol, the chamber is sonicated for 15 seconds at a frequency of 47 kHz. The amplitude of the horn tip is preferably in the range of 20 to 25 □nm (measured peak to peak).

As the tip of the transducer 92 vibrates, it repeatedly impacts the flexible wall 63. On its forward stroke (in the upward direction in FIG. 6), the tip of the transducer 92 pushes the wall 63 and creates a pressure pulse or pressure wave in the chamber 86. On its retreating stroke (downward in FIG. 5), the tip of the transducer 92 usually separates from the flexible wall 63 because the flexible wall 63 cannot move at the same frequency as the transducer. On its next forward stroke, the tip of the transducer 92 once again impacts the wall 63 in a head-on collision as the tip and wall speed towards each other. Because the transducer 92 and the wall 63 separate as the transducer 92 vibrates, the effective forward stroke of the transducer is less than its peak-to-peak amplitude. The effective forward stroke determines the level of sonication in the chamber 86. It is therefore important to increase the static pressure in the lysing chamber 86 so that when the tip of the transducer 92 retreats, the flexible wall 63 is forced outwardly to meet the tip on its return stroke. The static pressure in the chamber 86 should be sufficient to ensure that the effective forward stroke of the transducer 92 generates pressure pulses or pressure waves in the chamber 86. It is presently preferred to increase the static pressure in the chamber 86 to at least 5 psi above the ambient pressure external to the cartridge, and more preferably to a pressure in the range of 15 to 25 psi above the ambient pressure.

On each forward stroke, the transducer 92 imparts a velocity to the liquid in the chamber 86, thus creating a pressure pulse that quickly sweeps across the chamber 86.

The beads in the filter stack 87 (FIG. 6) are agitated by the pressure pulses in the chamber 86. The pressure pulses propel the beads into violent motion in the chamber 86, and the beads mechanically rupture the cells or viruses to release the material (e.g., nucleic acid) therefrom. It should be noted that some types of cells, such as blood cells, are relatively weak and may be disrupted using only pressure pulses without the use of beads. Other types of cells (particularly spores) have highly resistant cell walls and beads are generally required for effective lysis.

Referring again to FIG. 9, following disruption of the cells or viruses, valves 111, 124 are opened and a pressure of 12 psi is delivered for about 4 seconds to the reagent chamber 67 through the pressure port 118. The pressure forces the lysis reagent to elute the nucleic acid from the filter stack 87 and to flow with the nucleic acid into the neutralization chamber 70. The lysing chamber 86 may be sonicated (e.g., using an ultrasonic horn coupled to a wall of the chamber) while the eluting the nucleic acid. Sonicating the chamber 86 may help prevent clogging of the filter stack 87, as previously described. The chamber 420 is partially filled (e.g., half-filled) with neutralizer, such as detergent, for neutralizing the lysing reagent. If a lysing reagent non-inhibitory to PCR is used, the neutralizer is optional.

In the next step, the valve 124 is closed to hold the lysing reagent, analyte, and neutralizer in the chamber 70. The valve 114 is opened and a pressure of 15 psi is applied for about three seconds through the pressure port 128 to force any liquid in the U-shaped channel 122 to flow into the waste chamber 68. Next, valves 124 and 126 are opened and a pressure of 15 psi is applied for about five seconds through the pressure port 123 on top of the neutralizer chamber 70. The pressure forces the neutralized lysing reagent and nucleic acid in the chamber 70 to flow into the channel 122 and into the master mix chamber 71. The valve 126 to the master mix chamber 71 is then closed. The master mix chamber contains PCR reagents and fluorescent probes that mix with the neutralized lysing reagent and nucleic acid to form a reaction mixture.

In the next step, the channel 122 is cleared by opening valve 114 to waste chamber 68 and applying a pressure of 15 psi for about one second to pressure port 128. In the next step, the reaction mixture formed in the master mix chamber 71 is moved into the reaction vessel 40 as follows. Valves 126, 127, and 133 are opened and a pressure of 15 psi is applied for about six seconds to the pressure port 125 on top of the master mix chamber 71 to force the reaction mixture to flow through the channel 122, valve 127, and channel 80 into the reaction vessel 40 through the port 41. The reaction mixture fills the chamber 42 of the vessel, displacing air in the chamber which exits through the outlet channel 52. The air escaping through the outlet channel 52 travels in channel 81 past sensor region 130 and into channel 131. From channel 131, the air flows into channel 132, through valve 133, channel 134, and exits the cartridge through the vent 36. When a volume of reaction mixture sufficient to fill the chamber 42 has flowed into the vessel, excess reaction mixture exits the vessel through the outlet channel 52. The excess reaction mixture flows into channel 81 and is optically detected in the sensor region 130. When the reaction mixture is detected, valve 133 is closed while pressure from the pressure port 125 is applied to pressurize the reaction chamber 42.

Referring again to FIG. 23, the pressurization of the chamber 42 expands the flexible major walls 48 of the vessel. In particular the pressure forces the major walls 48 to contact and conform to the inner surfaces of the plates 190A, 190B. This ensures optimal thermal conductance between the plates 190A, 190B and the reaction mixture in the chamber 42. It is presently preferred to pressurize the chamber 42 to a pressure in the range of 2 to 30 psi above ambient pressure. This range is presently preferred because 2 psi is generally enough pressure to ensure conformity between the walls 48 and the surfaces of the plates 190A, 190B, while pressures above 30 psi may cause bursting of the walls 48, deformation of the frame 46 or plates 190A, 190B, or bursting of the hydrophobic membranes in the cartridge. More preferably, the chamber 42 is pressurized to a pressure in the range of 8 to 15 psi above ambient pressure. This range is more preferred because it is safely within the practical limits described above. When the chamber 42 is pressurized, the reaction mixture in the vessel 40 is thermally processed and optically interrogated to determine the presence or absence of a target analyte in the mixture.

Referring again to FIG. 35, the reaction mixture is thermally processed between the plates 190A, 190B using standard proportional-integral-derivative (PID) control using target temperatures and feedback signals from the temperature sensors 192A, 192B. Proportioning may be accomplished either by varying the ratio of "on" time to "off" time, or, preferably with proportional analog outputs which decrease the average power being supplied either to the heating elements on the plates 190A, 190B or to the fan 212 as the actual temperature of the plates 190A, 190B approaches the desired set point temperature. PID control combines the proportional mode with an automatic reset function (integrating the deviation signal with respect to time) and rate action (summing the integral and deviation signal to shift the proportional band).

Standard PID control is well known in the art and need not be described further herein. Alternatively, the reaction mixture may be thermally processed using a modified version of PID control described in International Publication Number WO 99/48608 (Application Number PCT/US99/06628) the disclosure of which is incorporated by reference herein.

As the reaction mixture is thermally cycled between the heater plates 190A, 190B to amplify one or more target nucleic acid sequences in the mixture, the mixture is optically interrogated, preferably at the lowest temperature point in each cycle. Optical interrogation is accomplished by sequentially activating each of the LEDs 200 to excite different fluorescently-labeled analytes in the mixture and by detecting light emitted (fluorescent output) from the chamber 42 using detectors the 198. Referring again to FIG. 22, excitation beams are preferably transmitted to the chamber 42 through the optically transmissive side wall 57A, while fluorescent emission is detected through the side wall 57B.

One advantage of the cartridge of the present invention is that it allows the intracellular material from a relatively large volume of fluid sample, e.g. several milliliters or more, to be separated from the sample and concentrated into a much smaller volume of reaction fluid, e.g., 100 μl or less. The cartridge permits extraordinary concentration factors by efficiently extracting material from milliliter quantities of fluid sample. In particular, the sample chamber 65 preferably has a volume capacity in the range of 100 μl to 12 ml. More preferably, the sample chamber 65 has a volume capacity of at least 1 ml. The lower limit of 1 ml is preferred because at least 1 ml of sample should be analyzed to detect low concentration analytes such as nucleic acid. The upper limit of 12 ml is preferred because a sample volume greater than 12 ml would require a much larger cartridge and likely clog the filter stack. In the presently preferred embodiment, the sample chamber has a volume capacity of 5.5 ml for holding 5 ml of sample.

The wash chamber 66 has a volume capacity proportional to the volume of the lysing chamber 86. In particular, the wash chamber 66 preferably holds a volume of wash that is at least one to two times the volume of the lysing chamber 86 to ensure that there is enough wash solution to wash out PCR inhibitors and debris from the chamber 86. In the presently preferred embodiment, the volume of the lysing chamber 86 is about 0.5 ml and the volume of the wash chamber 66 is 2.5 ml for holding 2 ml of wash solution. The lysing chamber volume of 0.5 ml is a compromise between a size large enough to avoid clogging of the filter stack 87 and a size small enough to concentrate analyte into a small volume for improved amplification and detection.

The reagent chamber 67 preferably holds a volume of lysing reagent that is at least one to two times the volume of the lysing chamber 86 so that there is sufficient lysing reagent to pressurize the chamber and to elute nucleic acid from the chamber. In the presently preferred embodiment, the chamber 67 has a volume capacity of 1.5 ml for holding about 1 to 1.5 ml of lysing reagent. The waste chamber 68 has a volume capacity sufficient to hold the sample, wash solution, and unused lysing reagent. The waste chamber 68 is sized at 9.5 ml volume capacity in the preferred embodiment.

The size of the neutralization chamber 70 is dependent upon the volume of the lysing chamber 86 since the neutralizer in the chamber 70 neutralizes the volume of lysing reagent that fills the lysing chamber 86. It is currently preferred that the lysing chamber have a volume if 0.5 ml, so the chamber 70 has a volume capacity of 1.0 ml for holding about 0.5 ml of neutralizer that is mixed with 0.5 ml of the lysing reagent and eluted analyte. The volume capacity of the master mix chamber 71 should be sufficient to produce a reaction mixture to fill the vessel 40 and the channels 122, 127 leading to the vessel. In the presently preferred embodiment, the master mix chamber has a volume capacity of 200 μl for holding an initial load of 100 μl of master mix to which is added 100 μl of neutralized lysing reagent and eluted analyte to form the reaction mixture.

The flow channels in the cartridge are generally D-shaped in cross section (with the gasket 63 forming the flat side of the channel) and preferably have a width or diameter in the range of 1/64 to 1/8 of an inch (0.4 to 3.2 mm), and more preferably a width of 1/32 to 1/16 of an inch (0.8 to 1.6 mm). These ranges are presently preferred to avoid having channels to narrow (which creates flow restriction) and to avoid having channels too wide (which yields unused volumes of liquid sitting in the flow path).

Many modifications to the structure and operation of the cartridge and instrument are possible in alternative embodiments. For example, although amplification by PCR is presently preferred, the cartridge and instrument may be used to amplify nucleic acid sequences using any amplification method, including both thermal cycling amplification methods and isothermal amplification methods. Suitable thermal cycling methods include, but are not limited to, the Polymerase Chain Reaction (PCR; U.S. Pat. Nos. 4,683,202, 4,683,195 and 4,965,188); Reverse Transcriptase PCR (RT-PCR); DNA Ligase Chain Reaction (LCR; International Patent Application No. WO 89/09835); and transcription-based amplification (D. Y. Kwoh et al. 1989, Proc. Natl. Acad. Sci. USA 86, 1173-1177). Suitable isothermal amplification methods useful in the practice of the present invention include, but are not limited to, Rolling Circle Amplification; Strand Displacement Amplification (SDA; Walker et al. 1992, Proc. Nati. Acad. Sci. USA 89, 392-396); Q-.beta. replicase (Lizardi et al. 1988, Bio/Technology 6, 1197-1202); Nucleic Acid-Based Sequence Amplification (NASBA; R. Sooknanan and L. Malek 1995, Bio/Technology 13, 563-65); and Self-Sustained Sequence Replication (3SR; Guatelli et al. 1990, Proc. Nati. Acad. Sci. USA 87, 1874-1878).

Moreover, the cartridge and instrument may be used to conduct chemical reactions other than nucleic acid amplification. Further, although fluorescence excitation and emission detection is preferred, optical detection methods such as those used in direct absorption and/or transmission with on-axis geometries may also be used to detect analyte in the cartridge. Another possible detection method is time decay fluorescence. Additionally, the cartridge is not limited to detection based upon fluorescent labels. For example, detection may be based upon phosphorescent labels, chemiluminescent labels, or electrochemiluminescent labels.

A fluid sample may be introduced into the cartridge by a variety of means, manual or automated. For manual addition, a measured volume of material may be placed into a receiving area of the cartridge through an input port and a cap is then placed over the port. Alternatively, a greater amount of sample material than required for the analysis can be added to the cartridge and mechanisms within the cartridge can effect the precise measuring and aliquoting of the sample needed for the specified protocol. It may be desirable to place certain samples, such as tissue biopsy material, soil, feces, exudates, and other complex material into another device or accessory and then place the secondary device or accessory into the cartridge. For example, a piece of tissue may be placed into the lumen of a secondary device that serves as the cap to the input port of the cartridge. When the cap is pressed into the port, the tissue is forced through a mesh that slices or otherwise divides the tissue.

For automated sample introduction, additional design features of the cartridge are employed and, in many cases, impart specimen accession functionality directly into the cartridge. With certain samples, such as those presenting a risk of hazard to the operator or the environment, such as human retrovirus pathogens, the transfer of the sample to the cartridge may pose a risk. Thus, in one embodiment, a syringe may be integrated into a device to provide a means for moving external fluidic samples directly into the cartridge. Alternatively, a venous puncture needle and an evacuated blood tube can be attached to the cartridge forming an assembly that can be used to acquire a sample of blood. After collection, the tube and needle are removed and discarded, and the cartridge is then placed in an instrument to effect processing. The advantage of such an approach is that the operator or the environment is not exposed to pathogens.

The input port can be designed with a consideration of appropriate human factors as a function of the nature of the intended specimen. For example, respiratory specimens may be acquired from the lower respiratory tract as expectorants from coughing, or as swab or brush samples from the back of the throat or the nares. In the former case, the input port can be designed to allow the patient to cough directly into the cartridge or to otherwise facilitate spitting of the expectorated sample into the cartridge. For brush or swab specimens, the specimen is placed into the input port where features of the port and closure facilitate the breaking off and retaining of the end of the swab or brush in the cartridge receiving area.

In another embodiment, the cartridge includes input and output tubes that may be positioned in a sample pool of very large volume, such as a flowing stream of water, so that the sample material flows through the cartridge. Alternatively, a hydrophilic wicking material can serve as an interactive region so that the entire cartridge can be immersed directly into the specimen, and a sufficient amount of specimen is absorbed into the wicking material. The cartridge is then removed, and can be transported to the laboratory or analyzed directly using a portable instrument. In another embodiment, tubing can be utilized so that one end of the tube is in direct communication with the cartridge to provide a fluidic interface with at least one interactive region and the other end is accessible to the external environment to serve as a receiver for sample. The tube can then be placed into a specimen and serve as a sipper. The cartridge itself may also serve as the actual specimen collection device, thereby reducing handling and inconvenience. In the case of specimens involved in legal disputes or criminal investigations, the direct accessing of the test material into the fluidic cartridge is advantageous because the chain of custody is conveniently and reliably preserved.

Referring again to FIG. 9, reagents may be exogenously introduced into the cartridge before use, e.g., through sealable openings in the reagent chamber 67, neutralizer chamber 70, and master mix chamber 71. Alternatively, the reagents may be placed in the cartridge during manufacture, e.g., as aqueous solutions or dried reagents requiring reconstitution. The particular format is selected based on a variety of parameters, including whether the interaction is solution-phase or solid-phase, the inherent thermal stability of the reagent, speed of reconstitution, and reaction kinetics. Reagents containing compounds that are thermally unstable when in solution can be stabilized by drying using techniques such as lyophilization. Additives, such as simple alcohol sugars, methylcelluloses, and bulking proteins may be added to the reagent before drying to increase stability or reconstitutability.

Referring again to FIG. 21, the reaction vessel 40 does not require two flexible sheets forming opposing major walls 48 of the reaction chamber 42. For example, in one alternative embodiment, the vessel 40 has only one flexible sheet forming a major wall of the chamber. The rigid frame 46 defines the other major wall of the chamber, as well as the side walls of the chamber. In this embodiment, the major wall formed by the frame 46 should have a minimum thickness of about 0.05 inches (1.25 mm) which is typically the practical minimum thickness for injection molding, while the flexible sheet may be as thin as 0.0005 inches (0.0125 mm). The advantage to this embodiment is that the manufacturing of the reaction vessel 40 is simplified, and hence less expensive, since only one flexible sheet need be attached to the frame 46. The disadvantage is that the heating and cooling rates of the reaction mixture are likely to be slower since the major wall formed by the frame 46 will probably not permit as high a rate of heat transfer as the thin, flexible sheet.

Referring to FIG. 28, the heat-exchanging module 147 only requires one thermal surface for contacting a flexible wall of the reaction vessel 40 and one thermal element for heating and/or cooling the thermal surface. The advantage to using one thermal surface and one thermal element is that the apparatus may be manufactured less expensively. The disadvantage is that the heating and cooling rates are likely to be about twice as slow. Further, although it is presently preferred that the thermal surfaces be formed by the thermally conductive plates 190, each thermal surface may be provided by any rigid structure having a contact area for contacting a wall of the vessel 40. The thermal surface preferably comprises a material having a high thermal conductivity, such as ceramic or metal. Moreover, the thermal surface may comprise the surface of the thermal element itself. For example, the thermal surface may be the surface of a thermoelectric device that contacts the wall to heat and/or cool the chamber.

It is presently preferred to build the transducer into the instrument 140. In another embodiment, however, the transducer may be built into the cartridge. For example, a piezoelectric disk may be built into the cartridge for sonicating the lysing chamber. Alternatively, a speaker or electromagnetic coil device may be built into the cartridge. In these embodiments, the cartridge includes suitable electrical connectors for connecting the transducer to a power supply. In embodiments in which the transducer is built into the cartridge, the transducer should be prevented from contacting the fluid sample directly, e.g., the transducer should be laminated or separated from the sample by a chamber wall. Further, lysis of the cells or viruses may be performed using a heater in place of or in combination with a transducer. The heater may be a resistive heating element that is part of cartridge, or the heater could be built into the instrument that receives the cartridge. In this embodiment, the cells or viruses are disrupted by heating the lysis chamber to a high temperature (e.g., 95° C.) to disrupt the cell walls.

Figure 36:
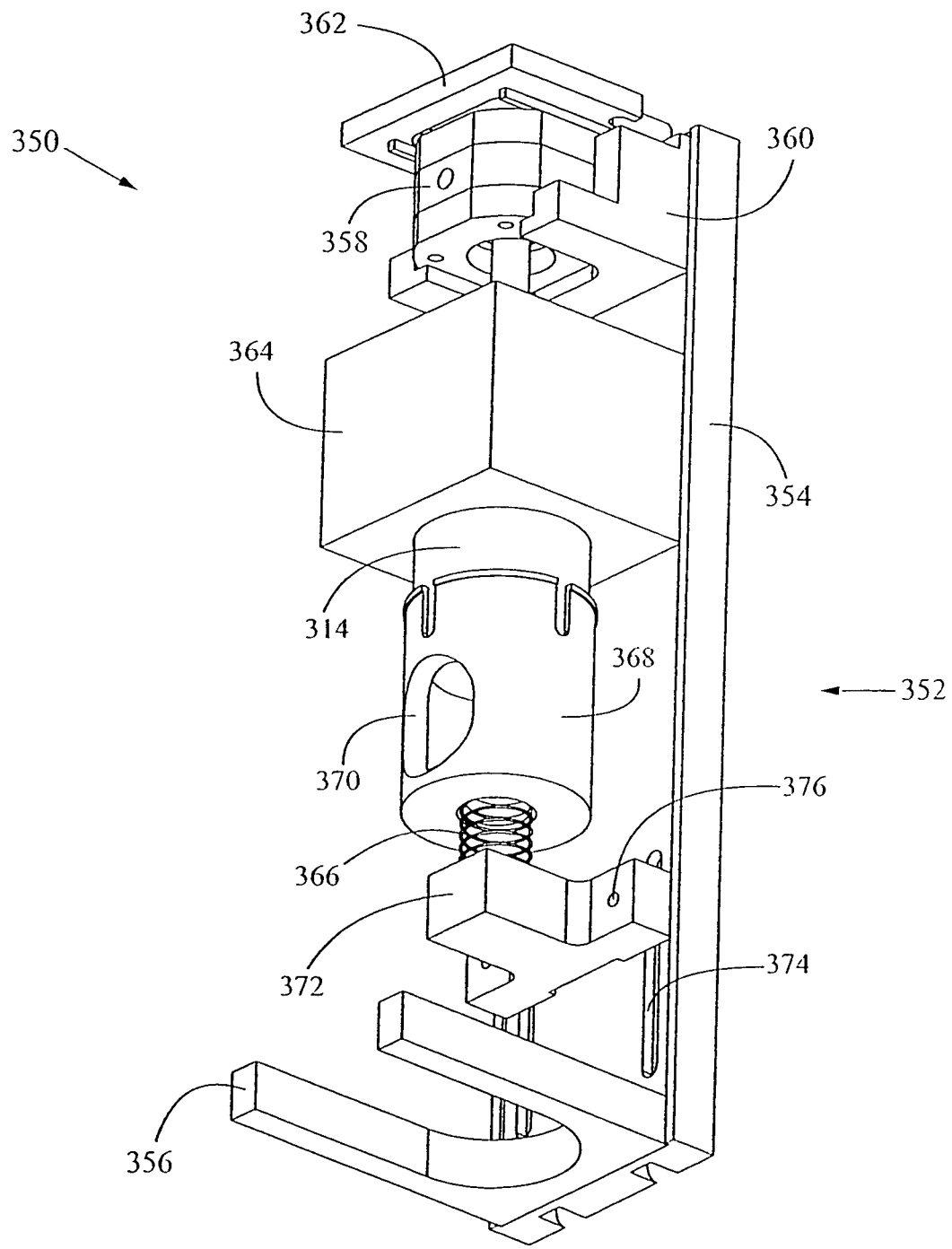
FIG. 36 is an isometric view of an apparatus for disrupting cells or viruses according to another embodiment of the invention.
Figure 37:
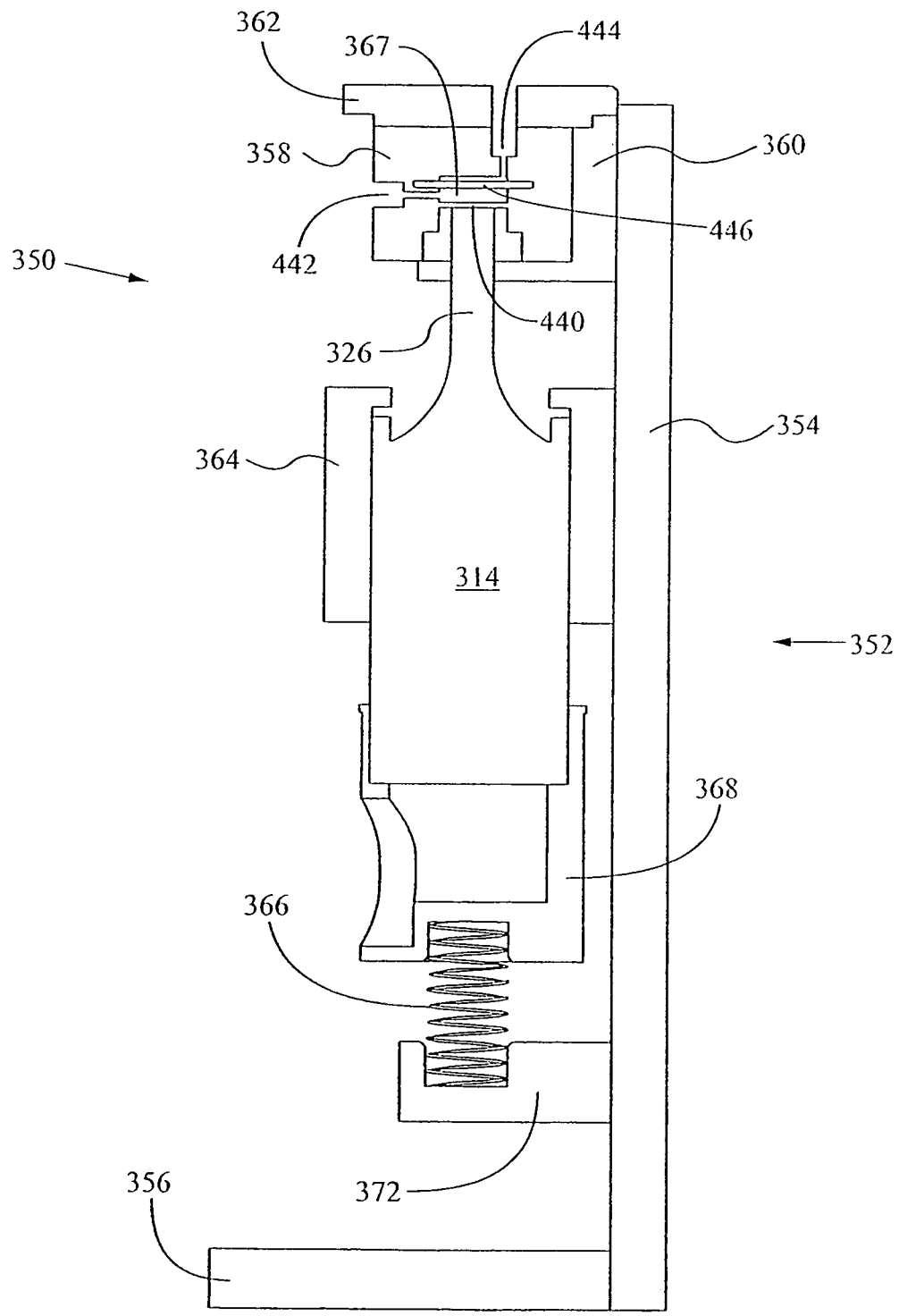
FIG. 37 is a cross sectional view of the apparatus of FIG. 36.

FIGS. 36-46 show another apparatus 350 for disrupting cells or viruses according to the present invention. FIG. 36 shows an isometric view of the apparatus 350, and FIG. 37 shows a cross sectional view of the apparatus 350. As shown in FIGS. 36-37, the apparatus 350 includes a cartridge or container 358 having a chamber 367 for holding the cells or viruses. The container includes a flexible wall 440 defining the chamber 367. In this embodiment, the flexible wall 440 is the bottom wall of the chamber 367. The flexible wall 440 is preferably a sheet or film of polymeric material (e.g., a polypropylene film) and the wall 440 preferably has a thickness in the range of 0.025 to 0.1 mm. The apparatus 350 also includes a transducer 314, such as an ultrasonic horn, for contacting an external surface of the flexible wall 440 (i.e., a surface of the wall 440 that is external to the chamber 367). The transducer 314 should be capable of vibratory motion sufficient to create pressure pulses in the chamber 367. Suitable transducers include ultrasonic, piezoelectric, magnetostrictive, or electrostatic transducers. The transducer may also be an electromagnetic device having a wound coil, such as a voice coil motor or a solenoid device.

The apparatus 350 further includes a support structure 352 for holding the container 358 and the transducer 314 against each other such that the transducer 314 contacts the wall 440 of the chamber 367 and for applying a substantially constant force to the container 358 or to the transducer 314 to press together the transducer 314 and the wall 440 of the chamber. The support structure 352 includes a base structure 354 having a stand 356. The transducer 314 is slidably mounted to the base structure 354 by a guide 364. The guide 364 is either integrally formed with the base structure 354 or fixedly attached to the base structure. The support structure 352 also includes a holder 360 attached to the base structure 354 for holding the container 358. The holder 360 has a U-shaped bottom portion providing access to the flexible wall 440 of the chamber 367. The guide 364 and the holder 360 are arranged to hold the transducer 314 and the container 358, respectively, such that the external surface of the wall 440 contacts the transducer 314. The support structure 352 also includes a top retainer 362 for the container 358. The retainer 362 is U-shaped to allow access to an exit port 444 formed in the container 358.

The support structure 352 further includes an elastic body, such as a spring 366, for applying a force to the transducer 314 to press the transducer 314 against the wall 440. When the transducer 314 is in contact with the wall 440, the force provided by the spring 366 is constant, providing for consistent coupling between the transducer 314 and the wall 440. The spring 366 is positioned between a spring guide 372 and the base of a coupler 368 that supports the bottom of the transducer 314. As shown in FIG. 36, the coupler 370 preferably has a window 370 through which the power cord (not shown) of the transducer 314 may be placed. Bolts or screws 376 hold the spring guide 372 in adjustment grooves 374 formed in the base structure 354. The magnitude of the force provided by the spring 366 may be adjusted by changing the preload on the spring. To adjust the preload on the spring 366, the bolts 376 holding the spring guide 372 are loosened, the guide 372 is moved to a new position, and the bolts 376 are retightened to hold the guide 372 in the new position. Once the preload on the spring 366 is adjusted to provide a suitable coupling force between the transducer 314 and the wall 440, it is desirable to keep the preload constant from one use of the apparatus 350 to the next so that valid comparisons can be made between different samples disrupted by the apparatus.

The magnitude of the force provided by the spring 366 to press together the transducer 314 and the wall 440 is important for achieving a consistent transfer of energy between the transducer 314 and the chamber 367. If the force is too light, the transducer 314 will only be held lightly against the wall 440, leading to poor translation of vibratory movement from the transducer 314 to the wall 440. If the force is too strong, the container 358 or wall 440 may be damaged during sonication. An intermediate force results in the most consistent and repeatable transfer of vibratory motion from the transducer 314 to the wall 440. It is presently preferred that the spring 366 provide a force in the range of 2 to 5 lbs.

Figure 38:
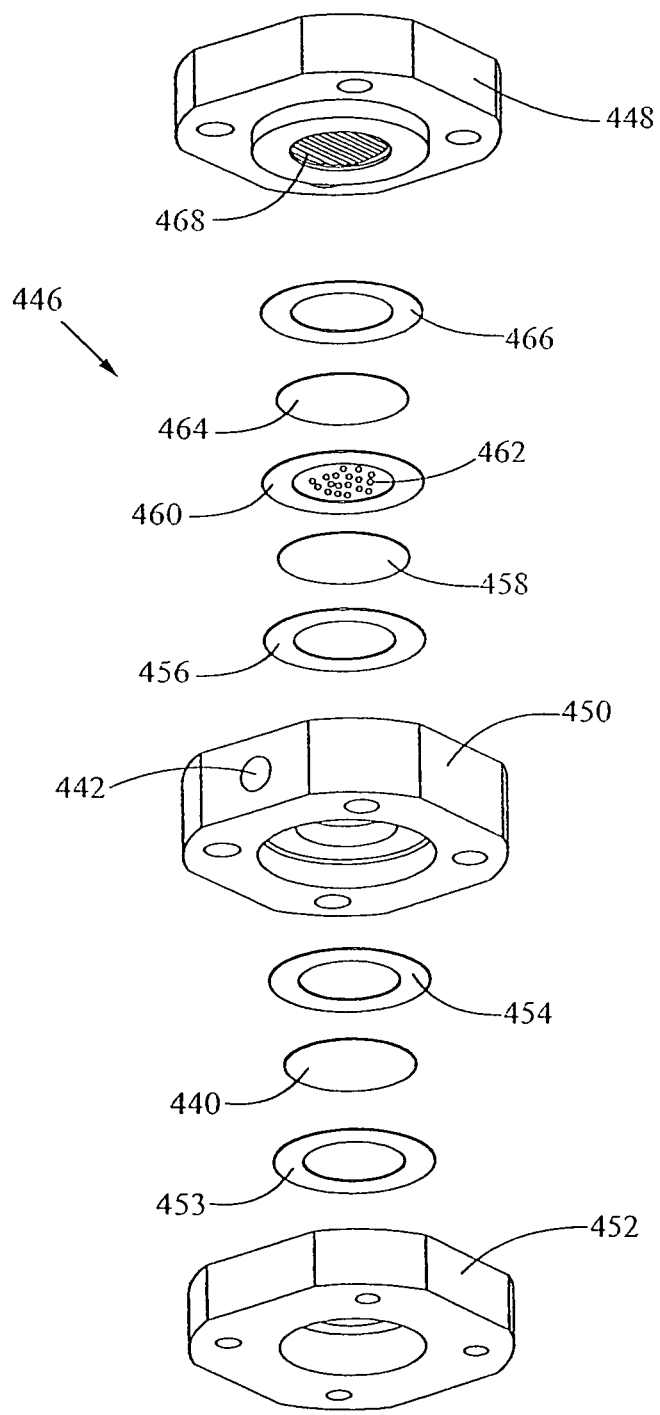
FIG. 38 is an exploded view of a container used in the apparatus of FIG. 36.
Figure 39:
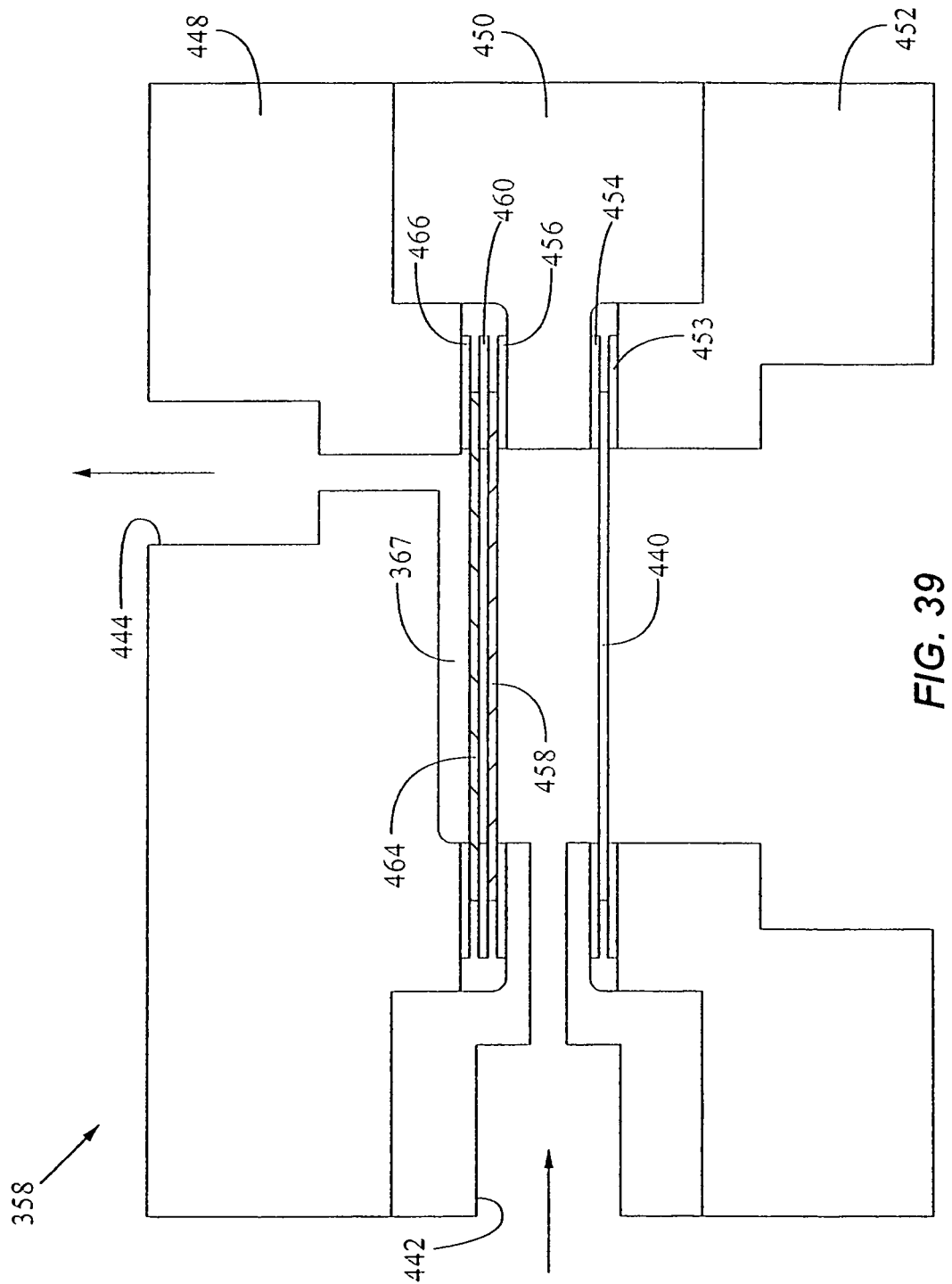
FIG. 39 is a cross sectional view of the container of FIG. 38.

FIG. 38 shows an exploded view of the container 358, and FIG. 39 shows an assembled view of the container 358. As shown in FIGS. 38-39, the container 358 has a body comprising a top piece 448, a middle piece 450, and a bottom piece 452. The middle piece 450 defines an inlet port 442 to the chamber 367, and the top piece 448 defines an outlet port 444 to the chamber. The ports 442, 444 are positioned to permit the continuous flow of a fluid sample through the chamber 367. The flexible wall 440 is held between the middle and bottom pieces 450, 452 using gaskets 453, 454. Alternatively, the flexible wall 440 may simply be heat sealed to the middle piece 450 so that the bottom piece 452 and gaskets 453, 454 may be eliminated.

The container 358 also includes a filter stack 446 in the chamber 367 for capturing sample components (e.g., target cells or viruses) as the sample flows through the chamber 367. The filter stack comprises (from bottom to top in FIGS. 38-39) a gasket 456, a first filter 458, a gasket 460, a second filter 464 having a smaller average pore size than the first filter 458, and a gasket 466. The filter stack is held between the top and middle pieces 448, 450 of the container 358. The filter stack also includes beads 462 disposed between the first and second filters 458 and 464. The gasket 460 spaces the first filter 458 from the second filter 464. The gasket 460 should be thick enough to permit the beads to move freely in the space between the filters 458, 464. A fluid sample flowing through the chamber 367 first flows through the filter 458 and then through the filter 466. After flowing through the filter stack, the sample flows along flow ribs 468 (FIG. 38) formed in the portion of the top piece 448 that defines the top of the chamber and through the outlet port 444 (FIG. 39).

The filter stack is effective for capturing cells or viruses as a fluid sample flows through the chamber 367 without clogging of the. The first filter 458 (having the largest pore size) filters out coarse material such as salt crystals, cellular debris, hair, tissue, etc. The second filter 464 (having a smaller pore size) captures target cells or viruses in the fluid sample. The average pore size of the first filter 458 is selected to be small enough to filter coarse material from the fluid sample (e.g., salt crystals, cellular debris, hair, tissue) yet large enough to allow the passage of the target cells or viruses. In general, the average pore size of the first filter 458 should be in the range of about 2 to 25 µm, with a presently preferred pore size of about 5 µm. The average pore size of the second filter 464 is selected to be slightly smaller than the average size of the target cells or viruses to be captured (typically in the range of 0.2 to 5 µm).

The beads 462 are useful for disrupting the captured cells or viruses to release the intracellular material (e.g., nucleic acid) therefrom. Movement of the beads 462 ruptures the cells or viruses captured on the filter 464. Suitable beads for rupturing cells or viruses include borosilicate glass, lime glass, silica, and polystyrene beads. The beads may be porous or non-porous and preferably have an average diameter in the range of 1 to 200 µm. In the presently preferred embodiment, the beads 462 are polystyrene beads having an average diameter of about 100 µm.

The beads 462 may have a binding affinity for target cells or viruses in the fluid sample to facilitate capture of the target cells or viruses. For example, antibodies or certain receptors may be coated onto the surface of the beads 462 to bind target cells in the sample. Moreover, the chamber 367 may contain two different types of beads for interacting with target cells or viruses. For example, the chamber may contain a first set of beads coated with antibodies or receptors for binding target cells or viruses and a second set of beads (intermixed with the first set) for rupturing the captured cells or viruses. The beads in the chamber may also have a binding affinity for the intracellular material (e.g., nucleic acid) released from the ruptured cells or viruses. Such beads may be useful for isolating target nucleic acid for subsequent elution and analysis. For example, the chamber 367 may contain silica beads to isolate DNA or cellulose beads with oligo dT to isolate messenger RNA for RT-PCR. The chamber 367 may also contain beads for removing unwanted material (e.g., proteins, peptides) or chemicals (e.g., salts, metal ions, or detergents) from the sample that might inhibit PCR.

To ensure that the air bubbles can escape from the chamber 367, it is desirable to use the container 358 in an orientation in which liquid flows up (relative to gravity) through the filters 458, 464 and the chamber 367. The upward flow through the chamber 367 aids the flow of air bubbles out of the chamber. Thus, the inlet port 442 for entry of fluids into the chamber 367 should generally be at a lower elevation than the outlet port 444. The volume capacity of the chamber 367 is usually in the range of 50 to 500 μl. The volume capacity of the chamber 367 is selected to provide for concentration of analyte separated from a fluid sample without the chamber being so small that the filters 458, 464 become clogged.

The pieces 448, 450, 452 forming the body of the container 358 are preferably molded polymeric parts (e.g., polypropylene, polycarbonate, acrylic, etc.). Although molding is preferred for mass production, it also possible to machine the top, middle, and bottom pieces 448, 450, 452. The pieces 448, 450, 452 may be held together by screws or fasteners. Alternatively, ultrasonic bonding, solvent bonding, or snap fit designs could be used to assemble the container 358. Another method for fabricating the container 358 is to mold the body as a single piece and heat seal the flexible wall 440 and the filters 458, 464 to the body.

Figure 40:
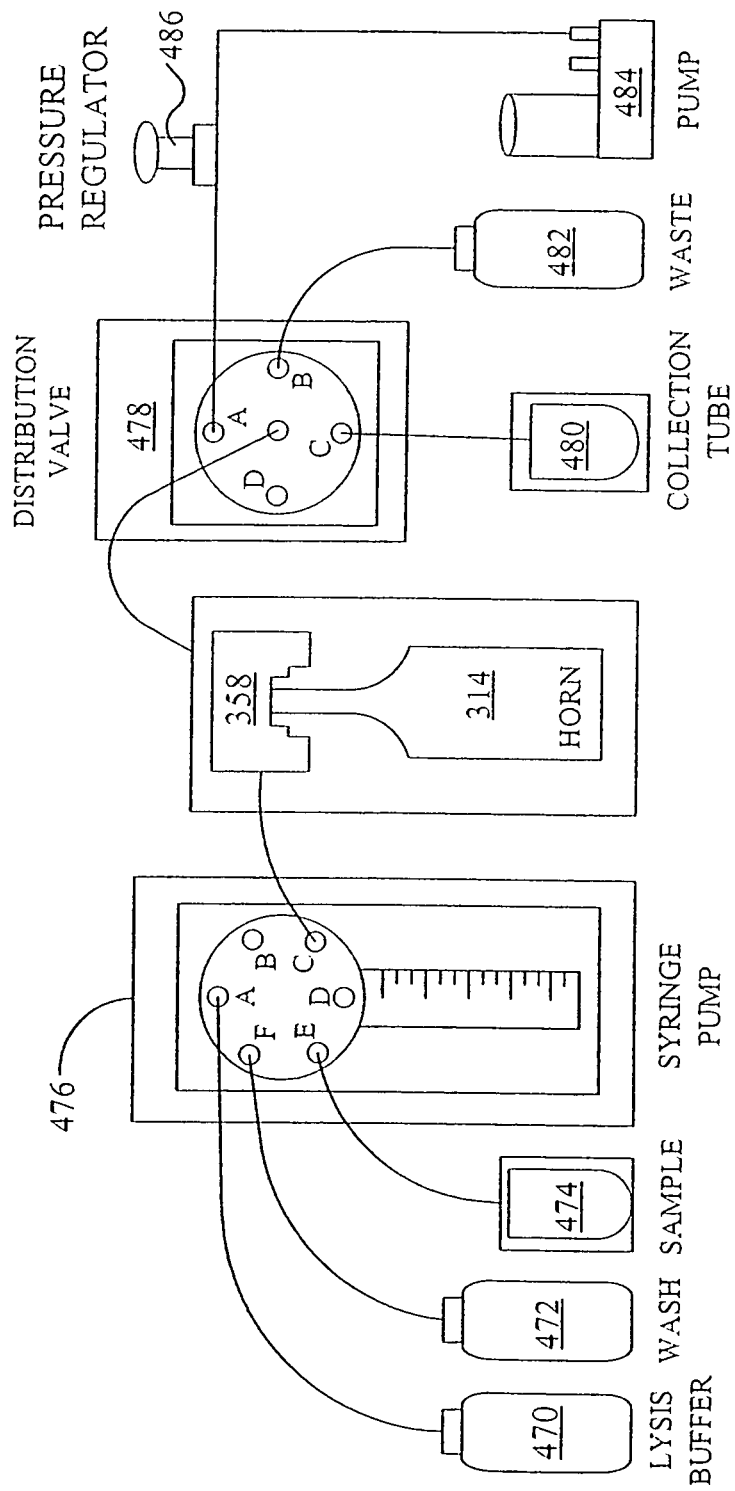
FIG. 40 is a schematic block diagram of a fluidic system incorporating the apparatus of FIG. 36.

FIG. 40 shows a fluidic system for use with the apparatus. The system includes a bottle 470 for holding lysis buffer, a bottle 472 containing wash solution, and a sample container 474 for holding a fluid sample. The bottles 470, 472 and sample container 474 are connected via tubing to the valve ports of a syringe pump 476. The inlet port of the container 358 is also connected to the syringe pump 476. The outlet port of the container 358 is connected to the common port of a distribution valve 478. The system also includes a collection tube 480 for receiving intracellular material removed from the sample, a waste container 482 for receiving waste, and a pressure source, such as a pump 484. The collection tube 480, waste container 482, and pump 484 are connected to respective peripheral ports of the distribution valve 478. A pressure regulator 486 regulates the pressure supplied by the pump 484.

A specific protocol will now be described with reference to FIGS. 39-40 to illustrate the operation of the container 358. It is to be understood that this is merely an example of one possible protocol and is not intended to limit the scope of the invention. The syringe pump 476 pumps a fluid sample from the sample container 474 through the container 358 and into the waste container 482. As the fluid sample is forced to flow through the filters in the chamber 367, coarse material is filtered by the filter 458 and target cells or viruses in the sample are captured by the filter 464. The chamber 367 may be sonicated as the sample is forced to flow through the chamber to help prevent clogging of the filters. Next, the syringe pump 476 pumps wash solution from the bottle 472 through the container 358 and into the waste container 482. The washing solution washes away PCR inhibitors and contaminants from the chamber 367.

In the next step, the syringe pump 476 pumps lysis buffer from the bottle 470 into the container 358 so that the chamber 367 is filled with liquid. The lysis buffer should be a medium through which dynamic pressure pulses or pressure waves can be transmitted. For example, the lysis buffer may comprise deionized water for holding the cells or viruses in suspension or solution. Alternatively, the lysis buffer may include one or more lysing agents to aid in the disruption of the cells or viruses. One of the advantages of the present invention, however, is that harsh lysing agents are not required for successful disruption of the cells or viruses. Next, the distribution valve of the syringe pump 476 is closed upstream of the container 358, and the distribution valve 478 is opened. The pump 484 then pressurized the chamber 367 through the outlet port 444, preferably to about 20 psi above the ambient pressure. The distribution valve 478 downstream of the container 358 is then closed. The static pressure in the chamber 367 is therefore increased to about 20 psi in preparation for the disruption of the cells or viruses trapped on the filter 464.

Referring again to FIG. 37, the pressurization of the chamber 367 is important because it ensures effective coupling between the transducer 314 and the flexible wall 440. To disrupt the cells or viruses in the chamber 367, the transducer 314 is activated (i.e., set into vibratory motion). The flexible wall 440 transfers the vibrational motion of the transducer 314 to the liquid in the chamber 367 by allowing slight deflections without creating high stresses in the wall. The transducer 314 is preferably an ultrasonic horn for sonicating the chamber 367. The chamber 367 is preferably sonicated for 10 to 40 seconds at a frequency in the range of 20 to 60 kHz. In the exemplary protocol, the chamber is sonicated for 15 seconds at a frequency of 40 kHz. The amplitude of the horn tip is preferably in the range of 20 to 25 μm (measured peak to peak).

As the tip of the transducer 314 vibrates, it repeatedly impacts the flexible wall 440. On its forward stroke (in the upward direction in FIG. 37), the tip of the transducer 314 pushes the wall 440 and creates a pressure pulse or pressure wave in the chamber 367. On its retreating stroke (downward in FIG. 37), the tip of the transducer 314 usually separates from the flexible wall 440 because the flexible wall 440 cannot move at the same frequency as the transducer. On its next forward stroke, the tip of the transducer 314 once again impacts the wall 440 in a head-on collision as the tip and wall speed towards each other. Because the transducer 314 and the wall 440 separate as the transducer 314 vibrates, the effective forward stroke of the transducer is less than its peak-to-peak amplitude. The effective forward stroke determines the level of sonication in the chamber 367. It is therefore important to increase the static pressure in the chamber 367 so that when the tip of the transducer 314 retreats, the flexible wall 440 is forced outwardly to meet the tip on its return stroke. The static pressure in the chamber 367 should be sufficient to ensure that the effective forward stroke of the transducer 314 generates the necessary pressure pulses or pressure waves in the chamber to effect cell disruption. It is presently preferred to increase the static pressure in the chamber 367 to at least 5 psi above the ambient pressure, and more preferably to a pressure in the range of 15 to 25 psi above the ambient pressure.

On each forward stroke, the transducer 314 imparts a velocity to the liquid in the chamber 367, thus creating a pressure pulse or pressure wave that quickly sweeps across the chamber. The beads 462 in the filter stack 446 (FIG. 38) are agitated by the pressure pulses in the chamber 367. The pressure pulses propel the beads into violent motion, and the beads mechanically rupture the cells or viruses to release the analyte (e.g., nucleic acid) therefrom. Referring again to FIG. 40, following disruption of the cells or viruses, the syringe pump 476 pumps the released intracellular material from the container 358 into the collection tube 480.

Figure 41:
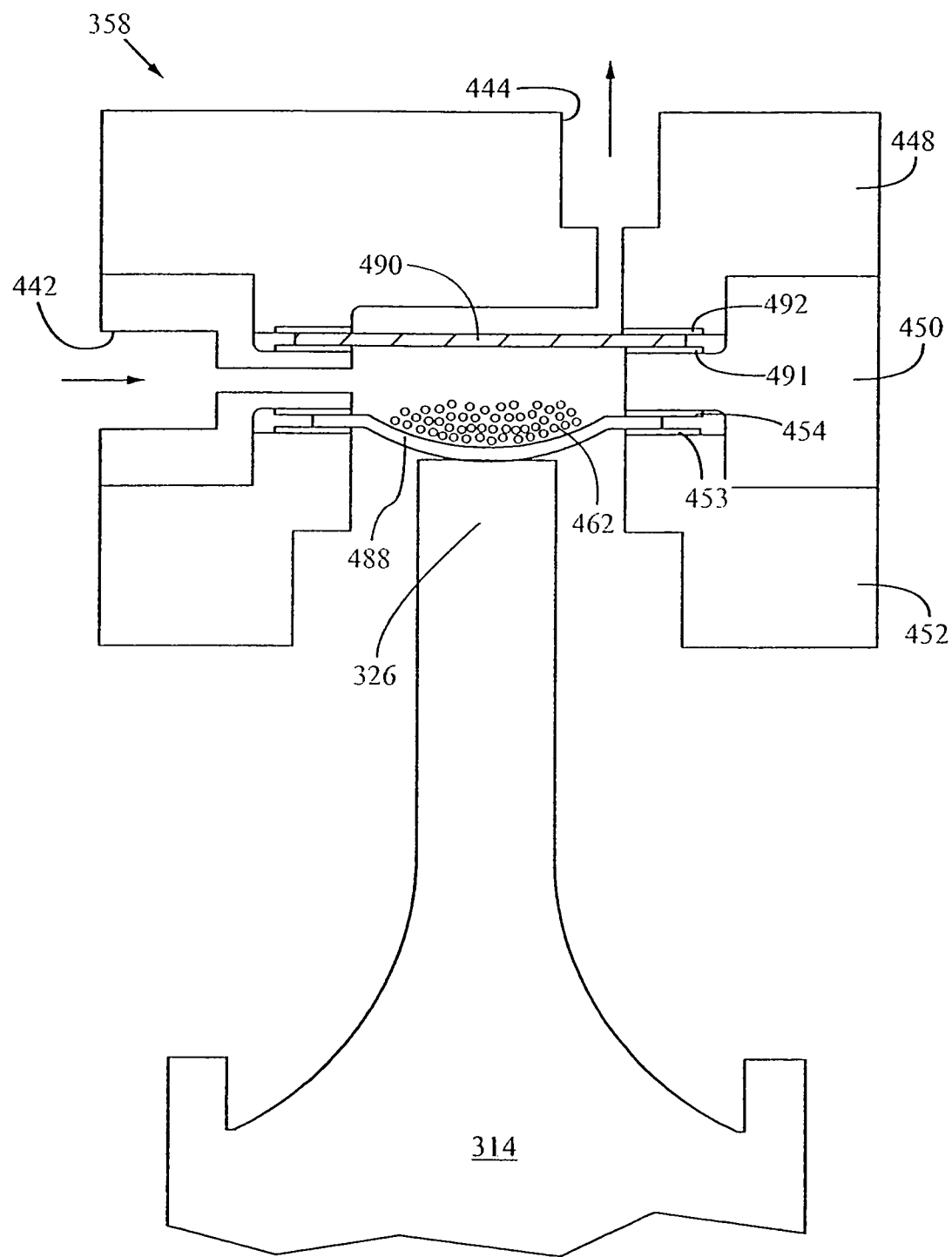
FIG. 41 is a cross sectional view of another container for use in the apparatus of FIG. 36. An ultrasonic horn is in contact with a wall of the container that curves outwardly towards the horn.

FIG. 41 shows another embodiment of the invention in which the container 358 has a solid wall 488 for contacting the transducer 314. The solid wall 488 differs from the flexible wall 440 previously described with reference to FIG. 37.

Whereas the flexible wall is typically a thin film that bends under its own weight and does not hold its shape unless held on its edges, the solid wall 488 holds it shape when unsupported. The advantage of using a solid wall to contact the transducer 314 is that there is no need to pressurize the chamber 367 to ensure effective coupling between the wall 488 and the transducer 314. The elastic restoring force of the solid wall 488 provides the necessary coupling between the wall and the transducer 314. However, the proper design of the solid wall 488 is necessary so that the wall is not damaged (e.g., melted) by the vibratory movements of the transducer 314.

In particular, the solid wall 488 should have a natural frequency that is higher than the vibrating frequency at which the transducer 314 is operated. Preferably, the ratio of the natural frequency of the wall 488 to the vibrating frequency is at least 2:1, and more preferably the ratio is at least 4:1. In addition, the wall 488 should not be so rigid that it cannot transfer the vibratory motion of the transducer to the liquid in the chamber 367. It is preferred that the wall 488 be capable of deflecting a distance in the range of 5 to 40 μm, and more preferably about 20 μm peak to peak when the transducer 314 applies a force in the range of 1 to 10 lbs. to the external surface of the wall 488. It is more preferable that the wall 488 be capable of deflecting a distance in the range of 5 to 40 μm, and more preferably about 20 μm peak to peak when the transducer 314 applies a force in the range of 2 to 5 lbs. To achieve these criteria, the wall 488 is dome-shaped and convex with respect to the transducer 314 (i.e., the wall 488 curves outwardly towards the transducer). The advantage to the dome-shaped design of the wall 488 is that the dome shape increases the natural frequency of the wall (compared to a flat wall) without causing the wall to be so stiff that it cannot transfer the vibratory movements of the transducer 314 to the chamber 367.

Figure 42:
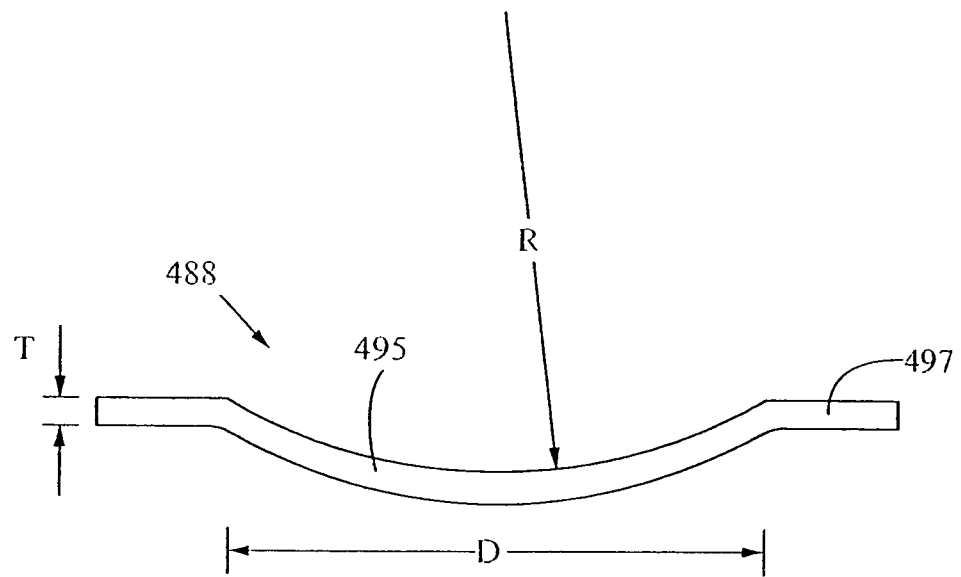
FIG. 42 is a cross-sectional view of the wall of FIG. 41.

FIG. 42 shows a cross sectional view of the wall 488. The dome-shaped portion 495 of the wall preferably has a radius of curvature R in the range of 6.3 to 12.7 mm when the diameter D of the dome-shaped portion is about 11.1 mm. More preferably, the dome-shaped portion 495 of the wall preferably has a radius of curvature R of about 9.5 mm when the diameter D of the dome-shaped portion is about 11.1 mm. The wall 488 also includes a flat outer rim 497 for clamping the wall 488 in the container 358. Alternatively, the wall 488 may be integrally molded with either of pieces 450, 452 (FIG. 41). The thickness T of the wall is preferably in the range of 0.25 to 1 mm. If it is less than 0.25 mm thick, the wall 488 may be too weak. If the wall has a thickness greater than 1 mm, the wall may be too stiff to deflect properly in response to the vibratory movements of the transducer. In the presently preferred embodiment, the wall 488 has a thickness T of about 0.5 mm. The wall 488 is preferably a molded plastic part. Suitable materials for the wall 488 include Delrin® (acetal resins or polymethylene oxide), polypropylene, or polycarbonate.

The interaction of the transducer 314 with the solid wall 488 will now be described with reference to FIG. 41. Prior to activating the transducer, target cells or viruses are captured on the filter 490 by forcing a fluid sample to flow though the chamber 367 (e.g., using the fluidic system previously described with reference to FIG. 40). In addition, the chamber 367 is filled with a liquid (e.g., lysis buffer) as previously described. Unlike the previously described embodiments, however, the chamber 367 does not require pressurization. Instead, it is preferred that ambient pressure is maintained in the chamber. The transducer 314 is placed in contact with the external surface of the wall 488, preferably using a support structure as previously described with reference to FIG. 37. In particular, a spring preferably pushes the transducer against the wall 488 with a force in the range of 1 to 10 lbs., and more preferably in the range of 2 to 5 lbs.

To disrupt the cells or viruses in the chamber 367, the transducer 314 is activated (i.e., induced into vibratory motion). As the tip of the transducer 314 vibrates, it deflects the wall 488. On its forward stroke (in the upward direction in FIG. 41), the tip of the transducer 314 pushes the wall 488 and creates a pressure pulse or pressure wave in the chamber 367. On its retreating stroke (downward in FIG. 41), the wall 488 remains in contact with the tip of the transducer 314 because the wall 488 has a natural frequency higher than the vibrating frequency of the transducer. In embodiments in which the transducer is an ultrasonic horn for sonicating the chamber 367, the chamber 367 is preferably sonicated for 10 to 40 seconds at a frequency in the range of 20 to 40 kHz. In the exemplary protocol, the chamber is sonicated for 15 seconds at a frequency of 40 kHz. The amplitude of the horn tip is preferably in the range of 20 to 25 μm (measured peak to peak), and the natural frequency of the wall 488 should be greater than 40 kHz, preferably at least 80 kHz, and more preferably at least 160 kHz.

One advantage to using the solid interface wall 488 is that strong pressure drops can be achieved in the chamber 367 as long as the static pressure in the chamber is low. For example, at atmospheric pressure, cavitation (the making and breaking of microscopic bubbles) can occur in the chamber 367. As these bubbles or cavities grow to resonant size, they collapse violently, producing very high local pressure changes. The pressure changes provide a mechanical shock to the cells or viruses, resulting in their disruption. The disruption of the cells or viruses may also be caused by sharp pressure rises resulting from the vibratory movement of the transducer 314. In addition, the disruption of the cells or viruses may be caused by the violent motion of the beads 462 in the chamber 367. The beads are agitated by the dynamic pressure pulses in the chamber and rupture the cells or viruses. In experimental testing, the applicants have found that it is usually necessary to use beads to disrupt certain types of cells (particularly spores) having highly resistant cell walls. Other types of cells, such as blood cells, are easier to disrupt and may often be disrupted without the use of the beads 462.

Although the use of an ultrasonic transducer has been described as a preferred embodiment, it is to be understood that different types of transducers may be employed in the practice of the present invention. The transducer should be capable of creating pressure pulses or pressure waves in the chamber 367. In addition, the transducer should be capable of providing high velocity impacts to the liquid in the chamber. Suitable transducers include ultrasonic, piezoelectric, magnetostrictive, or electrostatic transducer. The transducer may also be an electromagnetic device having a wound coil, such as a voice coil motor or a solenoid device. The vibrating frequency of the transducer may be ultrasonic (i.e., above 20 kHz) or below ultrasonic (e.g., in the range of 60 to 20,000 Hz). The advantage to using higher frequencies is that cell disruption is very rapid and can often be completed in 10 to 20 seconds. The disadvantage is that ultrasonic transducers are often more expensive than a simple mechanical vibrator, e.g., a speaker or electromagnetic coil device. In one alternative embodiment, for example, the solid wall 488 is used in combination with a speaker or electromagnetic coil device that vibrates at an operating frequency in the range of 5 to 10 kHz.

Figure 43A:
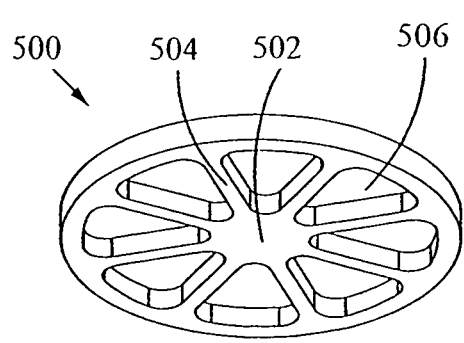
FIGS. 43A-43B are isometric views of opposite sides of another wall suitable for use in a container for holding cells or viruses to be disrupted.
Figure 43B:
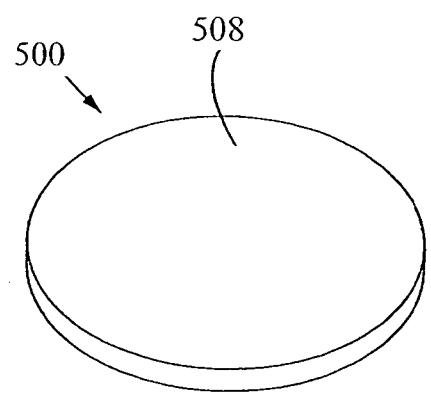
Figure 44:
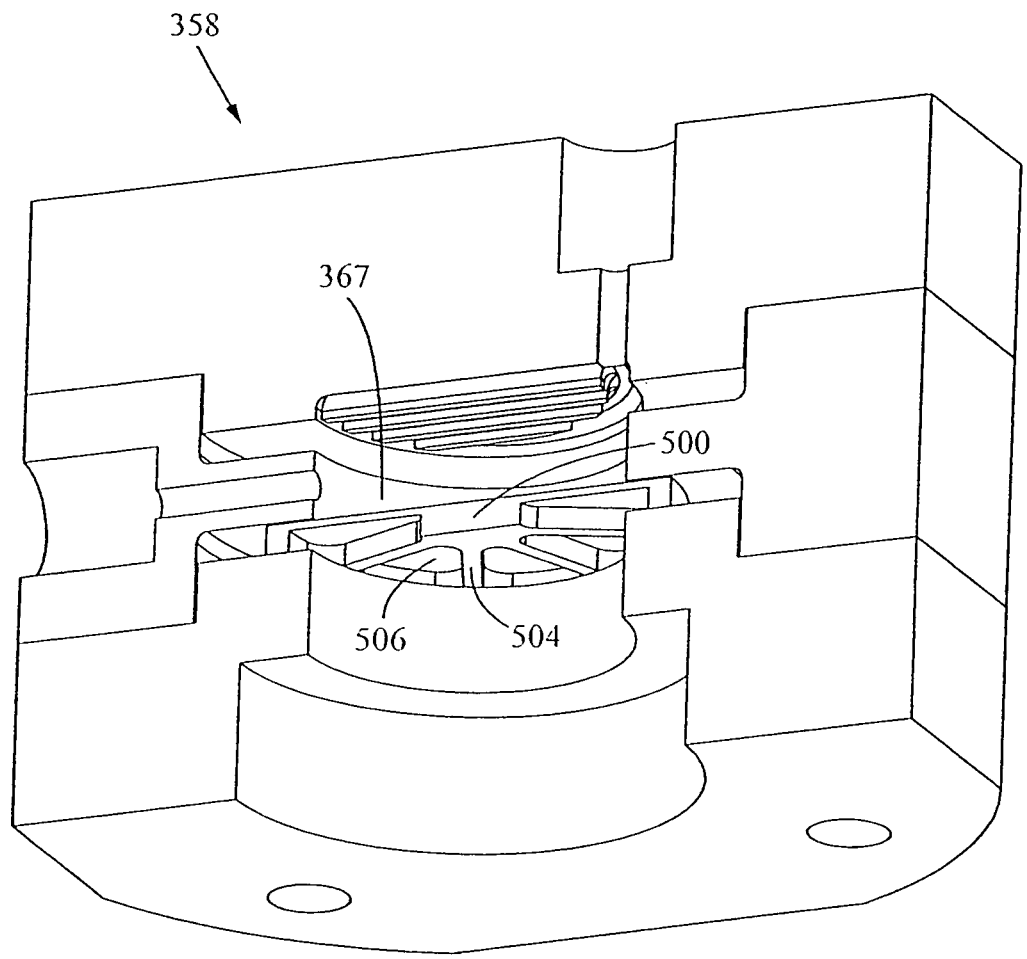
FIG. 44 is a partially cut-away, isometric view of a container incorporating the wall of FIGS. 43A-43B.

FIGS. 43A-43B illustrate another solid wall 500 for contacting a transducer according to the present invention. As shown in FIG. 43A, one side of the wall 500 has a central portion 502 and a plurality of stiffening ribs 504 extending radially from the central portion 502. The wall also has recesses 506 formed between the ribs 504. As shown in FIG. 43B, the other side of the wall 500 has a flat surface 508. FIG. 44 shows a partially-cut away isometric view of the container 358 with the wall 500. The wall 500 is preferably positioned so that the side of the wall having the flat surface is internal to the chamber 367 and such that the side of the wall having the ribs 504 is external to the chamber. The ribs 504 are advantageous because they increase the natural frequency of the wall without causing the wall to be so stiff that it cannot transfer the vibratory movements of the transducer to the chamber 367.

Figure 45:
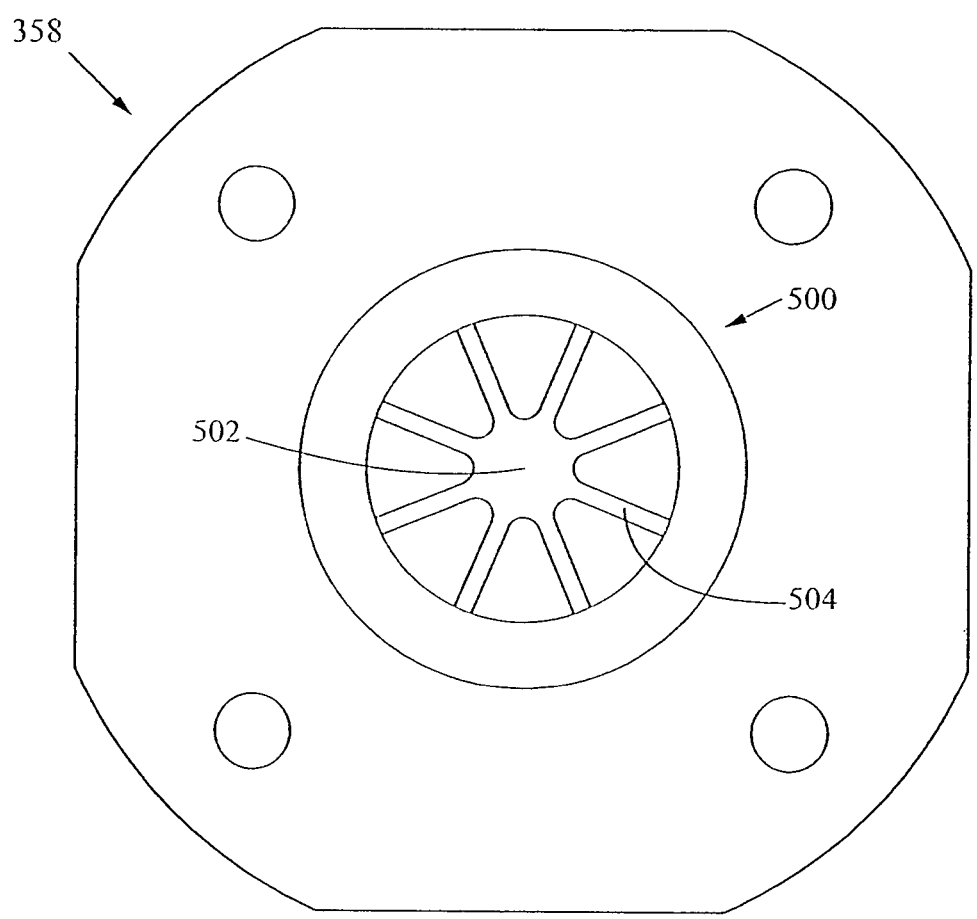
FIG. 45 is a bottom plan view of the container of FIG. 44.

FIG. 45 shows a bottom plan view of the container 358 having the wall 500. The central portion 502 provides the external surface of the wall 500 for contacting a transducer. The interaction of the wall 500 with the transducer is analogous to the interaction of the wall 488 with the transducer previously described with reference to FIG. 41. In particular, the wall 500 remains in contact with the tip of the transducer because the wall 500 has a natural frequency higher than the vibrating frequency of the transducer. Consequently, pressurization is not required, and cavitation may be achieved. The solid walls 488, 500 described with reference to FIGS. 41-45 may be used in the container 358 or the walls 488, 500 may be used in a fully integrated cartridge, such as the cartridge shown in FIG. 1.

Figure 46:
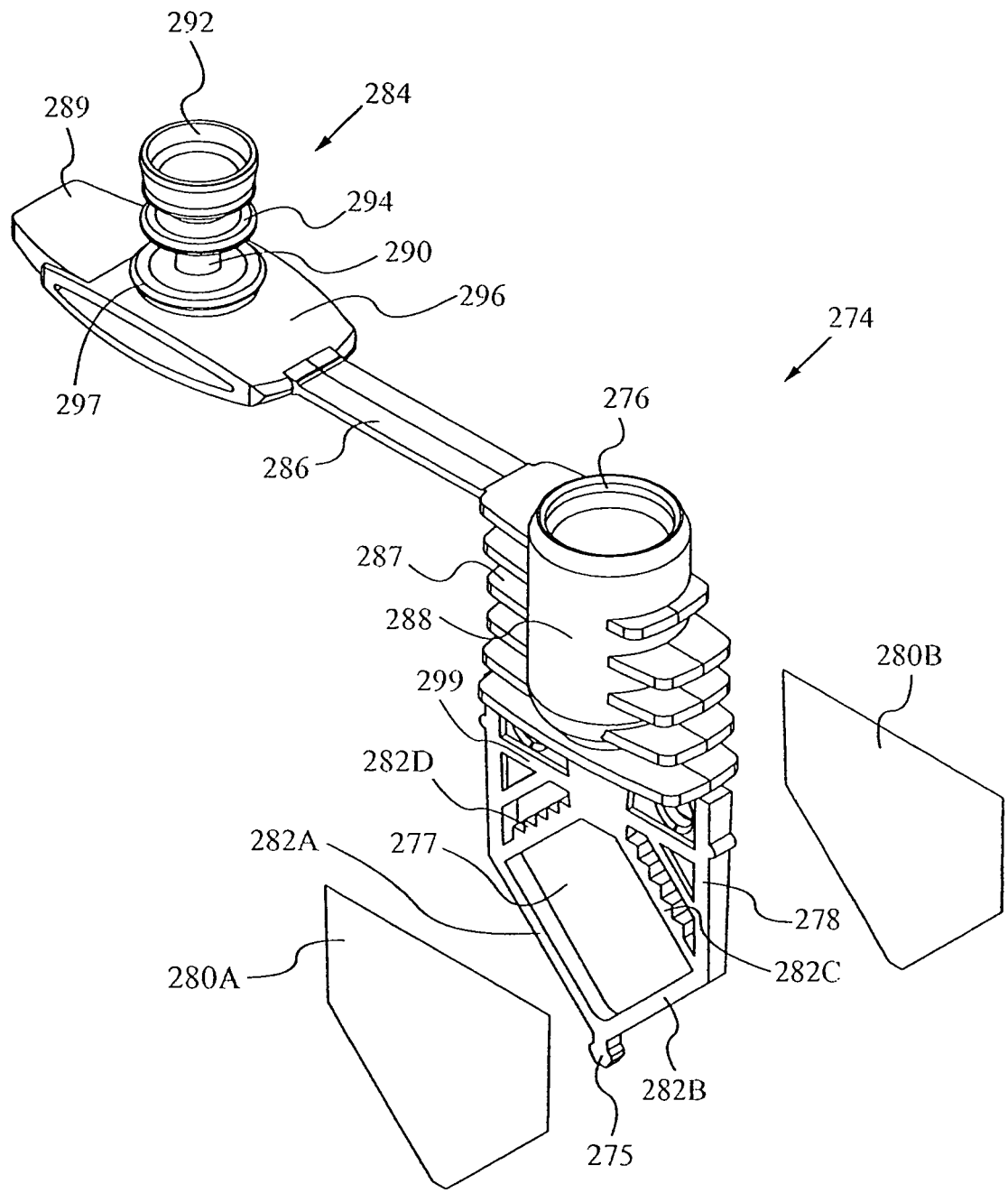
FIG. 46 is a partially exploded, isometric view of a container for holding cells or viruses to be disrupted according to another embodiment of the invention.
Figure 47:
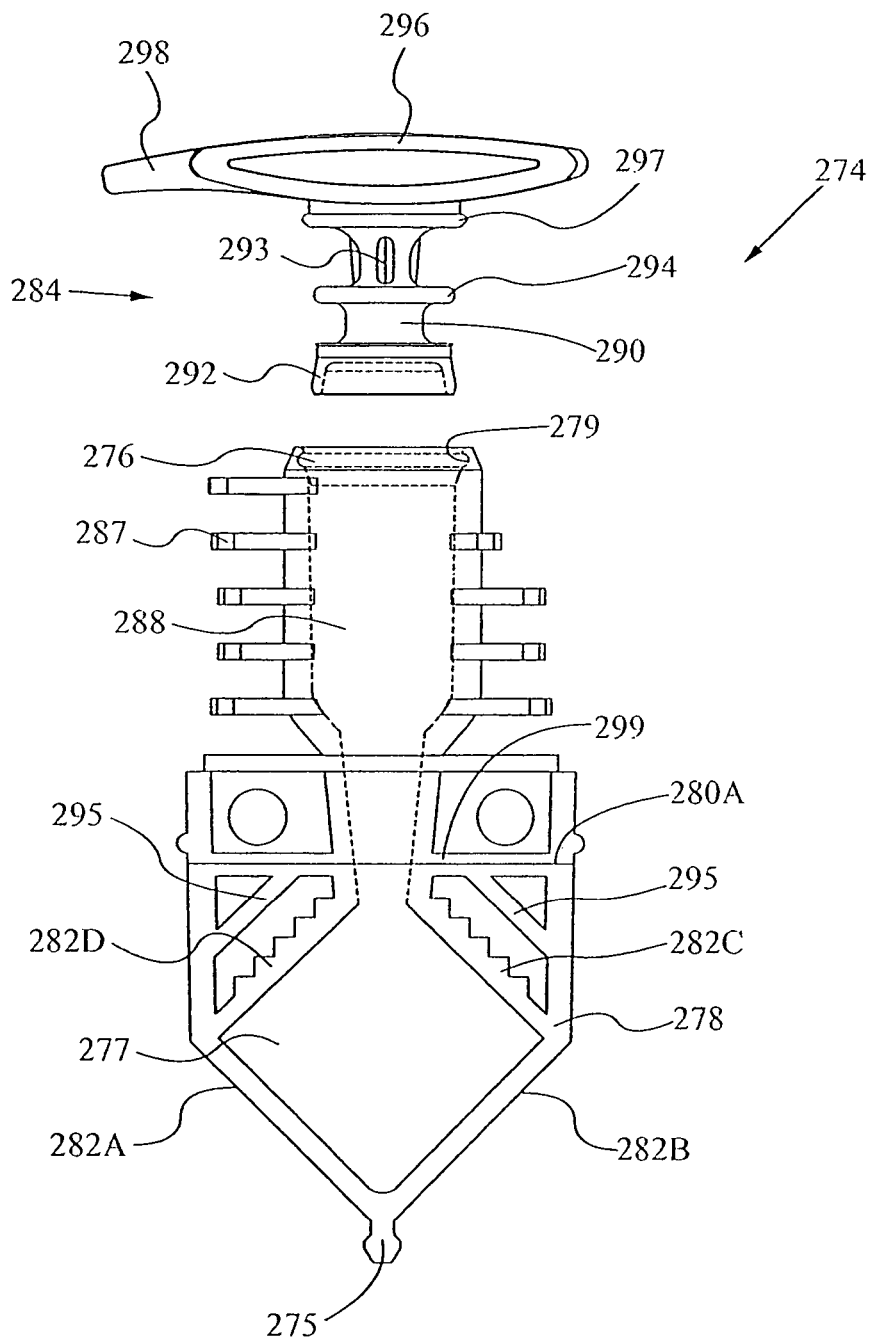
FIG. 47 is a front view of the container of FIG. 46.

FIG. 46 shows a partially exploded view of a container 274 for holding cells or viruses to be disrupted according to another embodiment of the invention. FIG. 47 shows a front view of the container 274. As shown in FIGS. 46-47, the container 274 has a chamber 277 for holding a liquid containing cells or viruses to be disrupted. The container 274 has a rigid frame 278 that defines the side walls 282A, 282B, 282C, 282D of the chamber 277. The rigid frame 278 also defines a port 276 and a channel 288 that connects the port 276 to the chamber 277. The container also includes thin, flexible sheets attached to opposite sides of the rigid frame 278 to form two spaced-apart, opposing major walls 280A, 280B of the chamber. The flexible major walls 280A, 280B are shown in FIG. 46 exploded from the rigid frame 278 for illustrative clarity. When the container 274 is assembled, the major walls 280A, 280B are sealed to opposite sides of the frame 278, as is described in detail below. The chamber 277 is thus defined by the spaced apart, opposing major walls 280A, 202B and by the rigid side walls side walls 282A, 282B, 282C, 282D that connect the major walls to each other.

The container 274 also includes a plunger 284 that is inserted into the channel 288 after adding the cells or viruses to the chamber 277. The plunger 284 compresses gas in the container 274 thereby increasing pressure in the chamber 277. The gas compressed by the plunger 284 is typically air filling the channel 288. The pressurization of the chamber 277 forces the flexible wall 280A to conform to the surface of the transducer (not shown in FIGS. 46-47), as is discussed in greater detail below. The plunger 284 also closes the port 276 and seals the chamber 277 from the environment external to the container.

In general, the plunger may comprise any device capable of establishing a seal with the walls of the channel 288 and of compressing gas in the container. Such devices include, but are not limited to, pistons, plugs, or stoppers. The plunger 284 of the preferred embodiment includes a stem 290 and a piston 292 on the stem. When the plunger 284 is inserted into the channel 288, the piston 292 establishes a seal with the inner walls of the channel and compresses air in the channel. The piston 292 is preferably a cup integrally formed (e.g., molded) with the stem 290. Alternatively, the piston 292 may be a separate elastomeric piece attached to the stem.

The plunger 284 also preferably includes an alignment ring 294 encircling the stem for maintaining the plunger 284 in coaxial alignment with the channel 288 as the plunger is inserted into the channel. The alignment ring 294 is preferably integrally formed (e.g., molded) with the stem 290. The stem 290 may optionally includes support ribs 293 for stiffening and strengthening the stem. The plunger 284 also includes a plunger cap 296 attached to the stem 290. As shown in FIG. 47, the cap 296 includes a snap ring 297 and the container includes an annular recess 279 encircling the port 276 for receiving the snap ring 297. The cap 296 may optionally include a lever portion 298 which is lifted to remove the plunger 284 from the channel 288. The container 274 may also include finger grips 287 for manual handling of the container.

Figure 51:
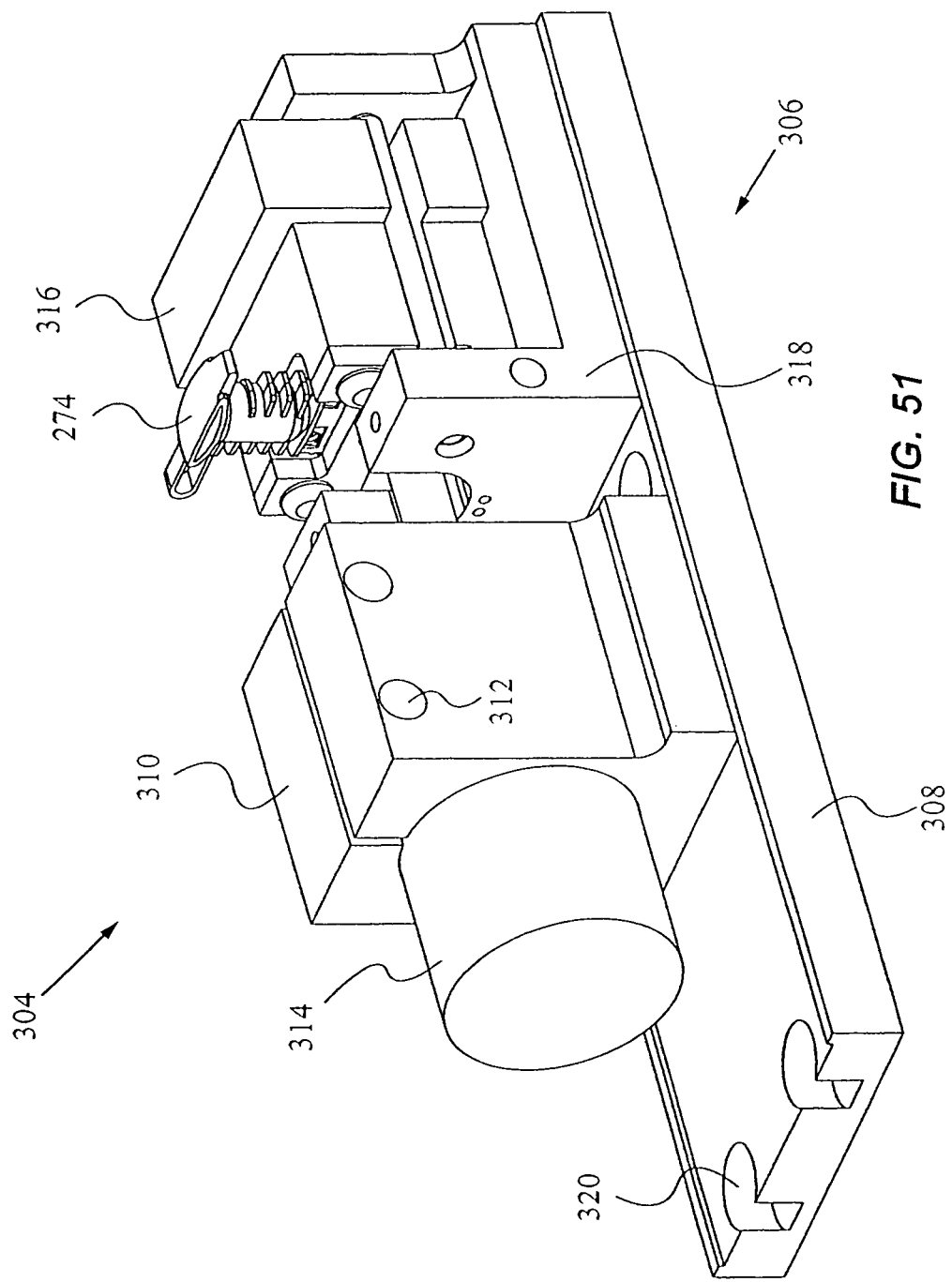
FIG. 51 is an isometric view of the container of FIG. 46 inserted into an apparatus for disrupting cells or viruses.

FIG. 51 shows an isometric view of an apparatus 304 for disrupting cells or viruses. The apparatus 304 includes a transducer 314, preferably an ultrasonic horn, for generating pressure pulses the chamber of the container 274. The apparatus 304 also includes a support structure 306 for holding the transducer 314 and the container 274 against each other. The support structure 306 includes a base 308 and a first holder 310 attached to the base for holding the outer housing of the transducer 314. The holder 310 includes a bore for receiving the transducer 314 and screws or bolts 312 that are tightened to clamp the outer housing of the horn firmly in the holder. The base 308 may optionally include bolt holes 320 for bolting the support structure 306 to a surface, e.g., a counter or bench top.

Figure 52:
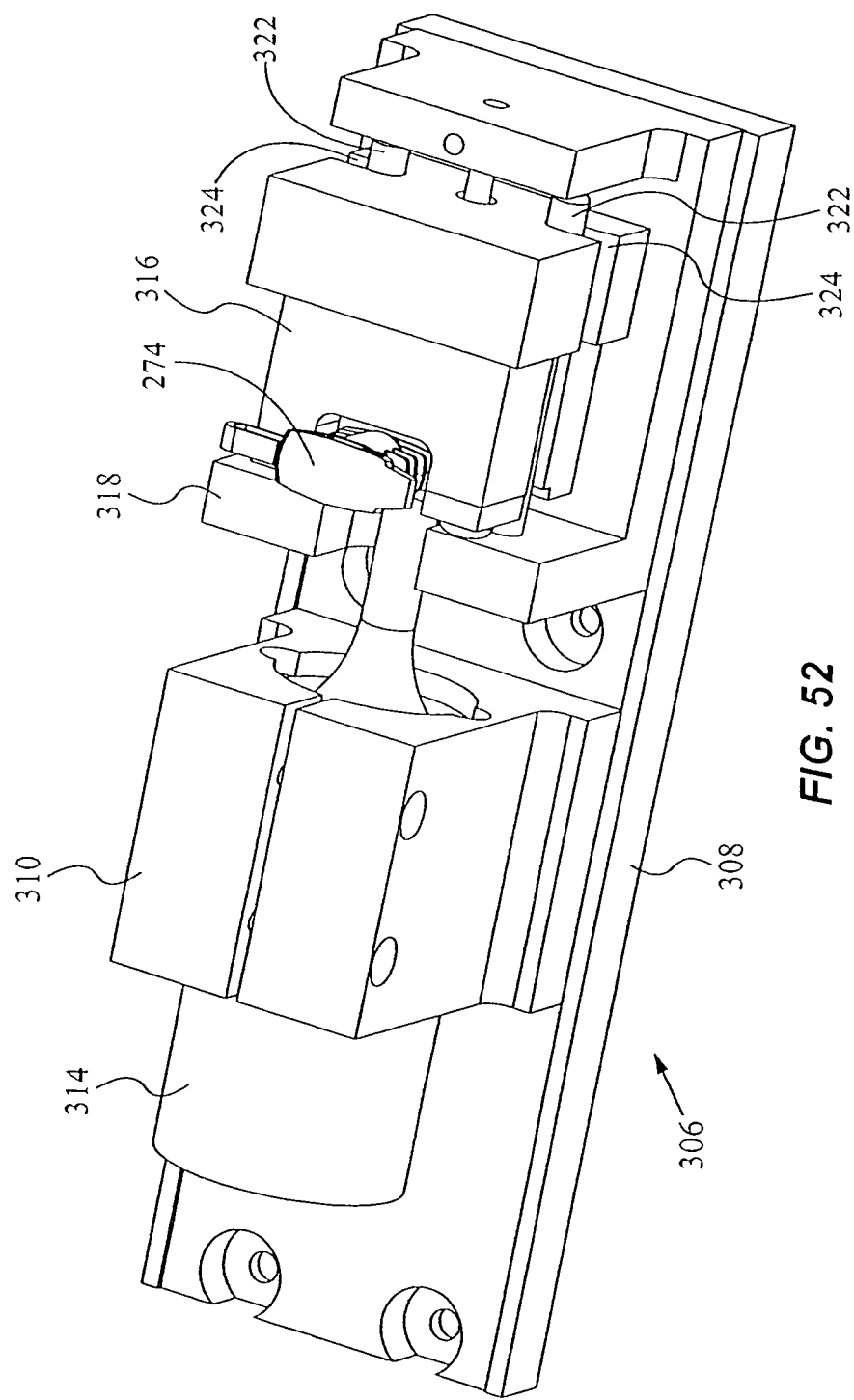
FIG. 52 is a different isometric view of the container of FIG. 46 inserted into the apparatus of FIG. 51.
Figure 53:
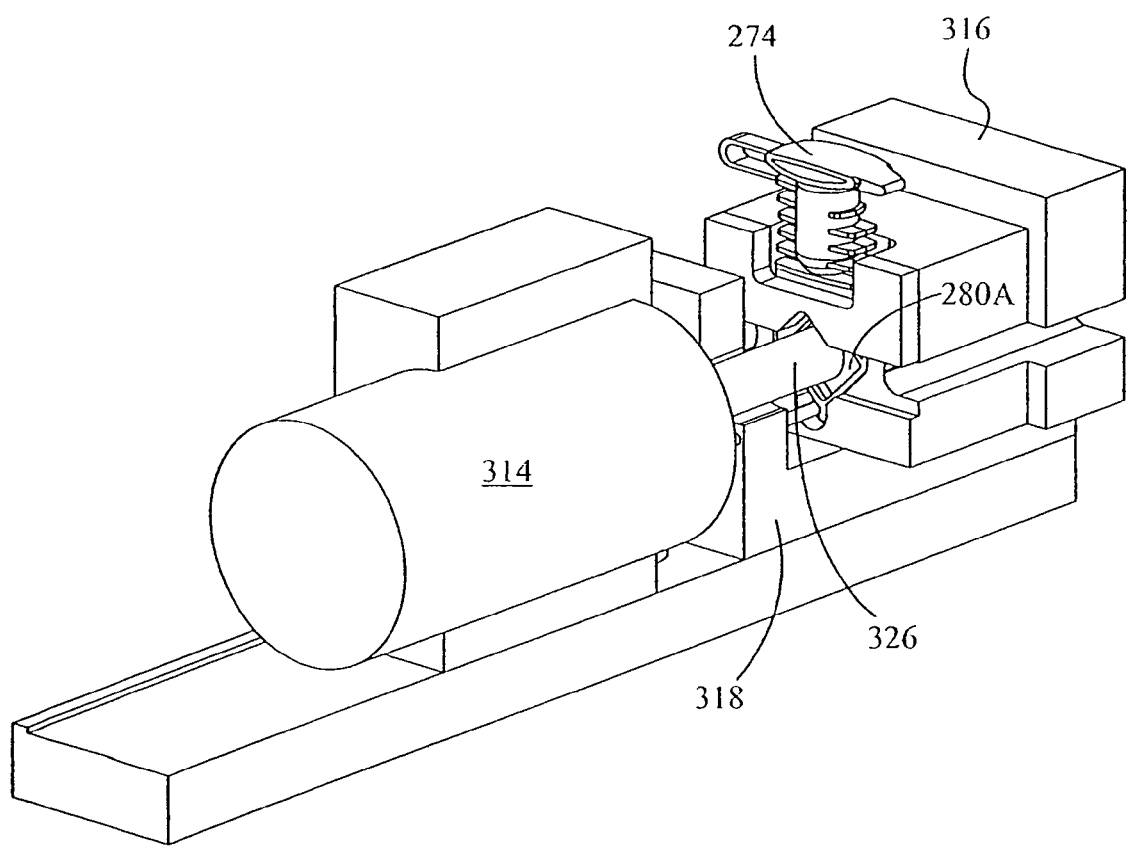
FIG. 53 is a partially cut-away, isometric view of the apparatus of FIG. 51.

As shown in FIG. 52, the support structure 306 also includes a holder 316 for holding the container 274. The holder 316 is slidably mounted to the base 308 by means of a guide 318. The guide 318 may be fixedly attached to the base 308 or integrally formed with the base. The guide 318 has two guide pins 322, and the holder 316 has two guide slots 324 for receiving the guide pins 322. The holder 316 may thus slide on the guide pins 322. As shown in the partially cut-away view of FIG. 53, the holder 316 is designed to hold the container 274 such that the external surface of the flexible wall 280A is exposed and accessible to the tip 326 of the transducer 314. The guide 318 is appropriately aligned with the transducer 314 to slide the holder 316 into a position in which the external surface of the flexible wall 280A contacts the tip 326.

Figure 54:
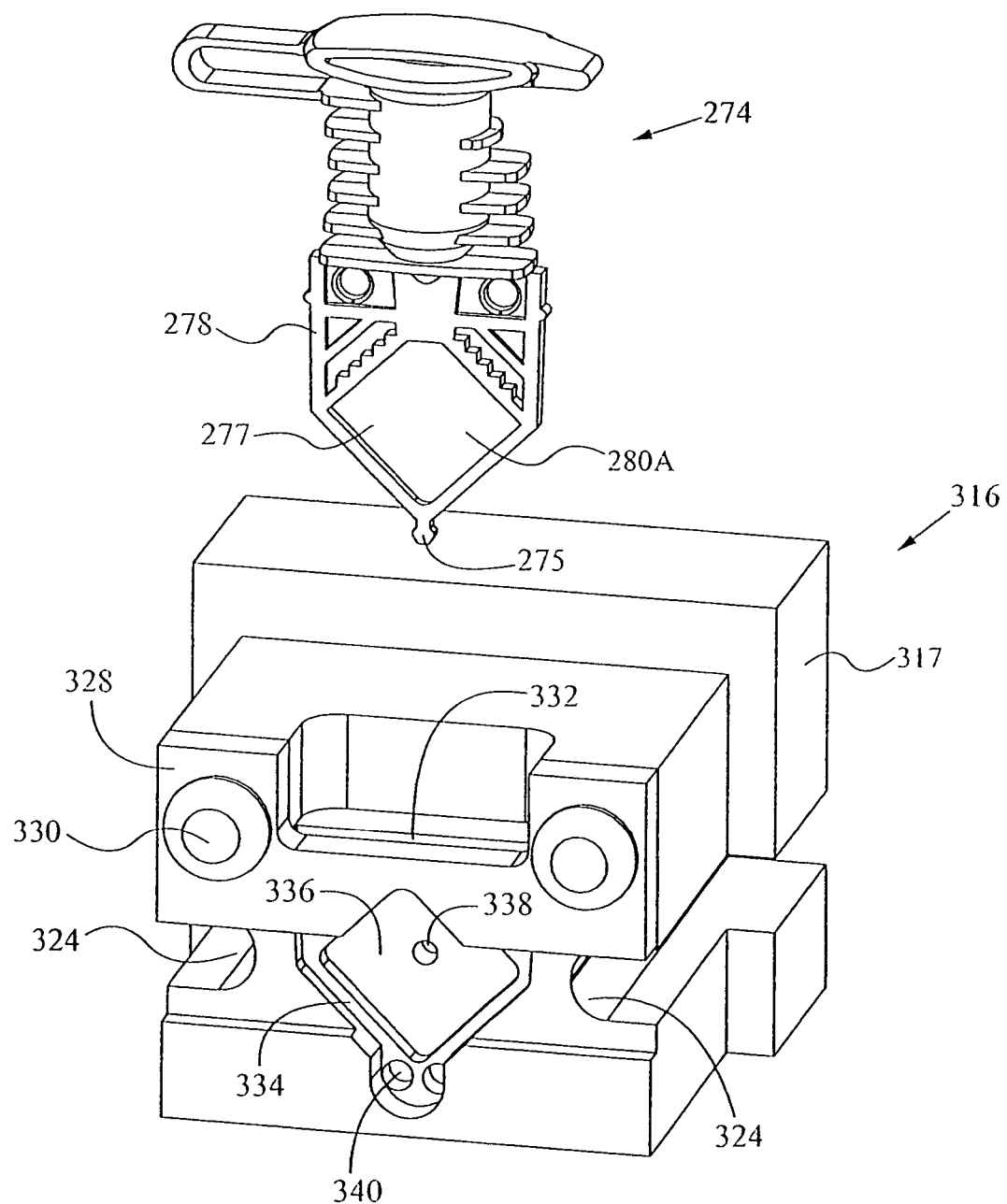
FIG. 54 is an isometric view of a holder for holding the container of FIG. 46.

FIG. 54 shows an isometric view of the holder 316. The holder 316 has a body 317 in which are formed the guide slots 324 for receiving the guide pins. The body also has a recess 334 for receiving the container 274. The shape of the recess 334 matches the shape of the lower portion of the frame 278 so that the frame fits securely in the recess 334. The holder 316 also includes a retaining member 328 attached to the body 317 by screws or bolts 330. The retaining member 328 and body 317 define a slot 332 through which the frame 278 is inserted when the frame is placed in the recess 334. The retaining member 328 holds the frame 278 in the recess. The body 317 also has an opening 336 adjacent the recess 334. The shape of the opening 336 corresponds to the shape of the chamber 277.

Figure 56:
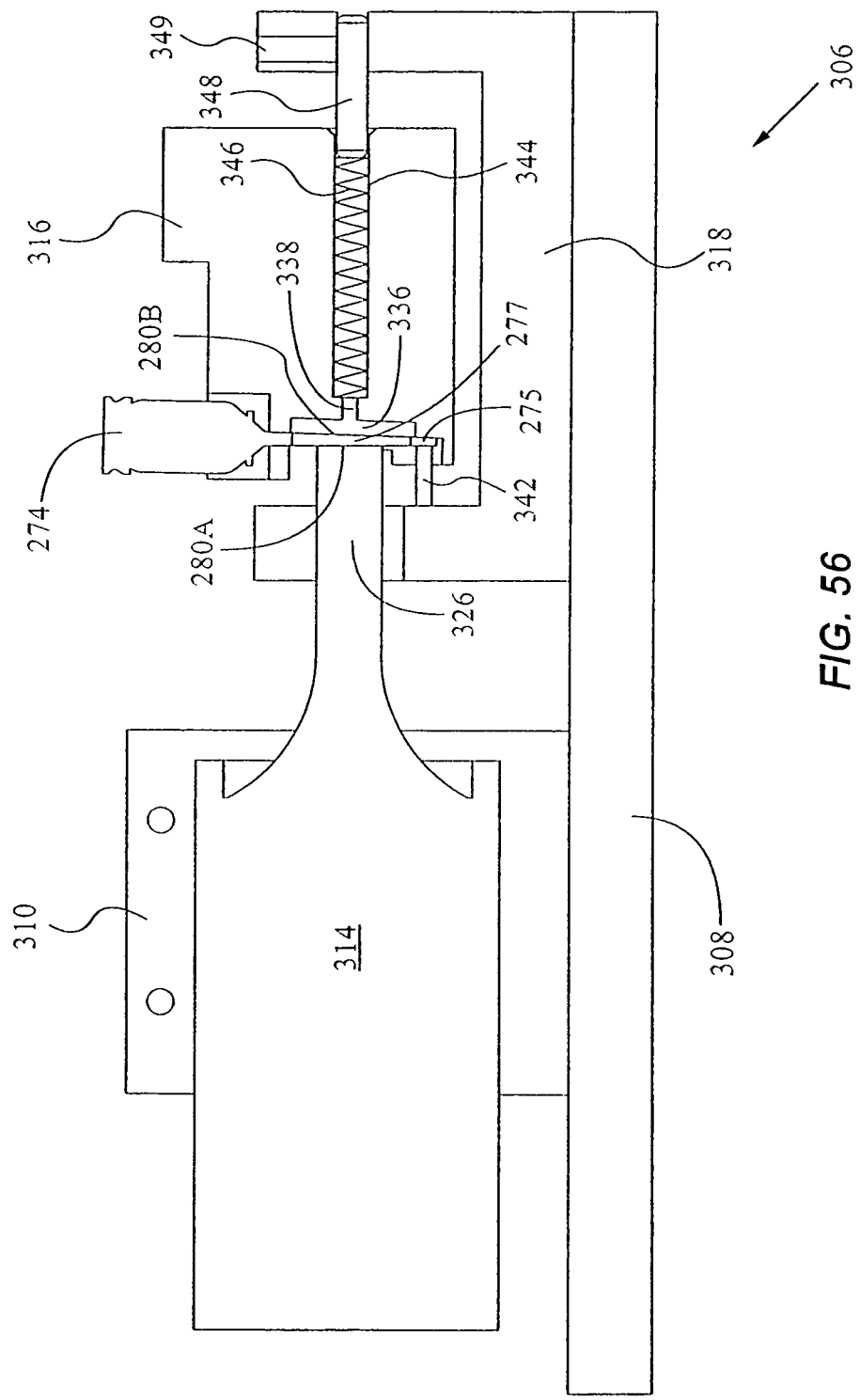
FIG. 56 is a schematic side view of the container of FIG. 46 inserted into the apparatus of FIG. 51 for disruption of the cells or viruses contained in the container.

As shown in the cross sectional view of FIG. 56, when the container 274 is inserted into the holder 316, the opening 336 is positioned next to the flexible wall 280B. The opening 336 is thus positioned to permit the flexible wall 280B to expand outwardly into the opening. The holder 316 holds only the frame of the container 274 so that the flexible walls 280A, 280B are unrestrained by the holder. The flexible wall 280A is therefore free to move inwardly and outwardly with the horn tip 326 as vibrational motion is transmitted from the tip 326 to the wall 280A. The flexible wall 280B is also free to move inwardly or outwardly as pressure pulses sweep through the chamber 277. This permits the liquid within the chamber 277 to move more freely as it receives the dynamic pressure pulses and thus enhances the cell disruption in the chamber 277. Venting of the opening 336 is provided by first and second bores 338, 344 formed in the body of the holder 316. One end of the narrower bore 338 is connected to the opening 336 and the other end is connected to the larger bore 344. The bore 344 extends through the body of the holder 316 to permit the escape of gas (e.g., air) from the opening 336. The venting prevents pressure from building in the opening 336 when the flexible wall 280B expands into the opening. Such pressure would restrict the motion of the wall 280B.

Figure 55:
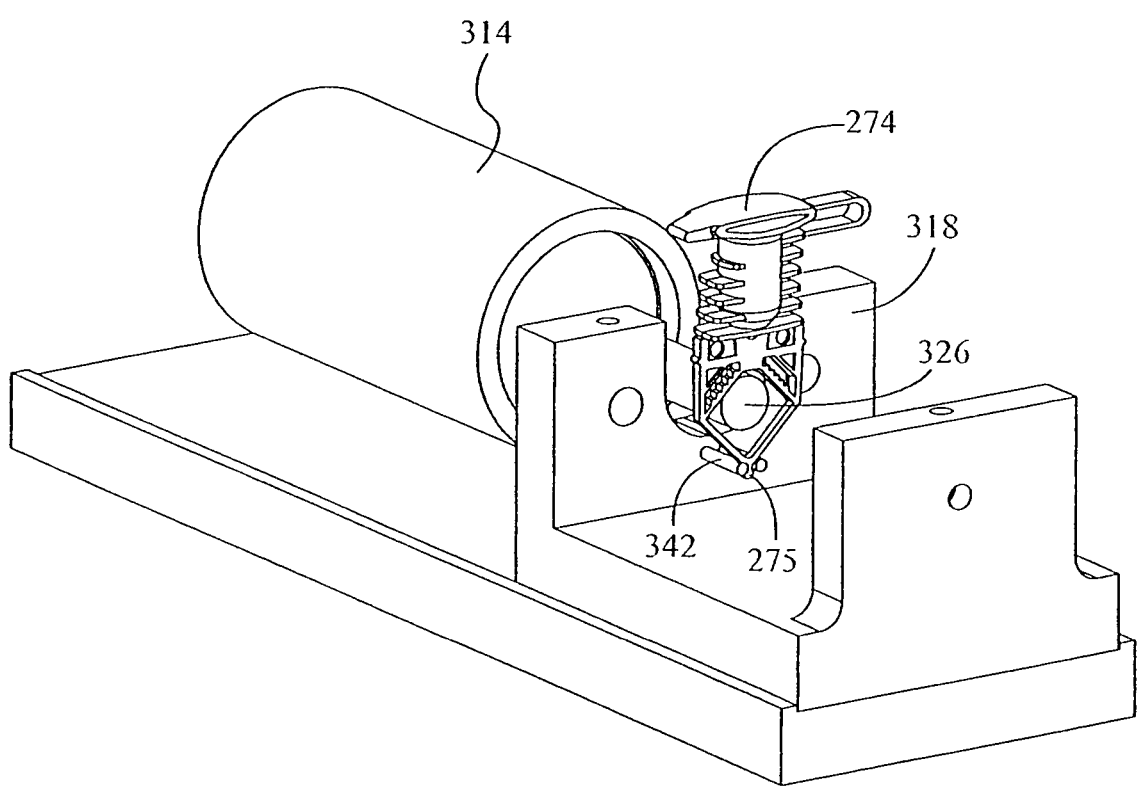
FIG. 55 is another isometric view of the apparatus of FIG. 51 in which several parts of the apparatus have been removed to show an ultrasonic horn contacting the container of FIG. 46.

Referring again to FIG. 54, the container 274 has a bulb-shaped tab 275 extending from the bottom of the frame 278. The holder 316 has holes 340 formed in the body 317 adjacent the recess 334. When the frame 278 is inserted into the recess 334, the tab 275 is positioned between the holes 340. The holes 340 are for receiving retaining pins. As shown in FIG. 55, the retaining pins 342 extend from the guide 318 (from which the guide pins have been removed for clarity in FIG. 55) and are positioned on opposite sides of the bulb-shaped tab 275 when the container 274 is moved into contact with the horn tip 326. The spacing of the pins 342 is less than the width of the bulb so that the pins 342 hold down the tab 275, and thus the container 274, as ultrasonic energy is transmitted into the container from the transducer 314. This ensures that the container 274 does not rise out of position due to the motion of the horn tip 326. Alternatively, a collar or other suitable retention mechanism may be used to hold the container 274 in position.

Referring to FIG. 56, the support structure 306 also includes an elastic body, such as a spring 366, for applying a force to the holder 316 to press the wall 280A of the chamber 277 against the horn tip 326. When the wall 280A is in contact with the horn tip 326, the force provided by the spring is constant, providing for consistent coupling and transfer of power between the transducer 314 and the container 274. The spring 366 is positioned in the bore 344. The holder 316 has an inner surface surrounding the junction of the larger bore 344 and the narrower bore 338. One end of the spring 366 contacts the inner surface, and the other end of the spring contacts a rod 348 that extends from the guide 318. The spring 366 is thus compressed between the surface of the holder 316 and the rod 348 so that it pushes the holder 316, and thus the flexible wall 280A of the container 274, against the tip 326.

The magnitude of the force provided by the spring 366 may be adjusted by changing the preload on the spring. The support structure 306 includes a rod 348 that contacts one end of the spring. The guide 318 includes a first bore for receiving the rod 348 and a second bore for receiving a set screw 349 that holds the rod 348 in a fixed position. To adjust the preload on the spring 366, the screw 349 is loosened, the rod 348 is moved to a new position, and the screw 349 is retightened to hold the rod 348 in the new position. The rod 348 and set screw 349 thus provide a simple mechanism for adjusting the preload on the spring 366. Once the preload on the spring 366 is adjusted to provide a suitable coupling force between the wall 280A and the horn tip 326, it is desirable to keep the preload constant from one use of the apparatus to the next so that valid comparisons can be made between different samples disrupted by the apparatus.

The flexible wall 280A facilitates the transfer of vibrating motion from the transducer 314 to the chamber 277. The wall 280A is sufficiently flexible to conform to the surface of the tip 326 of the transducer, ensuring good coupling between the tip 326 and the wall 280A. The surface of the tip 326 that contacts the wall 280A is preferably planar (e.g., flat) to ensure power coupling over the entire area of the surface. Alternatively, the tip 326 may have a slightly curved (e.g., spherical) surface for contacting the wall 280A. The opposite wall 280B is preferably sufficiently flexible to move inwardly and outwardly as dynamic pressure pulses are generated in the chamber 277. This permits the liquid within the chamber 277 greater freedom of movement as it receives the pressure pulses and thus enhances the action in the chamber 277.

Referring again to FIG. 46, the walls 280A, 280B are preferably flexible sheets or films of polymeric material such as polypropylene, polyethylene, polyester, or other polymers. The films may either be layered, e.g., laminates, or the films may be homogeneous. Layered films are preferred because they generally have better strength and structural integrity than homogeneous films. Alternatively, the walls 280A, 280B may comprise any other material that may be formed into a thin, flexible sheet. For good flexibility and energy transfer, the thickness of each wall is preferably in the range of 0.01 to 0.2 mm, and more preferably in the range of 0.025 to 0.1 mm. As previously described, the plunger 284 is inserted into the channel 288 after adding the cells or viruses to the chamber 277. The plunger 284 compresses air in the channel 288, thereby increasing pressure in the chamber 277. The pressurization of the chamber 277 ensures effective coupling between the wall 280A and the tip of the transducer 314.

It is presently preferred to pressurize the chamber 277 to a pressure in the range of 2 to 50 psi above ambient pressure. This range is presently preferred because 2 psi is generally enough pressure to ensure effective coupling between the flexible wall 280A and the transducer 314, while pressures above 50 psi may cause bursting of the walls 280A, 280B or deformation of the frame of the container 274. More preferably, the chamber 277 is pressurized to a pressure in the range of 8 to 15 psi above ambient pressure. This range is more preferred because it is safely within the practical limits described above.

Figure 48:
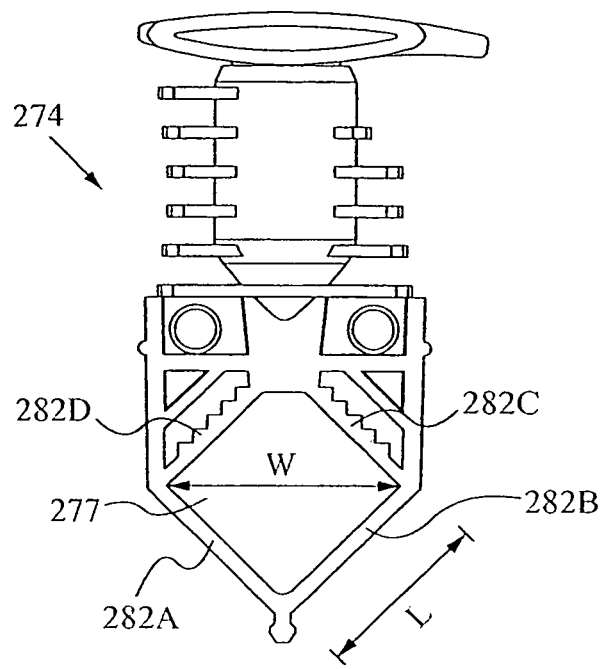
FIG. 48 is another schematic, front view of the container of FIG. 46.
Figure 49:
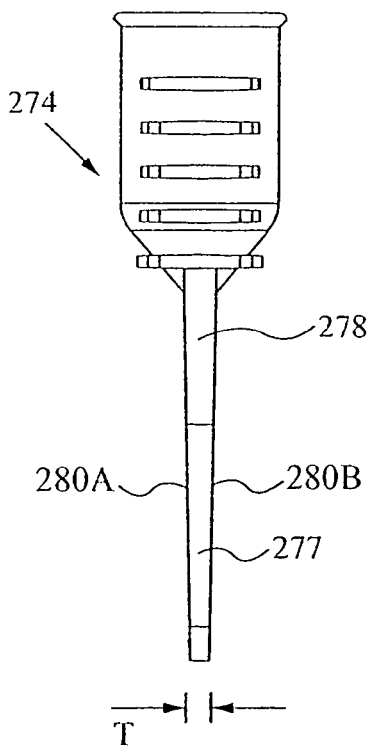
FIG. 49 is a side view of the container of FIG. 46.
Figure 50:
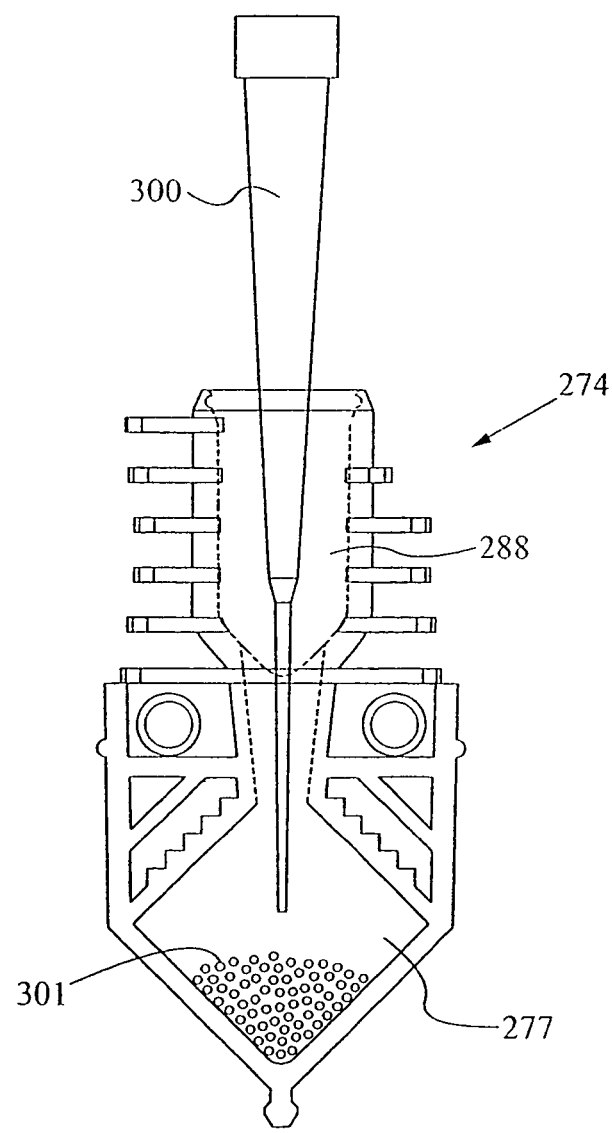
FIG. 50 is a view of a pipette inserted into the container of FIG. 46. The container is holding beads for rupturing cells or viruses.

A preferred method for disrupting cells or viruses using the apparatus 304 will now be described with reference to FIGS. 46-56. Referring to FIG. 50, beads 301 are placed in the chamber 277 of the container to enhance the disruption of the cells or viruses. In general, the beads 301 may be composed of glass, plastic, polystyrene, latex, crystals, metals, metal oxides, or non-glass silicates. The beads 301 may be porous or non-porous and preferably have a diameter in the range of 1 to 200 µm. More preferably, the beads 301 are either polystyrene beads, borosilicate glass beads, or soda lime glass beads having an average diameter of about 100 µm. The beads 301 may be placed in the chamber 277 using a funnel. The funnel should be sufficiently long to extend from the port 276 through the channel 288 and into the chamber 277. After inserting the funnel into the container 274, the beads 301 are placed in the funnel and the container 274 is tapped lightly (e.g., against a bench top) until the beads 301 settle into the bottom of the chamber 277. It is preferred that the funnel extend through the channel 288 and into the chamber 277 as the beads 301 are added to the chamber to prevent the beads from contaminating the channel. The presence of beads in the channel 288 would interfere with the subsequent stroke of the plunger into the channel. The quantity of beads 301 added to the chamber 277 is preferably sufficient to fill about 10% to 40% of the volume capacity of the chamber. For example, in the presently preferred embodiment, the chamber 277 has a volume capacity of about 100 □l, and 30 to 40 mg of beads are placed into the chamber.

After the beads 301 are placed in the chamber 277, the chamber is filled with a liquid containing the cells or viruses to be disrupted. The chamber 277 may be filled using a pipette having a pipette tip 300 (e.g., a standard 200 µl loading tip). Alternatively, the chamber 277 may be filled using a syringe or any other suitable injection system. The liquid should be a medium through which pressure waves or pressure pulses can be transmitted. For example, the liquid may comprise deionized water or ultrasonic gel for holding the cells or viruses in suspension or solution. Alternatively, the liquid may comprise a biological sample containing the cells or viruses. Suitable samples include bodily fluids (e.g., blood, urine, saliva, sputum, seminal fluid, spinal fluid, mucus, etc) or environmental samples such as ground or waste water. The sample may be in raw form or mixed with diluents or buffers. The liquid or gel may also include one or more lysing agents to aid in the disruption of the cells or viruses. One of the advantages of the present invention, however, is that harsh lysing agents are not required for successful disruption of the cells or viruses.

After the container 274 is filled with the liquid, the plunger 284 is inserted into the channel 288 to seal and pressurize the container 274. As the plunger 284 is inserted, the piston 292 compresses gas in the channel 288 to increase pressure in the chamber 277, preferably to about 8 to 15 psi above ambient pressure, as previously described.

Referring to FIG. 56, the holder 316 is then pushed or pulled away from the tip 326 of the transducer 314 (in the direction of the rod 348) so that the container 274 can be inserted into the holder. The container 274 is then placed in the holder 316. During the insertion of the container 274, the holder 316 should be held a sufficient distance from the retaining pins 342 to provide clearance between the pins 342 and the tab 275. After the container 274 is inserted into the holder 316, the holder is gently released and the spring 366 pushes the holder 316 along the guide 318 until the wall 280A contacts and conforms to the surface of the horn tip 326. When the wall 280A is coupled to the horn tip 326, the spring 366 applies to the holder 316, and thus to the container 274, a substantially constant force to press the wall 280A against the horn tip 326. The force provided by the spring 366 ensures effective coupling between the wall 280A and horn tip 326 as energy is transmitted to the chamber 277. As shown in FIG. 55, when the container 274 is moved into contact with the tip 326, the tab 275 slides between the retaining pins 342. The pins 342 prevent the container from sliding upward in response to the vibratory motion of the tip 326.

Referring again to FIG. 56, the cells or viruses in the chamber 277 are then disrupted by the pressure pulses and resulting bead movement in the chamber 277 generated by the vibration of the tip 326 against the flexible wall 280A. The magnitude of the force provided by the spring 366 to press together the wall 280A and the tip 326 is important for achieving a consistent transfer of energy between the transducer 314 and the chamber 277. If the force is too light, the wall 280A will only be held lightly against the tip 326, leading to poor transmission of the vibratory movement of the transducer 314. If the force is too strong, the container 274 or wall 280A may be damaged during sonication. An intermediate force results in the most consistent and repeatable transfer of energy from the transducer 314 to the chamber 277. It is presently preferred that the spring 366 provide a force in the range of 0.25 to 4 lbs., with a force of about 1 lb. being the most preferred.

When the transducer 314 is activated, the tip 326 vibrates to transmit ultrasonic energy into the chamber 277. There is a relationship between the coupling force between the wall 280A and the tip 326 and the desired amplitude of the vibratory movements of the tip 326. A balance can be sought between the coupling force and the amplitude. Generally, a light coupling force requires a greater amplitude to effect disruption of the cells or viruses, while a stronger coupling force requires less amplitude to effect disruption. For the range of coupling forces presently preferred (0.25 to 4 lbs.), the peak-to-peak amplitude of the vibratory movements should be in the range of 4 to 40 µm, with a preferred peak-to-peak amplitude of amount 15 µm.

Ultrasonic waves are preferably transmitted to the chamber 277 at a frequency in the range of 20 to 50 kHz, with a frequency of about 40 kHz being preferred. The duration of time for which the chamber 277 is sonicated is preferably in the range of 5 to 30 seconds. This range is preferred because it usually takes at least 5 seconds to disrupt the cells or viruses in the chamber, while sonicating the chamber for longer than 30 seconds will most likely denature or shear the nucleic acid released from the disrupted cells or viruses. Extensive shearing of the nucleic acid could interfere with subsequent amplification or detection. More preferably, the chamber is sonicated for about 10-20 seconds to fall safely within the practical limits stated above. The optimal time that a particular type of cell sample should be subjected to ultrasonic energy may be determined empirically.

Following disruption of the cells or viruses, the container 274 is removed from the holder 316 by pulling the holder 316 away from the tip 326 and withdrawing the container from the holder. The liquid or gel containing the disrupted cells and released nucleic acid is then removed from the container 274. This may be accomplished by centrifuging the container 274 and removing the supernatant using, e.g., a pipette or syringe. Alternatively, the liquid may be removed from the container 274 by setting the container on edge and at an incline until the beads precipitate. The beads usually settle in about 15 to 20 seconds. When the beads have settled, the plunger is withdrawn from the container 274 and the liquid is removed using a syringe or pipette. The released nucleic acid contained in the liquid may then be amplified and detected using techniques well known in the art.

One advantage of the apparatus and method of the present invention is that it provides for the rapid and effective disruption of cells or viruses, including tough spores, without requiring the use of harsh chemicals. In addition, the apparatus and method provide for highly consistent and repeatable lysis of cells or viruses, so that consistent results are achieved from one use of the apparatus to the next. The amount of energy that is absorbed by the liquid and beads held in the chamber 277 depends on the amplitude of the oscillations of the tip 326, the mass of the contents of the chamber 277, the pressure in the chamber 277, and the coupling force between the tip 326 and the wall 280A. All four of these parameters should be held substantially constant from one use of the apparatus to the next in order to achieve the same amount of disruption repeatably.

Many different modifications to the apparatus shown in FIG. 56 are possible. For example, the holder 316 may be slidably mounted to the base 308 by a variety of means, including rails, wheels, sliding in a groove, sliding in a cylinder, etc.

Alternatively, the holder 316 may be fixedly attached to the base 308 and the transducer 314 slidably mounted to the base. In this embodiment, an elastic body is positioned to apply a force to the transducer 314 (either directly or to a holder holding the horn) to press together the horn tip 326 and the wall 280A. In addition, in each of these embodiments, the elastic body may be positioned to either push or pull the transducer 314 or the container 274 towards each other. For example, the spring 366 may be positioned to push or pull the holder 316 towards the horn tip 326 or to push or pull the transducer 314 towards the holder 316. Further, multiple elastic bodies may be employed to apply forces to both the container 274 and the transducer 314 to push or pull them towards each other. All of these embodiments are intended to fall within the scope of the present invention.

Although a coil spring 366 is shown in FIGS. 37 and 56, it is to be understood that any type of elastic body may be used. Suitable elastic bodies include, but are not limited to, coil springs, wave springs, torsion springs, spiral springs, leaf spring, elliptic springs, half-elliptic springs, rubber springs, and atmospheric springs. The elastic body may also be compressed air or rubber. Preferably, the elastic body is a coil spring. Coil springs are preferred because they are simple and inexpensive to place in the apparatus and because the have a low spring rate. A compressed air system is also effective, but considerably more expensive. In embodiments in which the elastic body is a spring, the spring should have a low spring rate, preferably less than 4 lb./in. A low spring rate minimizes the effect that any variations in the thickness of the chamber 277 (due to small variations in manufacturing, filling, or pressurizing the container) will have on the magnitude of the force provided by the spring to press together the wall 280A and the horn tip 326.

Another advantage of the container 274 is that the chamber 277 holds the cells or viruses in a thin volume of liquid that can be uniformly sonicated easily. Referring to FIGS. 48-49, it is presently preferred to construct the container 274 such that each of the sides walls 282A, 282B, 282C, 282D of the chamber has a length L in the range of 5 to 20 mm, the chamber has a width W in the range of 7 to 30 mm, and the chamber has a thickness T in the range of 0.5 to 5 mm. In addition, the chamber 277 preferably has a width W greater than its thickness T. In particular, the ratio of the width W of the chamber to the thickness T of the chamber is preferably at least 2:1. More preferably, the ratio of the width W of the chamber to the thickness T of the chamber is at least 4:1. These ratios are preferred to enable the entire volume of the chamber 277 to be rapidly and uniformly sonicated. In general, the volume capacity of the chamber 277 is preferably in the range of 0.02 to 1 ml.

Referring again to FIG. 56, the transducer 314 is preferably an ultrasonic horn. The thickness of the chamber 277 (and thus the spacing between the walls 280A and 280B) is preferably less than half of the diameter of the tip 326 of the horn. This relationship between the thickness of the chamber 277 and the diameter of the tip 326 ensures that the ultrasonic energy received from the transducer 314 is substantially uniform throughout the volume of the chamber 277. As a specific example, in the presently preferred embodiment, the tip 326 has a diameter of 6.35 mm and the chamber 277 has a thickness of about 1.0 mm. In addition, the major wall 280A should be slightly larger than the surface of the horn tip 326 that presses against the wall 280A. This allows the flexible wall 280A to flex in response to the vibratory motion of the horn tip 326.

A preferred method for fabricating the container 274 will now be described with reference to FIGS. 46-47. The container 274 may be fabricated by first molding the rigid frame 278 using known injection molding techniques. The frame 278 is preferably molded as a single piece of polymeric material, e.g., polypropylene or polycarbonate. After the frame 278 is produced, thin, flexible sheets are cut to size and sealed to opposite sides of the frame 278 to form the major walls 282A, 282B of the chamber 277.

The major walls 282A, 282B are preferably cast or extruded films of polymeric material, e.g., polypropylene films, that are cut to size and attached to the frame 278 using the following procedure. A first piece of film is placed over one side of the bottom portion of the frame 278. The frame 278 preferably includes a tack bar 299 for aligning the top edge of the film. The film is placed over the bottom portion of the frame 278 such that the top edge of the film is aligned with the tack bar 299 and such that the film completely covers the bottom portion of the frame 278 below the tack bar 299. The film should be larger than the bottom portion of the frame 278 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 278, preferably by heat sealing. Heat sealing is presently preferred because it produces a strong seal without introducing potential contaminants to the container as the use of adhesive or solvent bonding techniques might do. Heat sealing is also simple and inexpensive. At a minimum, the film should be completely sealed to the surfaces of the side walls 282A, 282B, 282C, 282D. More preferably, the film is additionally sealed to the surfaces of the support ribs 295 and tack bar 299. The heat sealing may be performed using, e.g., a heated platen. An identical procedure may be used to cut and seal a second sheet to the opposite side of the frame 278 to complete the chamber 277.

The plunger 284 is also preferably molded from polymeric material (e.g., polypropylene or polycarbonate) using known injection molding techniques. As shown in FIG. 46, the frame 278, plunger 284, and leash 286 connecting the plunger to the frame may all be formed in the same mold to form a one-piece part. This embodiment of the container is especially suitable for manual use in which a human operator fills the container and inserts the plunger 284 into the channel 288. The leash 286 ensures that the plunger 284 is not lost or dropped on the floor. The plunger 284 is presently preferred as a simple, effective, and inexpensive mechanism for increasing pressure in the chamber 277 and for sealing the chamber 277 from the external environment. It is to be understood, however, that the scope of the invention is not limited to this embodiment. There are many other suitable techniques for sealing and pressurizing the container. In addition, any suitable pressure source may be used to pressurize the chamber. Suitable pressure sources include syringe pumps, compressed air sources, pneumatic pumps, or connections to external sources of pressure.

Summary, Ramifications, and Scope

Although the above description contains many specificities, these should not be construed as limitations on the scope of the invention, but merely as examples of some of the presently preferred embodiments. Many modifications or substitutions may be made to the apparatus and methods described without departing from the scope of the invention. For example, the container for holding the cells or viruses need not be one of the specialized containers described in the various embodiments above. Any type of container having a chamber for holding the cells or viruses may be used to practice the invention. Suitable containers include, but are not limited to, reaction vessels, cuvettes, cassettes, and cartridges. The container may have multiple chambers and/or channels for performing multiple sample preparation functions, or the container may have only a single chamber for holding cells or viruses for disruption.

Further, the support structure for pressing the transducer and the wall of the container against each other may have many alternative forms. For example, in one alternative embodiment, the support structure includes a vise or clamp for pressing the transducer and container against each other. In another embodiment, the apparatus includes a pressure system for applying air pressure to press together the transducer and the container. Alternatively, magnetic or gravitational force may be used to press together the transducer and the container. In each embodiment of the invention, force may be applied to the transducer, to the container, or to both the transducer and the container.

Therefore, the scope of the invention should be determined by the following claims and their legal equivalents.

What is claimed is:

1. A method for disrupting cells or viruses, the method comprising the steps of:

a) forcing a fluid sample containing the cells or viruses to flow through a chamber having a filter stack positioned therein, thereby capturing the cells or viruses on the filter stack, wherein the filter stack comprises at least two filters having different average pore sizes;

b) generating pressure waves or pressure pulses in the chamber by contacting a flexible wall of the chamber with a vibrating transducer, wherein said generating is performed under increased static pressure in the chamber, and wherein the increased static pressure is provided by a pressure source and enhances coupling of the flexible wall to the transducer.

2. The method of claim 1, wherein the transducer comprises an ultrasonic horn.

3. The method of claim 1, wherein a plurality of beads are disposed between at least two of the filters.

4. The method of claim 1, wherein at least two of the filters in the filter stack are separated by a gasket.

5. The method of claim 3, further comprising the step of agitating the beads between the filters.

* * * * *